(12) United States Patent
Tillim

(10) Patent No.: US 7,506,409 B2
(45) Date of Patent: Mar. 24, 2009

(54) HANDLE/GRIP AND METHOD FOR DESIGNING THE LIKE

(76) Inventor: Stephen L. Tillim, 490 Azalea Way, Los Altos, CA (US) 94022

( * ) Notice: Subject to any disclaimer, the term of this patent is extended or adjusted under 35 U.S.C. 154(b) by 756 days.

(21) Appl. No.: 11/204,122

(22) Filed: Aug. 16, 2005

(65) Prior Publication Data

US 2005/0278898 A1 Dec. 22, 2005

Related U.S. Application Data

(62) Division of application No. 10/279,111, filed on Oct. 24, 2002, now Pat. No. 6,988,295.

(60) Provisional application No. 60/330,527, filed on Oct. 24, 2001.

(51) Int. Cl.
*B25G 1/04* (2006.01)
*A45C 13/26* (2006.01)

(52) U.S. Cl. ............. 16/430; 16/110.1; 16/DIG. 12

(58) Field of Classification Search ........... 16/430, 16/431, 421, DIG. 12; 15/143.1, 145, 160, 15/257.5, 257.76; 30/232, 295, 308, 340, 30/341; 33/1 G, 510, 511, 512, 514.2; 74/551.1, 74/551.9, 553, 557; 81/177.1, 177.8, 124.5, 81/489; 173/162.1, 162.2, 169, 170; 482/47, 482/49, 44, 128; 280/821; 473/203, 526; 606/205–210; D8/303, 313, 61, 68, 80, 107, D8/DIG. 1, DIG. 6–DIG. 7; D7/649; D22/118
See application file for complete search history.

(56) References Cited

U.S. PATENT DOCUMENTS

| | | | |
|---|---|---|---|
| 288,096 A | 11/1883 | Morgan | |
| 336,540 A | 2/1886 | Wyttenbach | |
| 340,382 A | 4/1886 | Smith | |
| 700,492 A | 5/1902 | Henstock | |
| 825,985 A | 7/1906 | Schwertenberg | |
| 987,095 A | 3/1911 | Bonta | |
| D43,242 S | 11/1912 | Bernstein | |
| 1,188,394 A | 6/1916 | Bernstein | |

(Continued)

OTHER PUBLICATIONS

International Search Report from PCT/US04/12656 dated Dec. 6, 2005.

(Continued)

*Primary Examiner*—Chuck Y. Mah
(74) *Attorney, Agent, or Firm*—Reed Smith LLP; Juan Carlos A. Marquez, Esq.

(57) ABSTRACT

The present invention provides a design method and apparatus for a handle or grip providing a shape and structure that fills various regions of the hand except a region in an area over the underlying carpal tunnel. Such design method and apparatus provides for various supports and handles for use by a hand. In particular, the apparatus includes a generally boot-shaped body or portions thereof. The body or body portions include a radial section, an ulnar section and middle section. Furthermore the body has a distal (frontal) finger side, proximal (back) side, palmar side and a thumb side. The body also has radial and ulnar sides. These portions are shaped to engage the various corresponding regions of the inner surface of the hand. These sections and sides forming the body can be divided and used separately for individual applications of the present invention.

26 Claims, 47 Drawing Sheets

U.S. PATENT DOCUMENTS

| | | | |
|---|---|---|---|
| 1,229,658 A | 6/1917 | Sandow | |
| 1,648,354 A | 11/1927 | Lied | |
| 1,879,456 A | 9/1932 | Parsons | |
| 1,919,968 A | 7/1933 | Trabold | |
| 2,047,635 A | 7/1936 | Johst | |
| 2,370,026 A | 2/1945 | Elia | |
| 2,540,255 A | 2/1951 | Graves | |
| 2,561,941 A | 7/1951 | Moskowitz | |
| 2,621,688 A | 12/1952 | Wales | |
| 2,669,991 A | 2/1954 | Curutchet | |
| 2,669,993 A | 2/1954 | Curutchet | |
| 2,975,505 A | 3/1961 | Linskey et al. | |
| 3,129,939 A | 4/1964 | Stock | |
| 3,407,816 A | 10/1968 | Curutchet | |
| 3,557,792 A | 1/1971 | Rubin | |
| 3,713,350 A | 1/1973 | Brilando | |
| 3,741,665 A | 6/1973 | Smagala-Romanoff | |
| 3,972,333 A | 8/1976 | Leveen | |
| 4,043,343 A | 8/1977 | Williams | |
| 4,127,338 A | 11/1978 | Laybourne | |
| 4,161,051 A | 7/1979 | Brodwin | |
| 4,413,034 A | 11/1983 | Anderson | |
| 4,462,404 A | 7/1984 | Schwarz et al. | |
| 4,553,746 A | 11/1985 | Lee | |
| 4,572,227 A | 2/1986 | Wheeler | |
| 4,599,915 A | 7/1986 | Hlavac et al. | |
| 4,599,920 A | 7/1986 | Schmid | |
| 4,632,383 A | 12/1986 | Tsuzuki | |
| 4,641,857 A | 2/1987 | Gailiunas | |
| 4,644,651 A | 2/1987 | Jacobsen | |
| 4,674,330 A | 6/1987 | Ellis | |
| 4,674,501 A | 6/1987 | Greenberg | |
| D292,297 S | 10/1987 | Bingham | |
| 4,738,158 A | 4/1988 | Christol | |
| 4,785,495 A | 11/1988 | Dellis | |
| 4,798,377 A | 1/1989 | White | |
| 4,802,704 A | 2/1989 | Burns | |
| 4,830,002 A | 5/1989 | Semm | |
| 4,850,355 A | 7/1989 | Brooks et al. | |
| 4,877,280 A | 10/1989 | Milano | |
| 4,885,818 A | 12/1989 | Arterbury | |
| 4,899,618 A | 2/1990 | Christol | |
| 4,924,851 A | 5/1990 | Ognier et al. | |
| 4,941,460 A | 7/1990 | Working | |
| 4,962,747 A | 10/1990 | Biller | |
| 4,989,511 A * | 2/1991 | Clarke, Jr. | 101/123 |
| 5,002,561 A | 3/1991 | Fisher | |
| 5,005,674 A | 4/1991 | Piatt | |
| 5,024,119 A | 6/1991 | Linden | |
| 5,031,640 A | 7/1991 | Spitzer | |
| 5,044,058 A | 9/1991 | Voss | |
| 5,046,381 A | 9/1991 | Mueller | |
| 5,046,722 A | 9/1991 | Antoon | |
| 5,047,046 A | 9/1991 | Bodoia | |
| 5,047,049 A | 9/1991 | Salai | |
| 5,076,569 A | 12/1991 | Gootter | |
| 5,125,878 A | 6/1992 | Wingate et al. | |
| 5,143,463 A | 9/1992 | Pozil et al. | |
| 5,146,809 A | 9/1992 | Ruana | |
| 5,146,810 A | 9/1992 | Mueller | |
| 5,147,380 A | 9/1992 | Hernandez et al. | |
| 5,159,851 A | 11/1992 | Rahmes | |
| 5,160,343 A | 11/1992 | Brancel et al. | |
| 5,176,696 A | 1/1993 | Saunders | |
| 5,184,625 A | 2/1993 | Cottone, Jr. et al. | |
| 5,199,324 A | 4/1993 | Sain | |
| 5,211,655 A | 5/1993 | Hasson | |
| 5,230,704 A | 7/1993 | Moberg et al. | |
| 5,234,460 A | 8/1993 | Stouder, Jr. | |
| D339,468 S | 9/1993 | Mertz | |
| 5,277,683 A | 1/1994 | Wilkins | |
| 5,299,991 A | 4/1994 | Sato | |
| 5,318,589 A | 6/1994 | Lichtman | |
| 5,339,850 A | 8/1994 | Mertz | |
| 5,351,702 A | 10/1994 | Denjean | |
| 5,353,474 A * | 10/1994 | Good et al. | 16/421 |
| 5,366,476 A | 11/1994 | Noda | |
| 5,379,758 A | 1/1995 | Snyder | |
| 5,391,010 A | 2/1995 | Gorbunov | |
| 5,417,234 A | 5/1995 | Davis | |
| 5,423,531 A * | 6/1995 | Hoshizaki et al. | 473/560 |
| 5,445,479 A | 8/1995 | Hillinger | |
| 5,454,380 A | 10/1995 | Gates | |
| 5,470,162 A | 11/1995 | Rubin | |
| 5,470,328 A | 11/1995 | Furnish et al. | |
| 5,495,867 A | 3/1996 | Block | |
| 5,498,256 A | 3/1996 | Furnish | |
| 5,522,290 A | 6/1996 | Visser et al. | |
| 5,540,304 A | 7/1996 | Hawkins et al. | |
| 5,554,132 A | 9/1996 | Straits et al. | |
| 5,556,092 A | 9/1996 | Theken | |
| 5,562,693 A | 10/1996 | Devlin et al. | |
| 5,571,127 A | 11/1996 | DeCampli | |
| 5,578,050 A | 11/1996 | Webb | |
| 5,606,985 A | 3/1997 | Battiston et al. | |
| 5,634,382 A | 6/1997 | Fan | |
| 5,653,713 A | 8/1997 | Michelson | |
| 5,659,959 A | 8/1997 | Parlowski | |
| 5,660,082 A | 8/1997 | Hsieh | |
| 5,662,006 A | 9/1997 | Angeltun | |
| 5,692,265 A * | 12/1997 | Dalury | 16/430 |
| 5,728,121 A | 3/1998 | Bimbo et al. | |
| 5,730,751 A | 3/1998 | Dillon et al. | |
| 5,735,873 A | 4/1998 | MacLean | |
| 5,761,767 A | 6/1998 | Barton | |
| 5,782,853 A | 7/1998 | Zeevi et al. | |
| 5,785,443 A | 7/1998 | Rubin | |
| 5,791,671 A | 8/1998 | Tang et al. | |
| 5,797,165 A | 8/1998 | Armbrust | |
| 5,797,900 A | 8/1998 | Madhani et al. | |
| 5,805,256 A * | 9/1998 | Miller | 348/734 |
| 5,827,263 A | 10/1998 | Furnish et al. | |
| 5,829,099 A | 11/1998 | Kopelman et al. | |
| 5,830,231 A | 11/1998 | Geiges, Jr. | |
| 5,833,580 A | 11/1998 | Chiu | |
| 5,846,221 A | 12/1998 | Snoke et al. | |
| 5,850,663 A * | 12/1998 | Hardy et al. | 15/236.01 |
| 5,885,018 A | 3/1999 | Sato | |
| 5,893,877 A | 4/1999 | Gampp, Jr. et al. | |
| 5,897,571 A | 4/1999 | Kazama | |
| 5,908,432 A | 6/1999 | Pan | |
| 5,920,944 A | 7/1999 | Biggs et al. | |
| 5,923,467 A | 7/1999 | Pericic et al. | |
| 5,935,149 A | 8/1999 | Ek | |
| 5,961,430 A | 10/1999 | Zuckerman et al. | |
| 5,976,121 A | 11/1999 | Matern et al. | |
| 5,979,015 A | 11/1999 | Tamaribuchi | |
| 5,980,511 A | 11/1999 | Bilitz et al. | |
| 5,987,705 A * | 11/1999 | Reynolds | 16/431 |
| 5,991,956 A | 11/1999 | Chapman | |
| 6,007,570 A | 12/1999 | Sharkey et al. | |
| 6,012,623 A | 1/2000 | Fealey | |
| 6,024,737 A | 2/2000 | Morales | |
| 6,029,780 A | 2/2000 | Phillips | |
| 6,030,409 A | 2/2000 | Lang | |
| 6,041,258 A | 3/2000 | Cigaina et al. | |
| 6,042,559 A | 3/2000 | Dobak, III | |
| 6,063,087 A | 5/2000 | Agee et al. | |
| 6,079,523 A | 6/2000 | Irvine | |
| 6,085,611 A | 7/2000 | Valdez | |
| 6,094,280 A * | 7/2000 | Hayasaki et al. | 358/1.9 |
| 6,094,780 A | 8/2000 | McGlothlin et al. | |
| 6,119,309 A | 9/2000 | Lu | |
| 6,129,622 A | 10/2000 | Seaman et al. | |

| | | | |
|---|---|---|---|
| 6,129,740 A | 10/2000 | Michelson | |
| 6,134,994 A | 10/2000 | Gomas | |
| 6,145,151 A | 11/2000 | Herron et al. | |
| 6,161,256 A | 12/2000 | Quiring et al. | |
| 6,161,974 A | 12/2000 | Nakagawa | |
| 6,217,536 B1 | 4/2001 | Gustafson | |
| 6,272,754 B1 * | 8/2001 | Hesprich | 30/232 |
| 6,305,244 B1 | 10/2001 | Takahama | |
| 6,354,618 B1 | 3/2002 | Liao | |
| 6,427,565 B1 | 8/2002 | Ping | |
| 6,530,125 B2 | 3/2003 | Shippert | |
| 6,543,388 B2 * | 4/2003 | Willinger et al. | 119/633 |
| 6,592,160 B1 | 7/2003 | Nicolay et al. | |
| 6,637,962 B1 | 10/2003 | Roche et al. | |
| 2001/0001630 A1 | 5/2001 | Nakagawa | |

OTHER PUBLICATIONS

"Grotenhuis Endoscopic Fenestration System developed in cooperation with J. A. Grotenhuis, M.D.," Synergetics, Inc., 1998, one page.
"Reverse Cut Diamond Arachnoid Knife developed with James E. Benecke, M.D.," Synergetics, Inc., 1996, one page.
"Deep Neuro Dissection Set," Synergetics, Inc., 1996, two pages.
"Dacey TruMicro Vertical Scissors," Synergetics, Inc., 1998, four pages.
"Skull Base Instruments developed with James E. Benecke, M.D.", Synergetics, Inc., 1996, two pages.
"Spetzler TruMicro Scissors," Synergetics, Inc., 1998, two pages.
"Spetzler TruMicro Pituitary & Micro Cup Forceps," Synergetics, Inc., 1998, two pages.
"Spetzler Microsurgical Set," Synergetics, Inc., 1999, one page.
"Dacey Microvascular Repair Instruments developed in cooperation with Ralph G. Dacey, Jr., M.D.," Synergetics, Inc., 1996, two pages.
Photocopy of Carpal Lock, 2000, one page, Working, U.S. Patent 4,941,460.
Splints, Dynamic Splints, Hand Splints, AliMed Catalog, 2000, pp. D25, D26, D29 and D30.
Web site brochure for Ergo Pen, 1999, five pages.
Steering Wheels and Quick Release Hubs, Pegasus Catalog, 2000, p. 107.
"Guide to the 2000 SAP United States Grand Prix", Road & Track, 2000, cover page, pp. 16 & 18, three advertisement pages for Ferrari, Kumo tires, and Suzuki.
Illustration of hammer in article entitled "Quake insurance is less of a bargain but it's still a good investment", San Jose Magazine, 2001, two pages.
"Carpal Tunnel Syndrome Strike Many, Easy to Treat", American Association of Neurological Surgeons, 2000, two pages.
Results of East patent search, re: Ergonomics, 2 pages, search performed in 2000.
Results of East patent search re: Medical Instruments, 15 pages, search performed in 2000.
Results of East patent search re: Pen , 1 page, search performed in 2000.
Result of Assignee patent search re: Synergetics patents, 2 pages, search performed in 2000.
"Hand Grip to Prevent and Alleviate Carpal Tunnel Syndrome", USPTO Disclosure Document No. 321372, filed Dec. 4, 1992, 3 pages and 1 page of PTOL-362 form.
Result of Patent Search on "parallel grip" on USPTO website, no date provided.
"Jamar Dynamometer", North Coast Medical, Inc., San Jose, CA 95125, no date provided.
International Search Report dated Feb. 28, 2005.
International Search Report dated Nov. 29, 2004.
International Search Report dated Jul. 14, 2004.
Photocopy illustration of known prior art rongeur, no date provided.

* cited by examiner

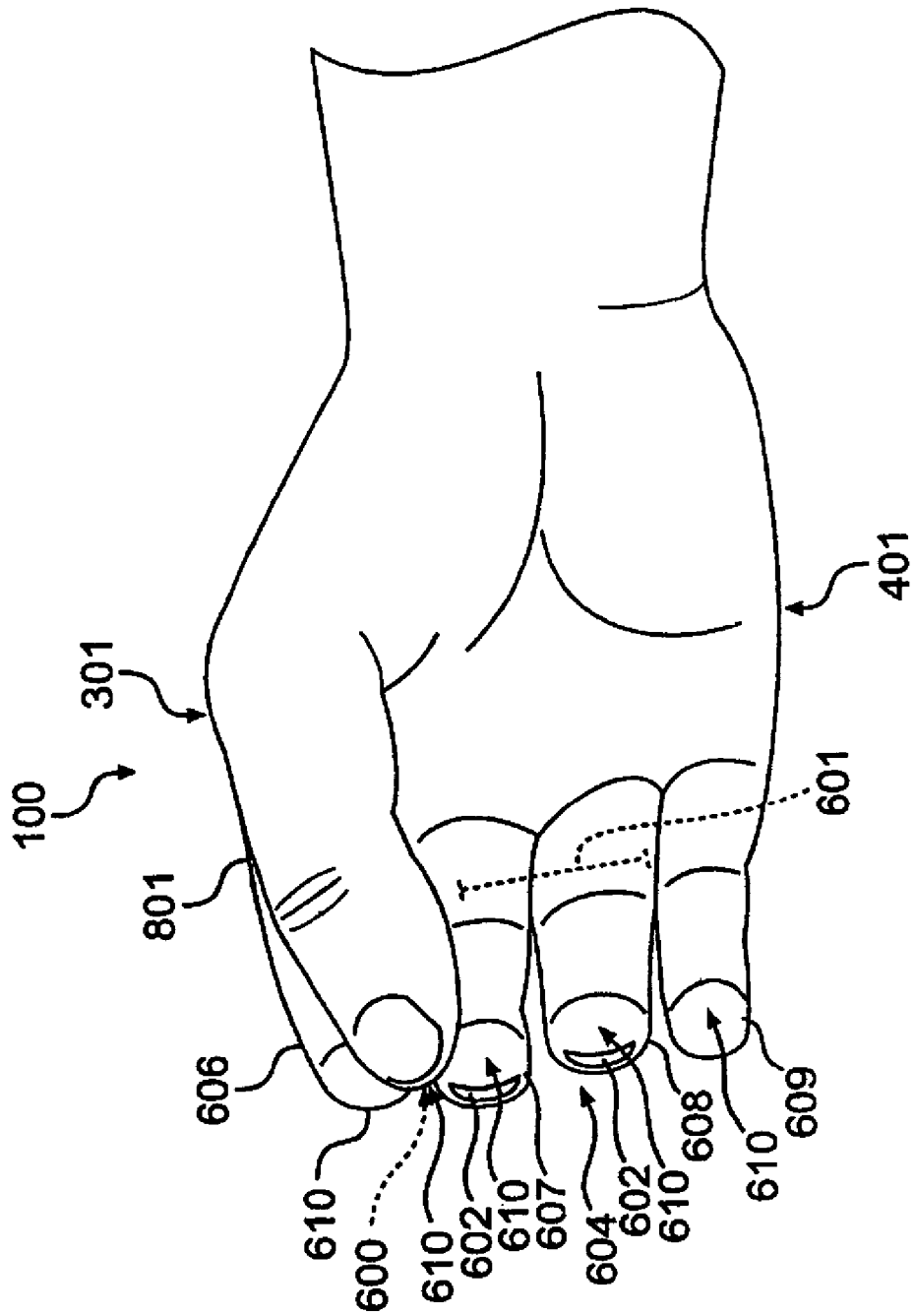

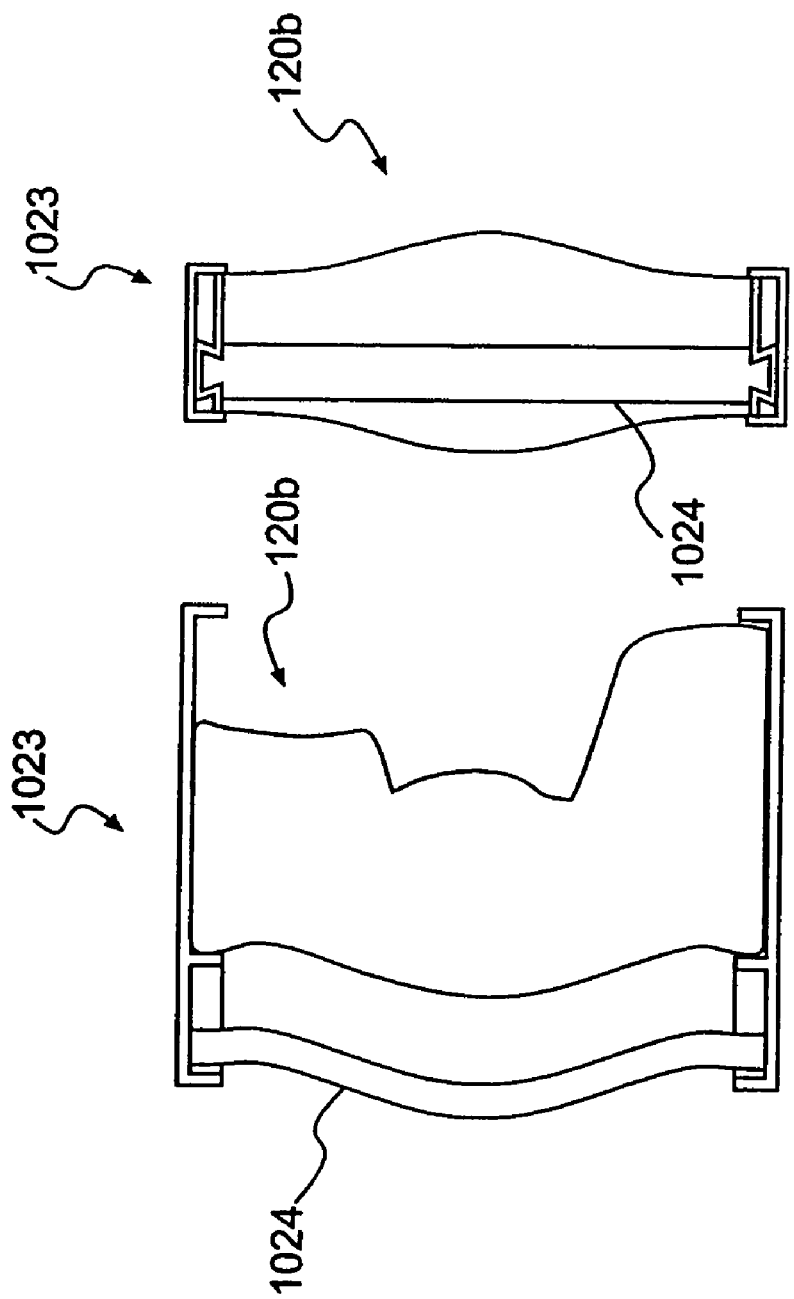

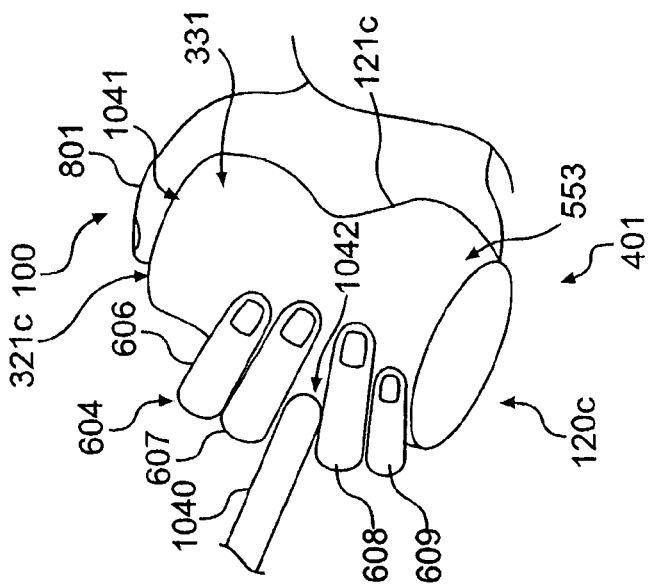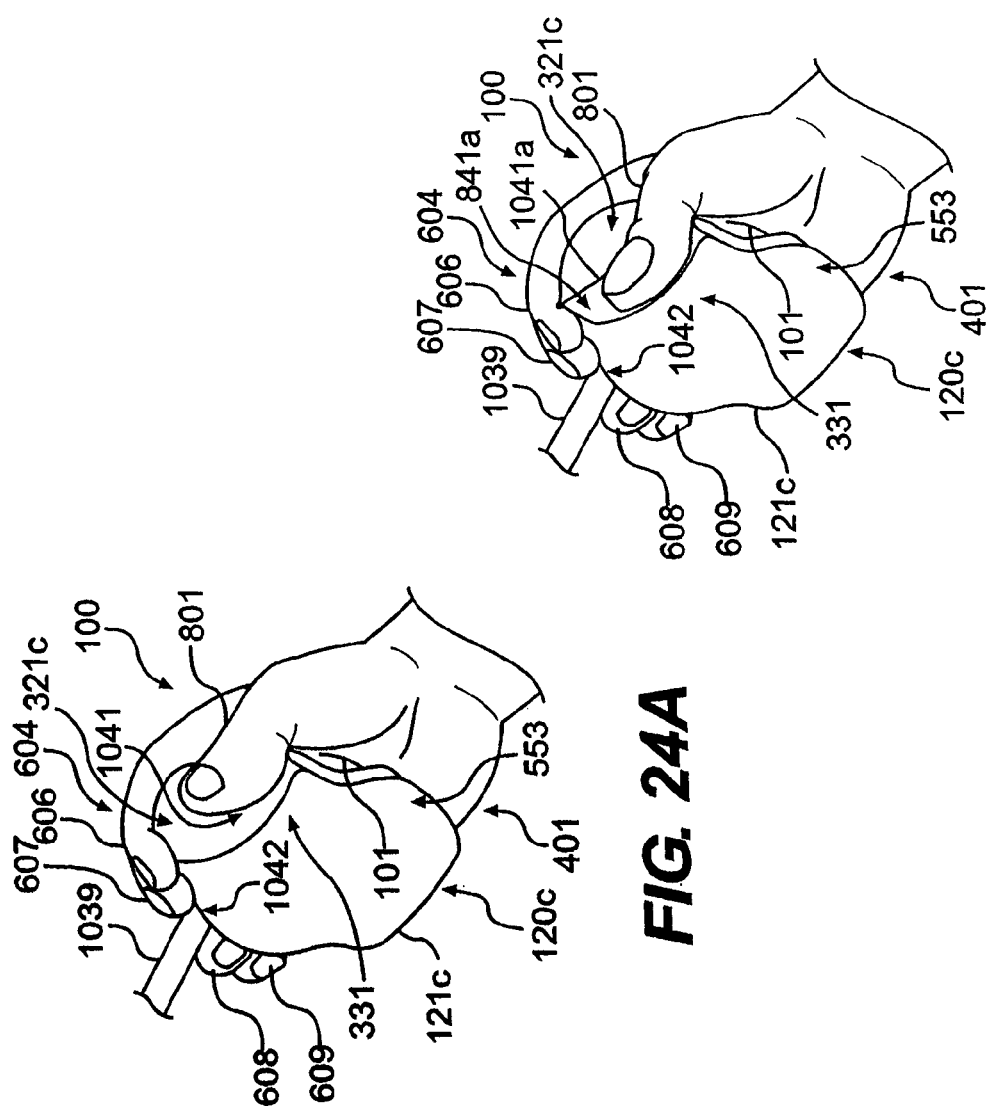
FIG. 24B
FIG. 24A1
FIG. 24A

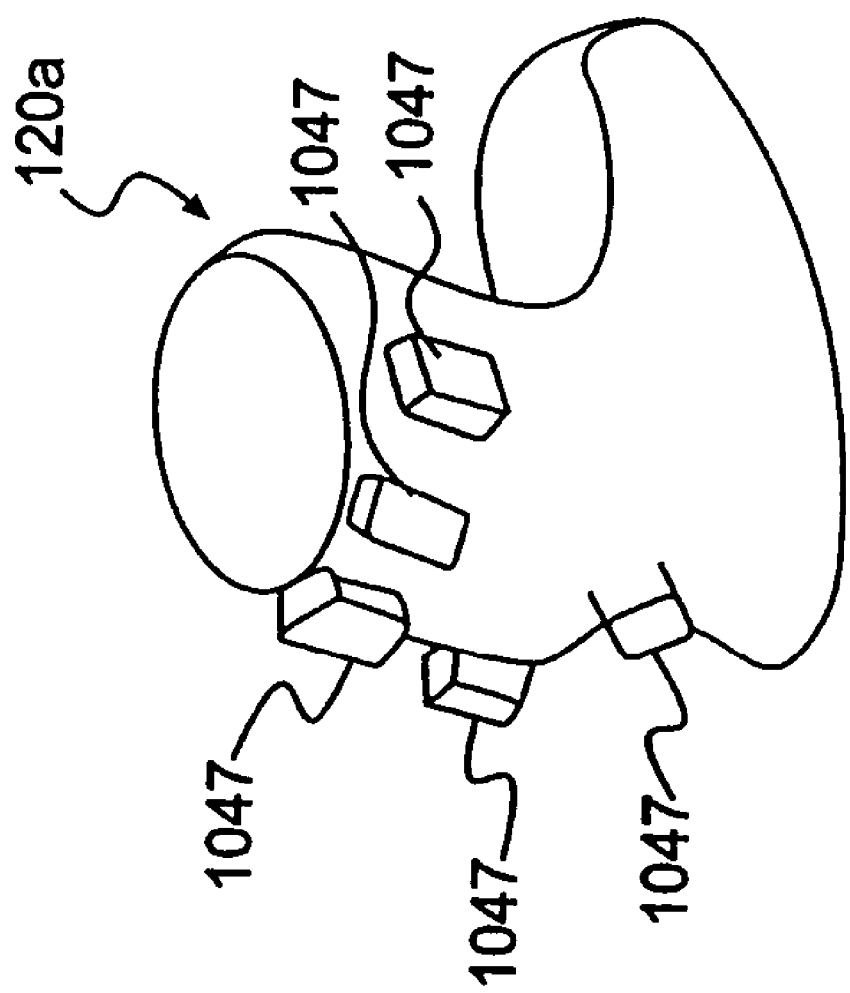

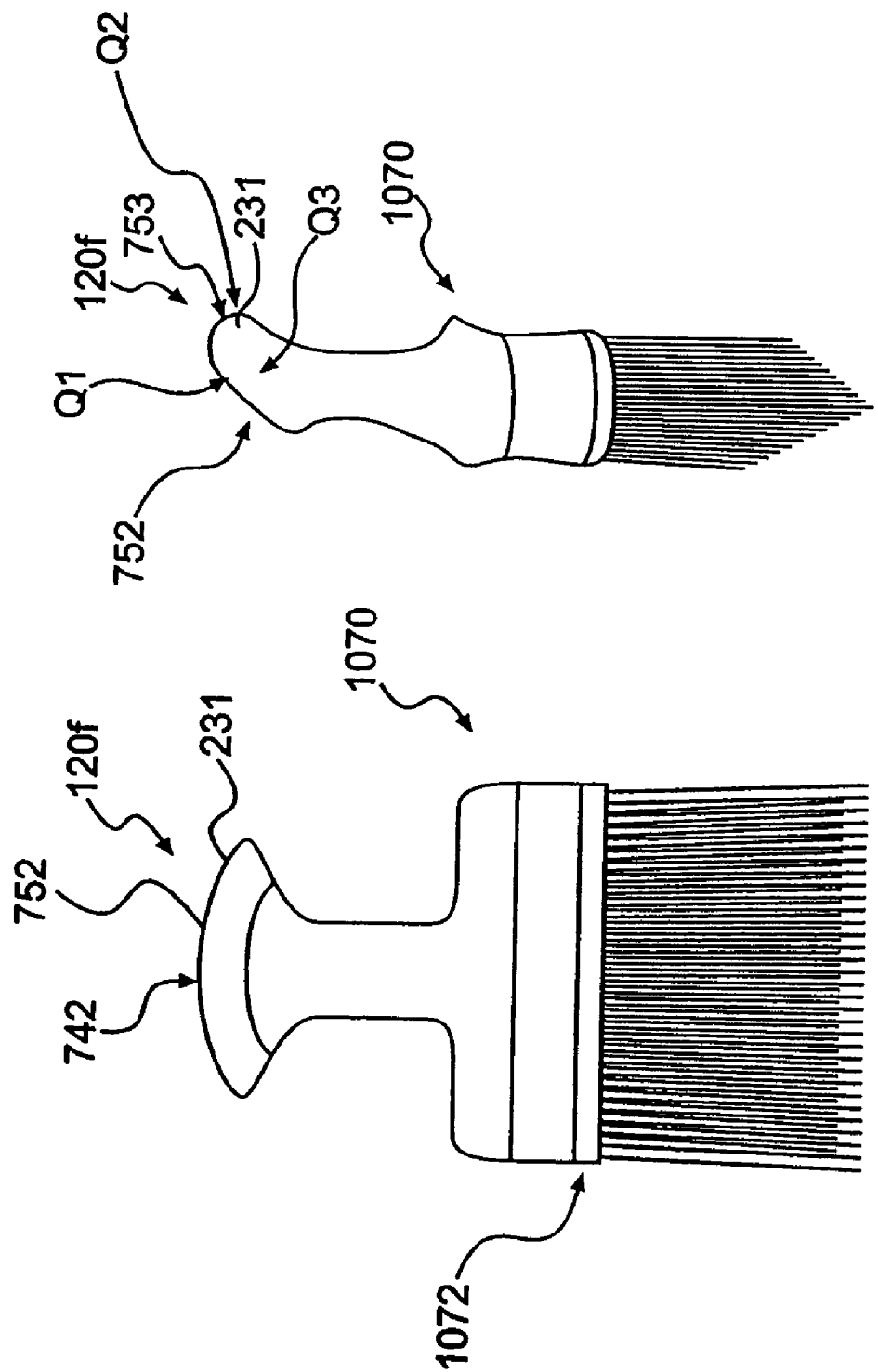

HANDLE/GRIP AND METHOD FOR DESIGNING THE LIKE

CROSS-REFERENCE TO RELATED APPLICATIONS

This application is a Divisional of U.S. application Ser. No. 10/279,111 filed Oct. 24, 2002, now U.S. Pat. No. 6,988,295 the entire disclosure of which is incorporated herein by reference. Priority is claimed based on U.S. application Ser. No. 10/279,111 filed Oct. 24, 2002, which claims priority to U.S. Provisional Application Ser. No. 60/330,527 filed Oct. 24, 2001, the entire disclosure of which is incorporated herein by reference.

CLAIM FOR PRIORITY

This application claims the priority of U.S. application Ser. No. 10/279,111 filed on Oct. 24, 2002, the entire disclosure of which is incorporated herein by reference, which claims the priority of the U.S. Provisional Patent Application Ser. No. 60/330,527 filed on Oct. 24, 2001, the entire disclosure of which is incorporated herein by reference.

FIELD OF THE INVENTION

The present invention provides a design method and apparatus for a handle or grip providing a shape and structure that fills various regions inside the hand except a region at an area of the hand over the underlying carpal tunnel. Such design method and apparatus provides for various supports and handles for use by a hand. In particular, the apparatus discussed in the present application includes a generally boot-shaped body. The body or body portions include a radial side, an ulnar side and a distal (frontal) side, proximal (back) side, palmar side and a finger and thumb side. These portions are shaped to engage the various corresponding regions inside the hand dependent upon the particular application. The body of the apparatus may be divided into a radial section, a middle section and an ulnar section. These sections that form the body can be divided and some of them can be used separately for individual applications of the present invention. Some of the applications that come from these sections will be discussed in other applications and some will be briefly described in this application.

BACKGROUND OF THE INVENTION

The upper arm contains a single bone (humerus). The forearm contains two bones (radius and ulnar). The wrist has seven small (carpal) bones. The proximal three carpal bones form a joint with the two forearm bones where wrist movement occurs. The distal four form a joint where they meet five metacarpal bones of the hand. ['Proximal' is near and 'distal' is away from the torso.] Motion is present at the wrist where the base of the thumb (1st metacarpal bone) meets its distal carpal bone. However, there is no movement at the joints of distal carpal bones to the remaining four metacarpal bones because they are tightly connected. The four metacarpal bones meet the phalangeal bones of the fingers to form the metacarpal-phalangeal (MP) joints. The thumb has two phalangeal bones (proximal and distal phalanges) and the long digits have three (proximal, middle and distal phalanges). Moveable joints form between the proximal (MP joint) and middle phalangeal bones as well as the middle (PIP joint) and distal (DIP) phalangeal bones. The carpal tunnel (CT) is a space formed on three sides by the internal surfaces of the wrist bones and inner surface of the transverse carpal ligament (TCL) on the forth side. The TCL is a strong dense ligament under the proximal palm that connects the radial (thumb side) and ulnar (small finger side) wrist bones. The size of the CT is regulated by genetic and environmental factors that influence bone size.

Referring to FIG. 1, FIG. 1 shows a palmar surface 100a of a palm 100b of a hand 100, such as a right or left hand, with horizontal creases 101 and longitudinal creases 201 creases and the skin creases 603 on the respective fingers 606, 607, 608, 609 and the location of the TCL 202. The median nerve is in a tunnel under the TCL 202. The horizontal crease 101 delineates the proximal part 105 of the MP joints 106 and cross the palmar surface 100a where the MP joints 106 flex. The longitudinal skin creases 201 lies in the valley between the thenar muscles 302 on the radial side 301 of the hand 100 and hypothenar muscles 402 on the ulnar side 401 of the hand 100. The longitudinal creases 201 lie over the CT 203. The longitudinal creases 201 are located in the skin where the metacarpal (MC) joint 107 of the thumb 801 flexes to oppose any of the fingers 606, 607, 608, 609 collectively referred to as the long fingers 604. The CT 203 indicated as being located between the dotted 203a and 203b of a distance indicated by the arrow 203c Continuing with reference to FIG. 1, the TCL 202 is thickest at its central portion and stabilizes nine flexor tendons that pass through CT 203 (one tendon flexes the thumb 801). The tendons in the CT 203 are wrapped with synovial membranes that form bursae that produce a lubricating substance allowing the tendons to move smoothly to pull the bones in the long fingers 604 and the thumb 801. The median nerve also passes through the tunnel and lies closest to the center of the TCL. The median nerve located in the CT 203 stretches with arm and wrist movement. A problem can result in that the extremes of wrist movement can kink the nerve and tendons where they enter the CT 203.

The shoulder is a ball joint that, allows the upper extremity to move in many directions. The elbow bends to pull (flexion) or push (extension) and rotates the forearm and hand (supination or pronation). Supination is rotation of the forearm to face the palm up. Pronation is rotation of the forearm to face the palm down. The wrist moves up and down (extension or flexion), sideways (radial or ulnar deviation) and in multiple directions by combining these movements.

The thumb 801 has five basic movements. The thumb 801 as a first movement flexes (moves closer) to or as a second movement extends (moves away from) in a direction parallel to the radial side 301 of the hand 100. As a third movement, the thumb 801 abducts or adducts to move up or down perpendicular to the palm 100b. Finally, as a fifth movement, the thumb 801 also opposes or touches any of the long fingers 604. The combination of these movements is called circumduction, which is moving the thumb 801 around in any direction.

The long fingers 604 have three muscle groups working individually or together to flex (pull) the proximal, middle and distal phalangeal bones. One muscle group is in the palm 100b and two muscle groups are in the forearm. The muscles in the palm 100b are the lumbrical muscles. These lumbrical muscles flex the proximal phalanges 606c, 607c, 608c, 609c at the MP joints 106. The lumbrical muscles are relatively small muscles in size.

Further, two other larger muscle groups are located in the front (volar surface) of the forearm and are called the superficial and deep flexor muscles. The superficial flexor muscle is close to the surface of the forearm and the deep flexor muscle lies underneath it. Each flexor forearm muscle is divided into subunits from which four tendons each arise contributing eight tendons that pass through the CT 203. The tendons from the superficial flexor muscle attach to and pull (flex) the middle phalanges 606b, 607b, 608b, 609b. The tendons from the deep flexor muscle attach to and pull the distal phalanges 606a, 607a, 608a, 609a. The deep flexor muscle is larger and stronger than the superficial flexor muscle. All the muscles combine function to sequentially flex the finger bones and produce varying degrees of finger curl to grip various shaped objects. Other muscles in the hand spread the fingers apart or pull them together (abduct or adduct).

When muscle units contract their girth enlarges to pull its smooth cable-like tendon, which in turn pulls its bone at a joint. The amount and strength of finger flexion depends upon the degree of each muscle unit's contraction. This depends on muscle size. Therefore, a larger muscle has greater contractile force. The largest and strongest forearm muscle is the deep flexor, which pull the distal phalangeal bone. Therefore the distal phalanges 606a, 607a, 608a, 609a of the long fingers 604 can exert the most gripping force.

The human hand has the unique ability to hold, grasp and move objects of various sizes, shapes and weight and to provide support to the human body. Handles and handgrips are tools to assist in these functions. Common handles and grips found on canes, bicycle handlebars, sanders, electric and pneumatic and other tools are usually tubular and made of a single size. Long finger bones vary in length. The middle and ring fingers 607 and 608 are longer than the index and small fingers 606 and 609. Because of this size difference, when the long fingers 604 grasp tubular handles the fingertips 610 do not end at the same line. Namely, the fingertip 610 of the small finger 609 ends before the fingertip 610 of index finger 606, which ends before the fingertip 610 of the ring finger 608 and that ends before the fingertip 610 of the middle finger 607 while the thumb 801 overlaps or lies next to the index finger 606.

Usually, the middle phalanges 607b, 608b of the middle finger 607 and the ring finger 608 and the distal phalanges 606a, 609a of the index finger 606 and the small finger 609 exert grip force along the same line on a tubular grip. Therefore, the smaller superficial flexor forearm muscle pulls the middle phalanges 607b, 608b of the middle finger 607 and the ring finger 608 while the deep flexor forearm muscle pulls the distal phalanges 606a, 609a of the index and small fingers 606 and 609, which is asymmetric use of the superficial and deep flexor muscles. Therefore, a problem can develop in that the different flexor muscles pulling different parts of the fingers 606-609 to grip a common handle do not work in concert.

Grip effort depends on brain messages to direct the amount of contraction a muscle segment exerts to the tendon pulling its phalange. The sum of all muscle contraction determines total grip strength. Asymmetrical use of the flexor forearm muscles to the fingers 606-609 limits potential use of the hand 100 to grip and can cause forearm muscle tension.

Such asymmetric use of forearm finger flexor muscles is forced by use of common handles and grips for tools and implements as for heavy equipment, machines, appliances and other devices and can frequently cause problems. This can adversely stress the finger and wrist joints, the contents of the CT 203, the muscles in the hand 100 and forearm and the median nerve. Such stresses are aggravated when common handles are gripped and used in relation to supporting the upper body.

The skin and tissue on the palm 100b and fingers 606-609 is another factor involved in gripping. It contains soft, compressible fatty tissue with tiny but strong perpendicular ligaments extending to the under surface of the skin from deep tissue. These ligaments prevent the skin of the palmar surface 100a from sliding. Aside from cushioning the skin of the fingers 606-609 has ridges and valleys (fingerprints) to enable the hand 100 to grip objects progressively tighter without slipping.

While, various diseases, such as hypothyroidism and diabetes can affect the median nerve in the CT 203, the design method and apparatus of the present invention relates to preventing or reducing traumatic injury and mechanical strain to the hand 100 and wrist. The median nerve in the CT 203 is compressed and flattened under the TCL 202 when the wrist is extended and the fingers 606-609 are forcefully gripping. This occurs, for example, from repeatedly gripping a steering wheel, repetitive vibration from hand sanders, repetitive compression from jackhammers and other forceful activities. These activities can irritate and inflame the median nerve as well as the synovial tissue wrapped around the tendons in the CT 203. The inflamed synovial tissue can swell to compress the median nerve in the CT 203. Scar can form as a result of the inflammation that increases friction to tendon motion in the CT 203. When the contents of the CT 203 are inflamed and the wrist is bent, the pressure in the CT 203 increases exponentially. Aging and repeated injury typically causes the TCL 202 to thicken, which decreases the size of the CT 203. Small size wrists are more prone to repetitive strain and carpal tunnel syndrome (CTS). The symptoms of CTS include wrist pain and finger tingling progressing to loss of sensation and thenar muscle weakness due to compression of the median nerve by the swelled contents of the CT 203.

The wrist works as a fulcrum when a person leans and places their weight on the palm 100b or fingers 606-609 while grasping a common handle to support the upper body. In this position the wrist is generally unsupported. The wrist in this condition maximally extends (bends back) and acts as a fulcrum to support upper body weight, especially when the elbow is straight. Supporting the hand 100 in this way also flattens the palm 100b. Resting the hand 100 on the longitudinal creases 201, in the valley between the thenar muscles 302 and the hypothenar muscles 402, places the weight of the upper body directly on the TCL 202 and transmits pressure to the median nerve which is immediately under it. These positions often produce symptoms of CTS, which could be prevented or reduced by a proper handle or grip.

Efficiency is reached when the parts of the hand 100 work in harmony. The goal of any handle or grip, as well as an objective the present invention is to promote such efficiency. An efficient handle or grip design should maintain the hand 100 in a comfortable position and also avoid placing substantial external pressure on the TCL 202 and reducing internal pressure in the CT 203. A further goal of any handle or grip design, as well as a further objective of the present invention is to facilitate the function of the hand 100 and forearm muscles so they work in concert. Furthermore, such a handle or grip design, as well as a further objective of the present invention should also promote a reduction in the amount of gripping strength typically required to hold a handle or grip. When less gripping strength is used to hold a handle or grip the internal pressure in the CT 203 can be reduced. A handle or grip that fulfills these goals should promote reduced incidence of CTS and repetitive strain disorder.

There are many handgrip patents that fit the hand by being convex and fill in the depression (valley) between the thenar and hypothenar muscle areas, which will pressure the median nerve. Some have depressions fitting the metacarpal and finger pads. For example, U.S. Pat. No. 6,142,918 is listed as a barbell system. U.S. Pat. No. 4,828,261 is listed as a handle for athletic equipment. U.S. Pat. No. 5,556,092 is round with indentations and listed as ergonomic handle. U.S. Pat. No. 5,979,015 is listed as an Ergonomic Hand Grip And Method Of Gripping but the fingertips do not end together to balance grip.

U.S. Pat. No. 5,806,091 is a Hand Grip Aid. This is a pad placed under the web spaces of the long fingers where they meet the skin of the palm. It is held in place by a rubber band or loop. The device merely adds firmness to the web space, where the long fingers lie across a handle as shown on a baseball bat, but the median nerve pressure problem remains.

U.S. Pat. No. 5,873,148 is titled as an Ergonomic Handle System made of four individual pieces that slide along a track on a base handle. Each piece has a groove to accept the finger. The circumferences of the two central pieces are larger than the outer and inner pieces.

U.S. Pat. No. 5,031,640 is titled as a Pad for Preventing Carpal Tunnel Syndrome. It provides a glove padding the thenar area, MP joints and the hypothenar area, and it empties in the region of the CT.

U.S. Pat. No. 6,183,400 is titled as a Hand at Rest Grip. It is designed to reduce gripping force when lifting weights. A 'palm heel' (a bulge) is provided to fit the ulnar side of the hand. It spreads to the CT stopping at the longitudinal creases over the median nerve. A strap is placed around the dorsal part of the hand to hold the hand in place. The thumb wraps around a flat bottom. The grip is hinged to attach around a bar for weight lifting. The 'palm heel' is curved and concave.

U.S. Pat. No. 5,829,099 is titled as a Universal Ergonomic Handle. It is contoured to match the anatomy of the hand and said to fit the anatomic rest position.

The handle in U.S. Pat. No. 5,761,767 incorporates a flat surface, i.e. "palm heel", extending from the upper surface of a tube to support the ulnar half of the hand. The object of the handle is to limit wrist movement when lifting weights by using a "hook type hand grip", U.S. Pat. No. 5,339,850 discloses an Orthopedic Hand Grip for Ambulation Aids, Tools and Other Implements. The grip includes a 'palm heel' extending across the longitudinal crease.

SUMMARY OF THE INVENTION

A method and apparatus for designing handles/grips is provided and is based on defined anatomical positions derived from the functional anatomy of a gripping hand. The design method and apparatus compensates for differences in finger length. The method uses curves made on the palm and long fingers when their tips end, side by side, at the same line while the thumb opposes the space between the thumb and index fingers. Apparatus, such as handles and grips, produced from this method make efficient use of the hand and the flexor muscles. The method produces and the apparatus also provides upper body supports while the hands rest on their fleshy thenar and hypothenar muscles and metacarpal joints without pressuring the transverse carpal ligament and median nerve.

An advantage of a handle of this design is that it does not contact the skin over the TCL because of the recessed proximal part of the middle section. Therefore the TCL is not compressed and no pressure is transmitted to the contents of the CT region during gripping or using a handle of this design as a support.

Another advantage is that it maintains the natural arcs of the fingers and palm for the natural accommodation of the hand to conform to it. In conforming to the neutral hand anatomy a handle or this design becomes more comfortable to hold or rest on.

Another advantage is that a larger part of the hand contacts handle. Common tubular grips contact the hand at the long fingers, metacarpals across the palm and thumb. Whereas a handle of this design adds contact to the fleshy thenar muscle surface between the thumb and index finger the and to the flattened hypothenar muscle region of the ulnar side of the hand in addition to the long fingers, metacarpal area and thumb. Thus there is the addition of the much greater hand surface area contacting a handle of this design for holding or gripping.

Another advantage when used as a bicycle support is that the larger contact area supports upper body weight across the metacarpals and the radial and ulnar muscle areas. Common handles, however, bear weight at the fleshy area between the thumb and index fingers and metacarpals while the fingers hold it tightly. Common handles do not have a section for the ulnar side of the hand to rest on.

Another advantage is that the squeezing action of the long fingers is directed against broader sections of the palm and hand. The radial side of a handle of the present design fills the space formed when the thumb opposes the index and middle fingers obliging the tips of the thumb, index and middle fingers to squeeze against the radial muscles. The ulnar side of the handle forces the small and ring finger to squeeze against the ulnar muscles. Forces in gripping common handles involve the long fingers squeezing a tube against the palm and specifically against the metacarpal-phalangeal joints.

Another advantage is that the tips of the long fingers end at the line. This places similar muscles to control similar bones. The strongest muscle for squeezing is the one that goes to the fingertip. Thus a handle of this design allows the strongest muscles to do the most efficient job they can do. (This is unlike the common handle where the fingers do not end together and dissimilar muscles are used for squeezing.)

Another advantage related to the long digits ending at the same line when using a handle of this design is that the forearm and hand muscles can work at their maximal potential. This advantage is increased because the thumb participates by opposing the index and middle finger unlike common handles where the thumb overlaps the long fingers.

Another advantage is all the digits work in concert to exert maximum effort while the opposing parts of the hand antagonize each other to equilibrate gripping forces. This is like squeezing an egg in the palm of the hand. When balanced the force cannot break it.

Another advantage is that less forearm muscle effort is needed because of the larger contoured gripping surface.

Another advantage is that it makes lifting objects easier because gripping takes less effort so lifting can be done primarily with antigravity shoulder and elbow muscles (deltoid, biceps etc.)

Another advantage is that it using such a handle does not compromise or distort the arteries supplying to the muscles in the hand. This is because such a handle does not touch either the TCL and underlying CT where the radial artery traverses or Guyon's tunnel at the pisiform bone (404) where the ulnar artery goes deep to supply the structures of the hand.

Another advantage is that it does not compromise, compress or distort the nerves that go to the hand.

This is because such a handle does not touch the TCL and underlying CT where the median nerve traverses or Guyon's tunnel at the pisiform bone (404) where the ulnar nerve goes deep along side the ulnar artery to innervate the hand. Therefore repetitive trauma to these nerves is reduced when gripping such a handle.

Another advantage of using a handle of this design is that there is less strain on contents of and pressure in the CT. Such a handle obliges the tendons to move synchronously in CT versus common tubular handles that force asynchronous tendon motion increases muscle strain and tendon strain in the CT.

Another advantage is that there is less compression, distortion or irritation of the median nerve by the superficial flexor tendons, which are closer to the TCL and the median nerve in the CT.

Another advantage is that the forces from vibrating equipment like power sanders, or impact jackhammers and wrenches are transmitted to the fleshy thenar and hypothenar muscles to absorb energy and are not directed to the CT.

The consummate advantage is that a handle of this design based on the advantages noted above will reduce acute and chronic irritation, trauma and strain to the tendons, bursa, joints, forearm muscles and median nerve. It is therefore expected that the result will be in a reduced incidence of CTS and repetitive strain syndrome for people who use handles or grips of this design.

It is an objective of the present invention to provide a method for developing a handle design based on objective hand measurements. Such measurements are made corresponding to the regions and surfaces of the hand as if it was in the position of holding a handle.

It is objective of the present invention to provide a design method and apparatus for a handle or grip that does not place substantial pressure at the CT region.

It is an objective of the present invention to provide a design method and apparatus for a handle or grip having greater contact with the supportive areas of the hand.

It is an objective of the present invention to provide a design method and apparatus for a handle or grip so as to optimize use of the forearm flexor muscles to the thumb and long fingers and equilibrate forces for gripping, lifting, pulling, etc.

It is another objective of the present invention to provide a design method and apparatus for a handle or grip that does not place substantial pressure at the CT region when the wrist is in neutral position. This neutral wrist position is present when the wrist is neither excessively flexed nor extended or deviated toward the radial or ulnar directions.

It is another objective of the present invention to provide a design method and apparatus for a handle or grip that reduces or substantially eliminates increased pressure in the CT when the hand forcefully grips a handle or grip.

It is another objective of this invention to provide a design method and apparatus for a handle or grip to position the tips of the long fingers in substantial alignment for optimal use of the deep flexor muscles.

It is still another objective of the present invention to provide a design method and apparatus for a handle or grip that when used diffuses upper body weight to the region of the metacarpal phalangeal joints of the hand and to the radial and ulnar sides of the hand such as when the wrist is maintained in the neutral position.

It is still another objective of the present invention to provide a design method and apparatus for a handle or grip that utilizes reduced grip strength as compared to a common handle or grip.

It is still another objective of the present invention to provide a handle of various sizes and shapes depending on its purpose or use such as to reduce grip strength required for various applications.

It is still another objective of the present invention to provide handles related to various hand sizes to accomplish the above and other objectives of the present invention.

It is still another objective of the present invention to provide a handle whereby the width of the ulnar section of the handle is less than the width of the hand's hypothenar muscles.

According to a further aspect of the present invention, the distal side of an apparatus according to the present invention can include an elevated surface acting as a reference for positioning of the long fingers on the apparatus.

According to another specific aspect of the present invention, the apparatus of the present invention can include a groove or flattened area on the palmar side of the apparatus forming a rest for the MP joints from where the long fingers extend around the distal part of the apparatus such as a handle.

According to a further specific aspect of the present invention, the shell of the handle can open in front or through the center of its body and can also be flexible so that extensions from tools which utilize the handle can fit inside or with the handle for use in exchanging tools for use with the handle or grip.

According to another specific aspect of the present invention, the periphery of the handle can be combined into a glove to provide versatility in use of the handle for various applications.

According to a further aspect of the present invention, the handle can be separated into various parts so that such parts can be respectively used for certain functions i.e. luggage handle, stylus etc.

It is still another objective of the present invention to provide directions to position a handle or grip so that the wrist in relation to the hand is placed in the neutral position. The neutral wrist position is achieved by arranging two intersecting planes, such that one of the intersecting planes passes through the forearm and the other intersecting plane passes from the base of the thumb through the fingers, and such that the angle between the two intersecting planes is in a range of from about ten degrees to about forty-five degrees, desirably less than or equal to thirty degrees, when the hand is in a variant of the described T Position.

Therefore, in a handle or grip of the present invention the long fingers end in a line adjacent to each other and there is no contact of the handle to the longitudinal crease. Furthermore, the metacarpal bones are arched and the ulnar side of the handle does not touch the longitudinal crease, while the thumb is positioned to oppose the space between the thumb and middle fingers. In a handle or grip of the present invention the ulnar side of the handle has an extended contact area with the ulnar side of the hand, and the web space at the thenar muscles on the radial side of the handle is in full contact with the proximal side of the radial section.

Also, in the design method and apparatus for a handle or grip of the present invention, the design method and apparatus is based on measurements made of the hand in a functional or gripping position, and handle size is desirably based on the distance between the thumb tip and the index and long fingertips.

Additionally, in the design method and apparatus for a handle or grip of the present invention, the shape of the palmar and distal (front) parts of a handle can be formed in the shape of a "coke bottle curve" where the ulnar side has a smaller arc than the radial side, and providing a shape that bulges to compel the longer middle and ring fingers to end at the same line as the index and small fingers.

Furthermore, in the design method and apparatus for a handle or grip of the present invention, the body can be trisected into radial, middle and ulnar sections, which can be used independently or together. Such versatility allows that the sides of sections may be attached to tools. Also, the body of a handle or grip of the present invention can be bisected or split along a plane passing through the palmar to thumb sides or another plane passing through the proximal to distal sides of the handle or grip of the present invention for various applications. In addition, the body can be cut along diagonal, oblique or tangential planes for various uses or purposes.

Also, in a handle or grip of the present invention, one side of the body of the handle or grip can be the mirror image or be dissimilar to the other side, depending upon the use or purpose of the handle or grip.

Therefore, the present invention provides a design method and apparatus for a handle or grip providing a shape and structure that fills various regions of the hand except a region in an area over the underlying carpal tunnel. Such design method and apparatus provides for various supports and handles for use by a hand. In particular, the apparatus includes a generally boot-shaped body or portions thereof. The body or body portions include a radial section, an ulnar section and middle section. Furthermore the body has a distal (frontal) finger side, proximal (back) side, palmar side and a thumb side. The body also has radial and ulnar sides. These portions are shaped to engage the various corresponding regions of the inner surface of the hand. These sections and sides forming the body can be divided and used separately for individual applications of the present invention.

BRIEF DESCRIPTION OF THE DRAWINGS

The foregoing and additional features and characteristics of the present invention will become more apparent from the following detailed description considered with reference to the accompanying drawings in which like reference numerals designate like elements and wherein:

FIGS. 4A and 4B show the hand of FIG. 1 in a 'T Position' defined according to the present invention looking towards the inner surface of the fingers and viewed from the perspective of the forearm positioned away from the body;

FIGS. 24A-24D illustrate other embodiments using a handle of the present invention, as to be used for rotation such as with a screwdriver as illustrated in FIG. 24A, as when held in a hand for use as a rotating handle as illustrated in FIG. 24B, as a handle with buttons or switches for functional control in at least one in a plurality of locations as illustrated in FIG. 24C, and as integrated as a handle with an open slot in a glove as illustrated in FIG. 24D;

FIGS. 30A-30E illustrate other embodiments for a handle of the present invention for use with devices so that the handle fits in the palmar arch of the hand, with FIG. 30A illustrating a brace for stabilizing the wrist for CTS, with FIG. 30B illustrating the brace of FIG. 30A engaged with a hand, with FIG. 30C illustrating a front view and FIG. 30D illustrating a side view of a paintbrush with a handle of the present invention, and with FIG. 30E illustrating the handle of a paint brush of FIGS. 30C and 30D fitting in the palmar arch of the hand;

DESCRIPTION OF THE PREFERRED EMBODIMENTS

In order to more clearly and concisely describe the subject matter of the present invention, the following definitions are intended to provide guidance as to the meanings of specific terms used in the following written description. Also it is to be understood that the phraseology or terminology employed herein is for the purpose of description and not to be construed as limiting. The following sections relate to areas of the hand described in the background information and refer to FIG. 1.

Neutral Hand Position—'N POSITION'

Figure 2:
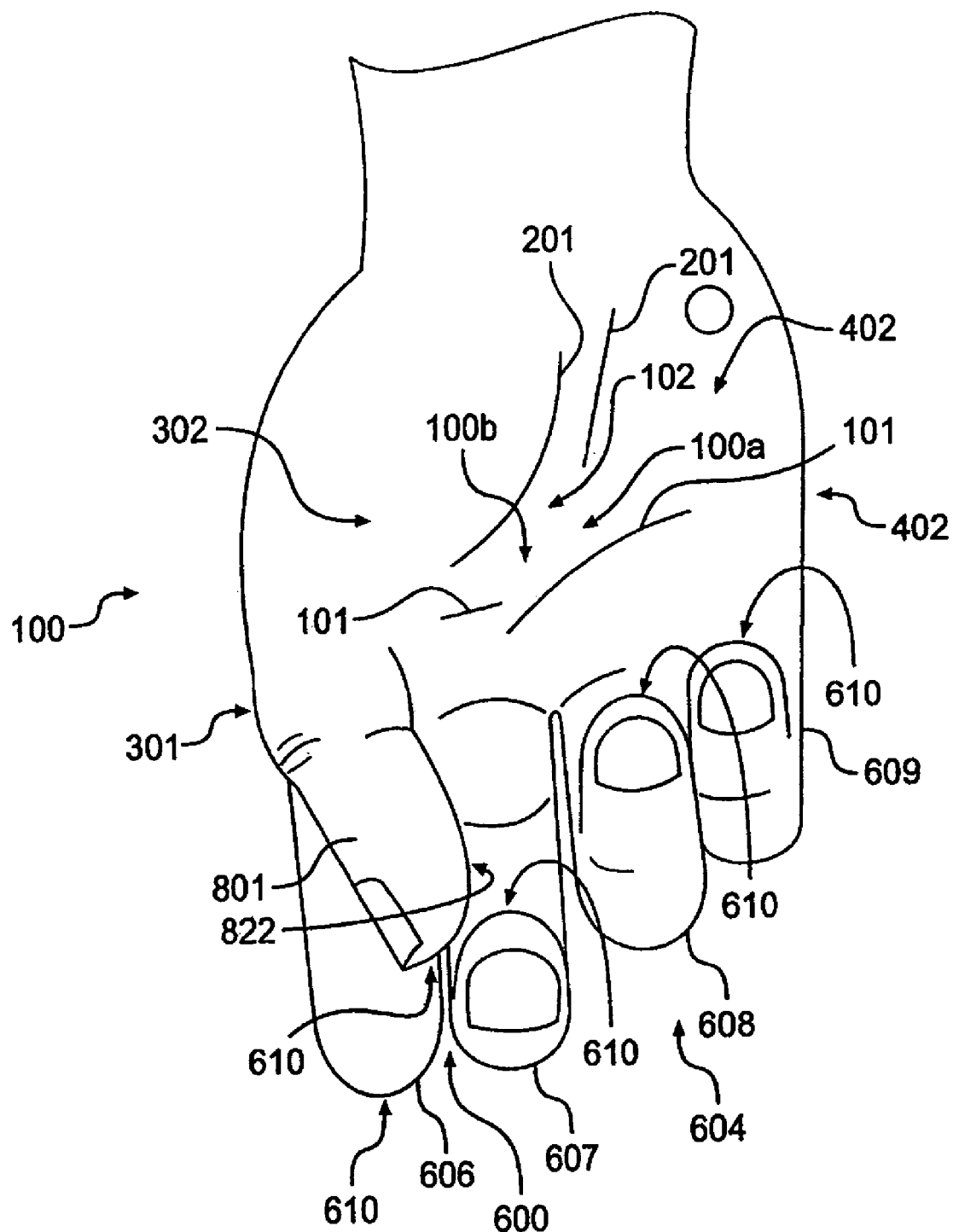
FIG. 2 shows the hand of FIG. 1 in a neutral position.

FIG. 2 shows a right hand in the neutral position. This position is the anatomic position at rest. It is called the neutral hand or 'N Position'. This universal human hand pattern is related to the shoulder and elbow resting positions and the way the carpal, metacarpal and phalangeal bones angle with each other when the upper extremity is dangling vertically at rest. The hand 100 is illustrated in FIG. 2 from the perspective of the palm 100b as if it was hanging at the body's side thereby substantially eliminating muscle contraction. In the 'N position', the radial (thumb) side 301 of the hand 100 is naturally rotated approximately thirty degrees towards the body. The proximal wrist joint, where the radius and ulnar bones meet the three proximal carpal (wrist) bones, are neither substantially flexed nor extended in the 'N Position'. The distal wrist bones angle away from the proximal wrist bones such that the hand 100 appears mildly extended at the wrist. The thumb 801 lies at a mild angle with reference to the ground and the long fingers 604 are comfortably flexed. The long fingers 606, 607, 608, 609 hang down, and the distal pad 822 of the thumb 801 rests next to or on the space 600 between the tips 610 of the index finger 606 and middle finger 607. The tips 610 of the middle 607, ring 608 and small 609 fingers lie progressively closer to the palm surface 100a of the palm 100b. The tip 610 of the index finger 606 is further from the palm 100b and less flexed than the middle finger 607. The skin folds at the horizontal creases 101 make long fingers 604 appear closer to the longitudinal creases 201 in this position than when hand 100 is positioned flat.

The concavity formed at the horizontal crease 101 when the hand is in the 'N Position' is referred to as the palmar arch 102 and shown in FIG. 2. The fleshy surfaces of the thenar muscle area 302 and hypothenar muscle area 402 lie proximal to the palmar arch 102. The horizontal creases 101 and longitudinal creases 201 become closer in the 'N Position' than when the hand 100 is flat.

Prone or 'P Position'

The prone or 'P Position', which is different from the above described 'N Position', occurs when the forearm is raised and turned over (pronated) so the palmar side of the hand 100 lies on a table with the wrist maintained in a neutral position. The radial side of the thumb 801 lies flat and its tip 610 touches the radial side of the index finger 606. In the 'P Position' the long fingers are slightly more flexed, with the ring finger 608 and the small finger 609 being more flexed than index finger 606 and the middle finger 607, and with he tips 610 of the long fingers 604 being substantially in linear relation to each other when supported by a flat surface, such as a table.

Supine or 'S Position'

The 'S Position' is obtained from the 'P Position' when the forearm is raised and turned over (supinated) so the palm 100b faces up while maintaining the above described 'N Position'.

'T POSITION'

The 'T Position' as illustrated in FIG. 4A is obtained by moving the long fingers 606, 607, 608, 609 from the 'N Position' of FIG. 2 alongside each other so their tips 610 substantially align at the same level when the fingers are flexed. Next the thumb 801 is moved so its tip 610 touches the space 600 between the index finger 606 and long finger 607. The same position is obtained by opening a fist, aligning the fingertips 610 of the long fingers 604 and placing the tip 610 of the thumb 801 opposite to the space 600 between the index finger 606 and middle finger 607.

The fingernails 602 of the longer middle finger 607 and the ring finger 608 are shown because the middle finger 607 and the ring finger 608 flex more to align with the index finger 606 and small finger 609.

Another concavity shown in FIG. 4A is defined as the finger cup 601 indicated by the dotted line 601 in FIG. 4A. It is formed when the long fingers 604 flex to align in the 'T position'.

Figure 1:
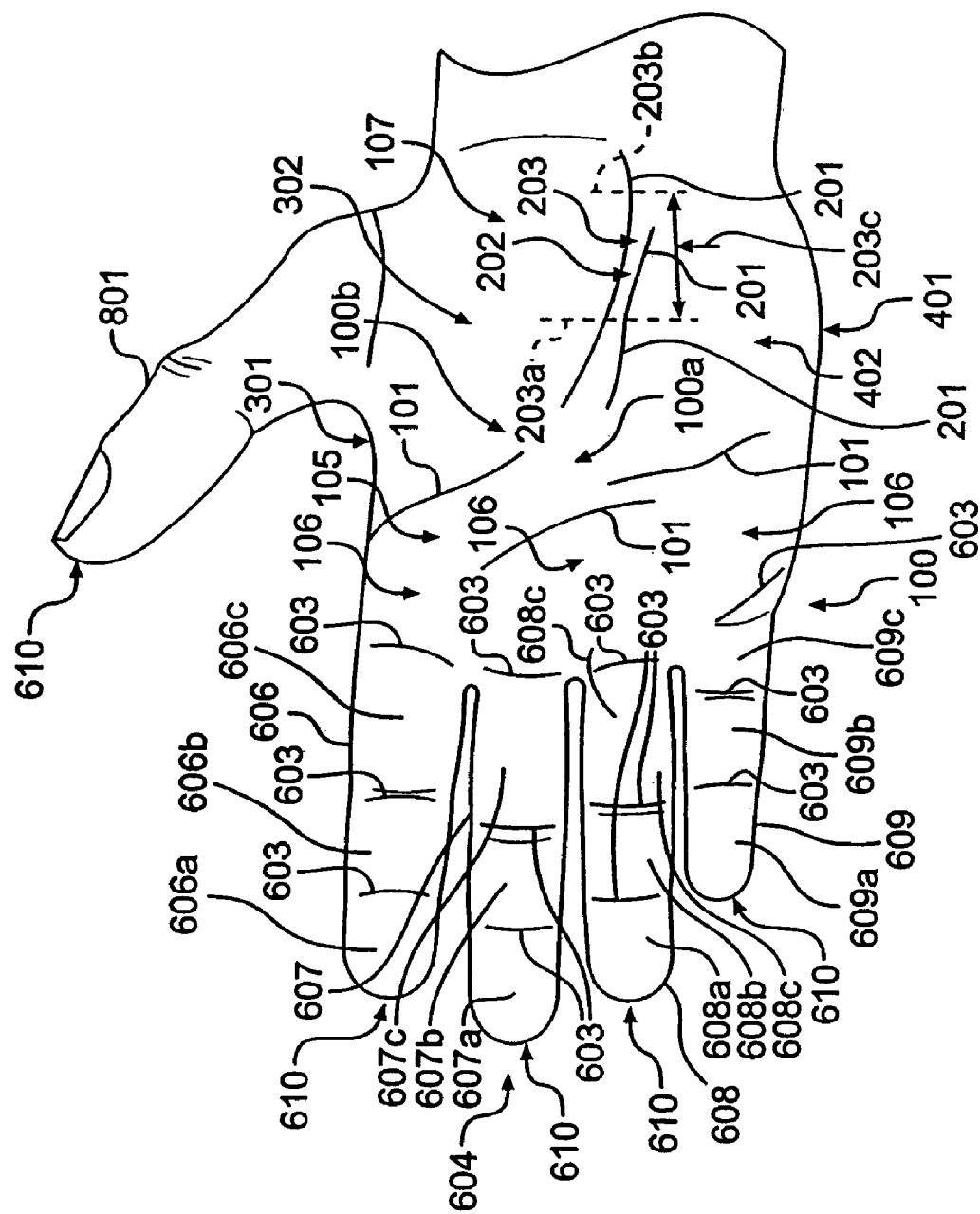
FIG. 1 shows a palmar perspective view of the hand.

The distal (near the end) finger creases 603 of the middle finger 607 and the ring finger 608 are not visible in FIG. 4A as they are in FIG. 1 because their distal phalanges 607a and 608a are positioned directly toward the viewer as illustrated in FIG. 4A.

Figure 3A:
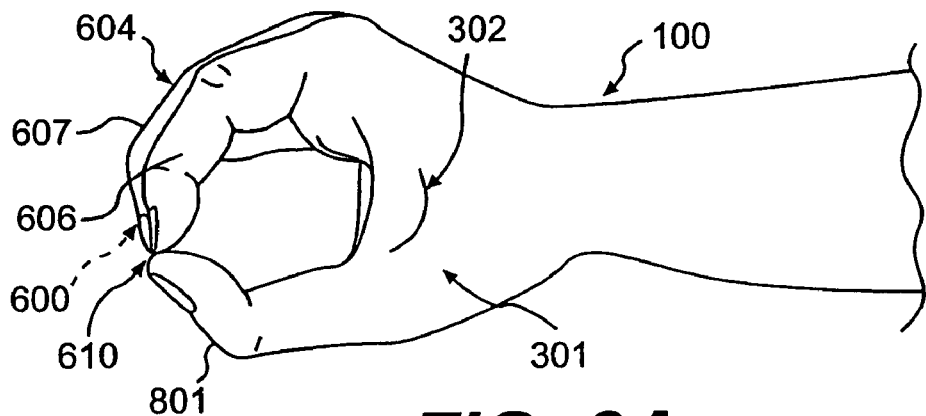
FIGS. 3A, 3B and 3C show corresponding views of the radial side of the hand in various 'T Positions' with the thumb and long fingers opposed, and with FIG. 3A illustrating the thumb and long fingers touching, and with FIGS. 3B and 3C respectively illustrating the thumb and long fingers separated at two distances.
Figure 3B:
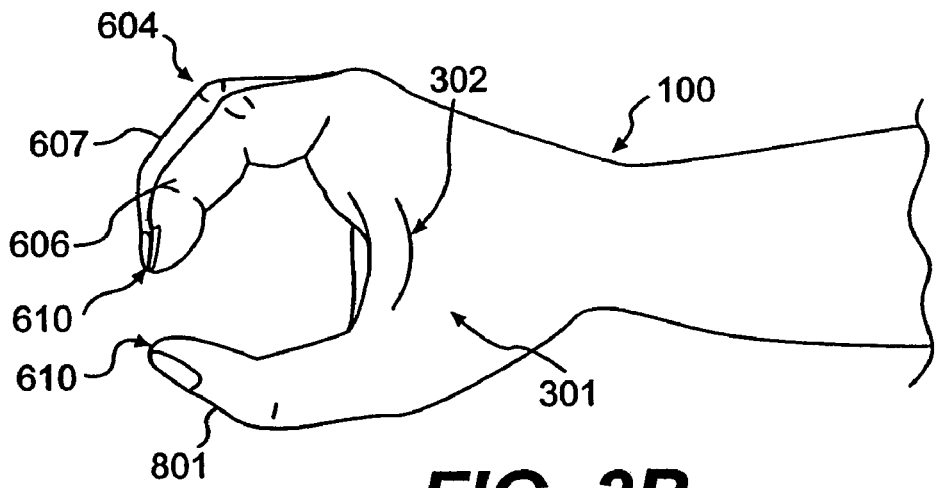
Figure 3C:
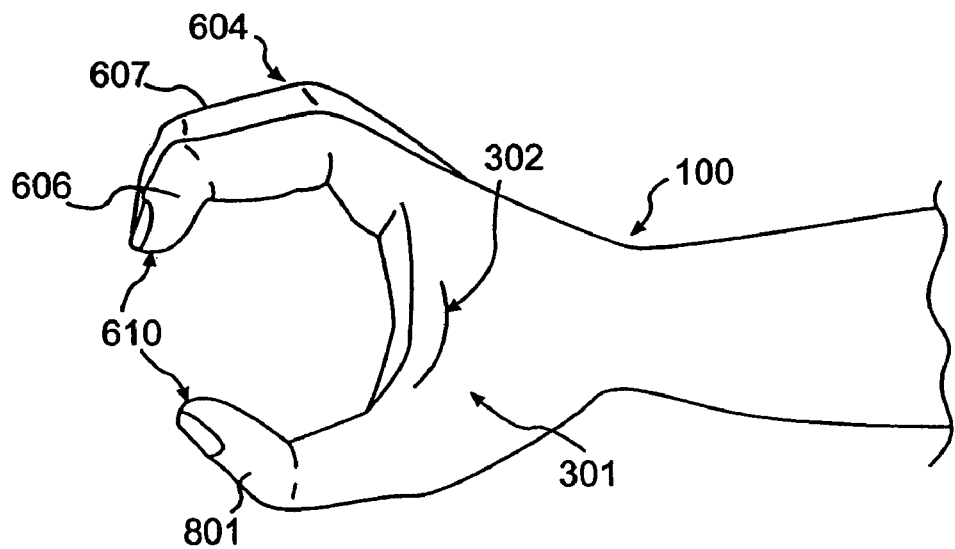
Figure 5A:
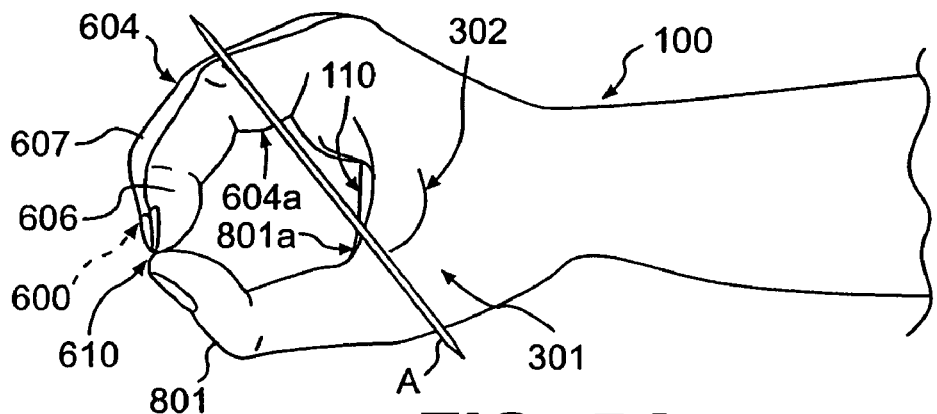
FIGS. 5A, 5B and 5C show corresponding views of the radial side of the hand in various 'T Positions' with the thumb and long fingers opposed, and with FIG. 5A illustrating the thumb and long fingers touching, and with FIGS. 5B and 5C respectively illustrating the thumb and long fingers separated at two distances, and with FIGS. 5A, 5B and 5C illustrating a plane passing from the inner edge of the thumb through the long fingers.
Figure 5B:
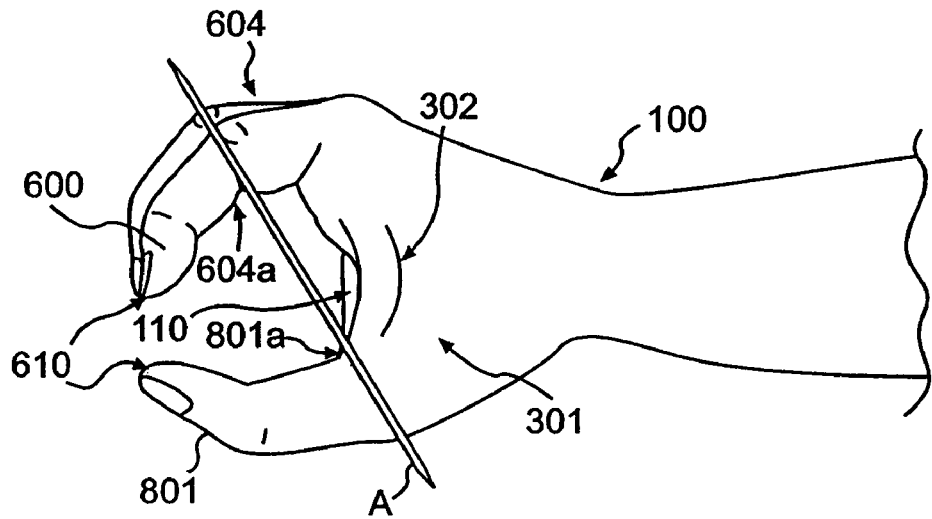
Figure 5C:
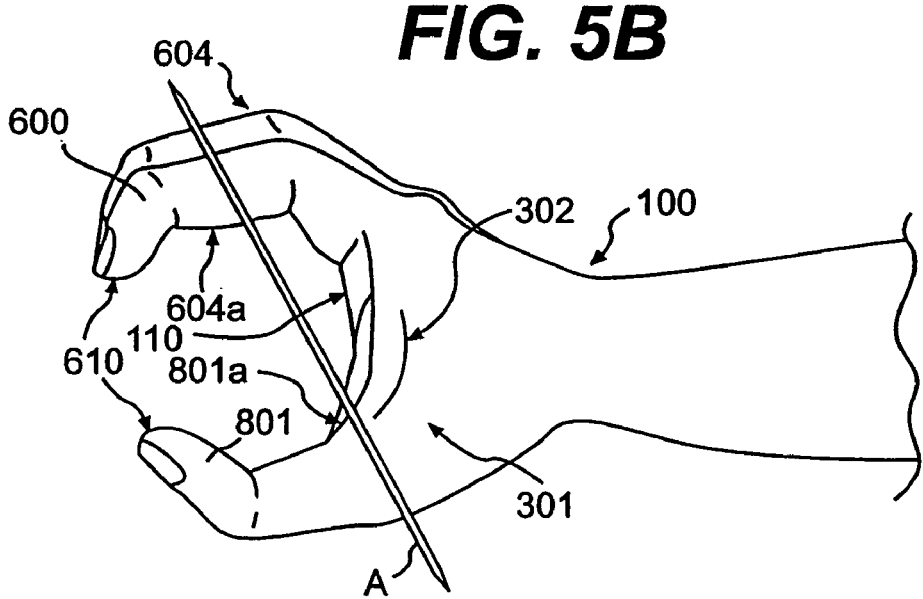

FIGS. 3A, 3B and 3C and FIGS. 5A, 5B and 5C show corresponding views of the radial side 301 of the hand 100 in various 'T Positions' with the thumb 801 and long fingers 604 opposed, and with FIGS. 3A and 5A illustrating the thumb 801 and long fingers 604 touching, and with FIGS. 3A, 3B, 5B and 5C respectively illustrating the thumb 801 and long fingers 604 separated at two distances, and with FIGS. 5A, 5B and 5C illustrating Plane A passing from the inner edge of the thumb 801 through the long fingers 604.

FIGS. 3A, 3B, 3C, 5A, 5B and 5C illustrate that the 'T Position' described above provides for the tips 610 of the long fingers 604 to remain in substantial linear alignment when the thumb 801 is touching or is spaced at a distance from the long fingers 604.

Figure 6:
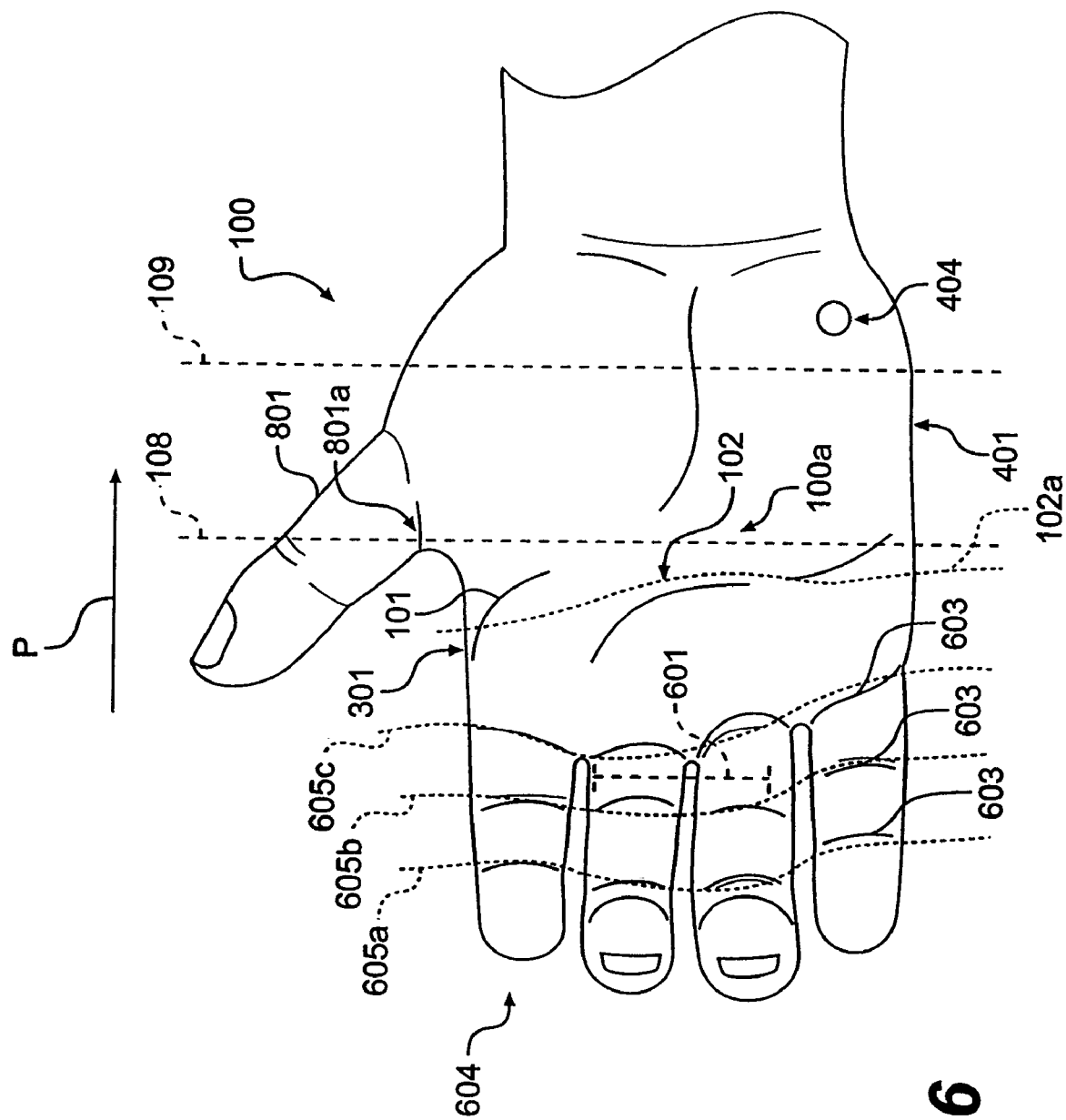
FIG. 6 shows a view of the hand's palmar surface illustrating the curved arrangements of the long finger creases and the palmar arch in the T Position with the thumb extended.
Figure 7:
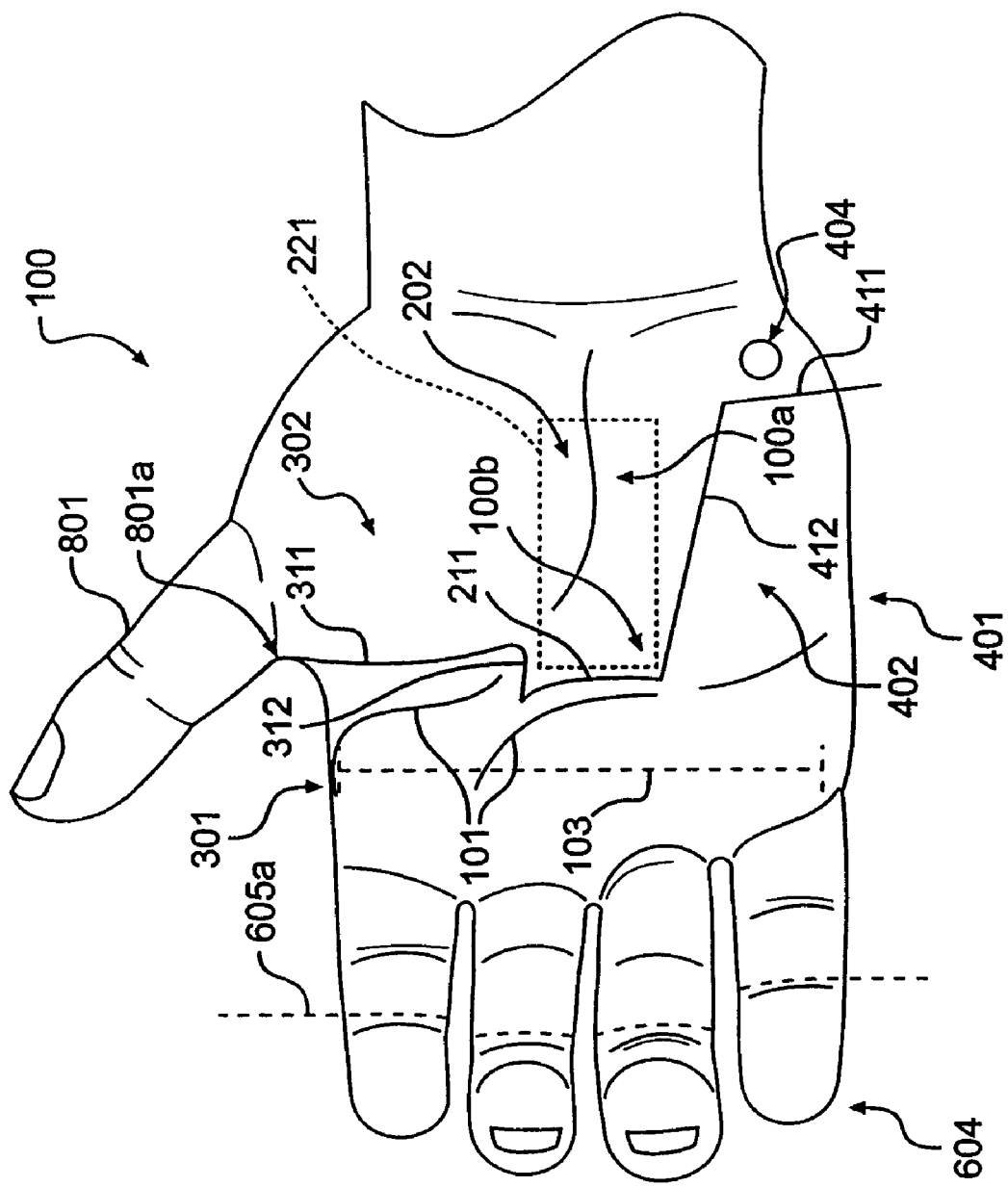
FIG. 7 shows a view of the hand's palmar surface in the T Position with the thumb extended and illustrating lines drawn on the hand to demarcate the location where a grip or handle of the present invention should contact the hand.
Figure 8:
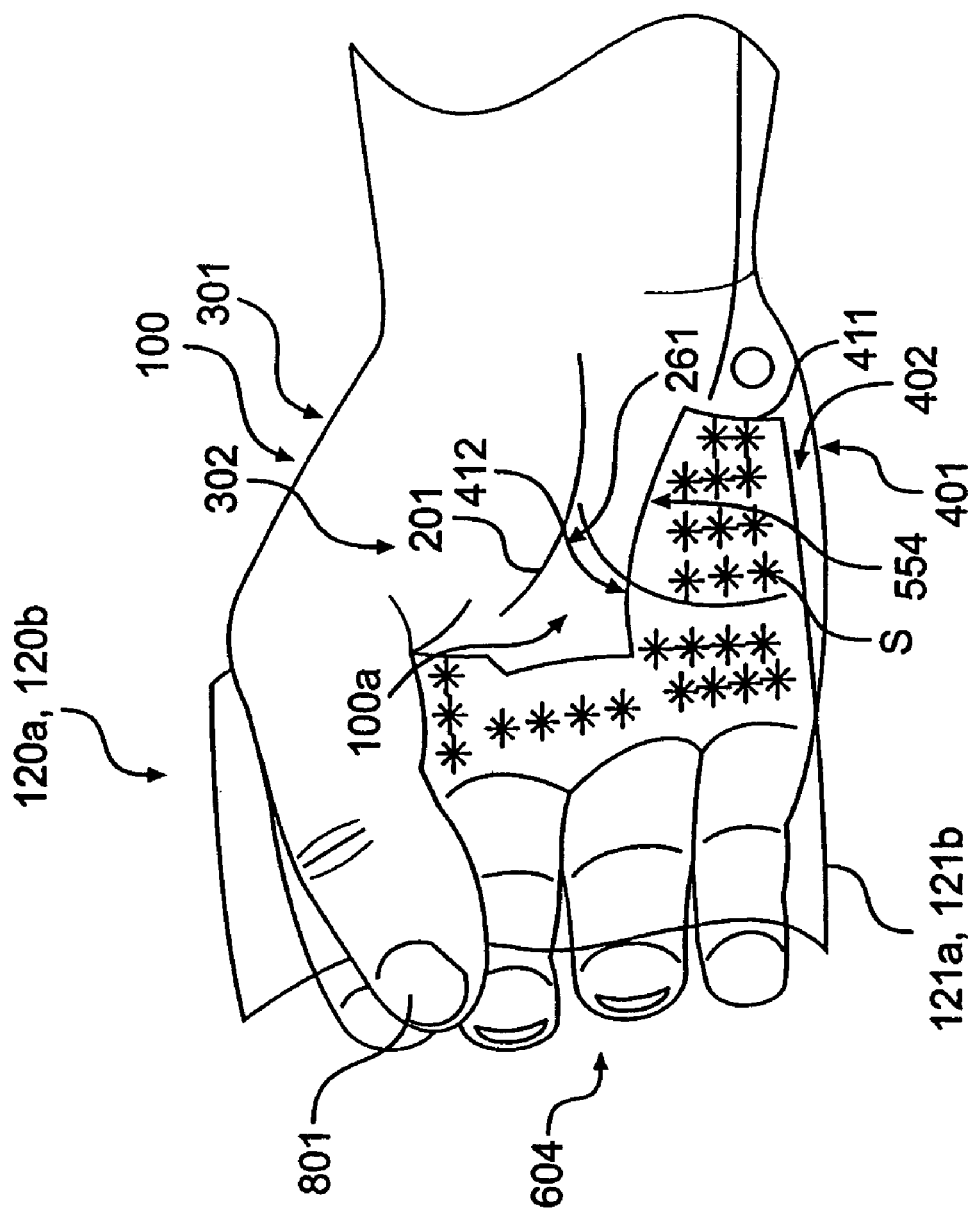
FIG. 8 shows the supported areas of a handle of the present invention in relation to the hand's palmar surface in the T Position.

Continuing now with reference to FIGS. 6, 7 and 8, the present invention provides a design method for determining measurements of the inner surface of the hand to develop sizes and shapes for handles or grips of the present invention.

Hand dimensions fall into groups, allowing formation of sizes (e.g. foot size and shoe size). Data to determine size groupings for the different hand positions can be collected. 30 male and 30 female right hands were measured from the radial side 301 to the ulnar side 401 of the hand 100 across the horizontal creases 101. The measurements (in 0.5-cm increments) ranged from 8.5-12 cm in males and 7-9 cm in females.

In such design method for determining measurements for the inner surface of the hand, referring to FIG. 6, curves indicated by the dotted lines 605a, 605b and 605c can be drawn from the radial side 301 of the hand 100 to the ulnar side 401 of the hand 100. Another curve indicated by the dotted line 102a can be drawn across the palmar arch 102 on the palmar surface 100a of the hand 100 when the hand 100 is in the 'T Position'.

FIG. 6 also illustrates three lines 605a, 605b and 605c extending across the finger creases 603 of the long fingers 604 with the curved line 102a extending across the palmar arch 102. The lines 605a, 605b and 605c curve to bend with the finger cup 601. Starting at line 605a, a series of parallel lines at various intervals can be drawn from the distal finger skin creases 603 from the radial side 301 to the ulnar side 401 of the hand 100 towards the proximal horizontal radial line 108 at the base 801 a of the thumb 801 in the direction of the arrow P. These parallel lines also continue from the proximal horizontal radial line 108 to end at the proximal horizontal ulnar line 109 distal to the pisiform bone 404.

Connecting such a series of parallel lines forms a surface that mirrors the surface anatomy of the hand 100. The size and dimension of such a surface of the hand 100 vary from person to person. However, the basic shape of such surface of the hand 100 is substantially the same although the surface area may differ, irrespective of whether the hand is small, large, wide or narrow.

Measurements from the above described contour mapping of the surface of the hand 100 can determine the size and shape of handles of the present invention mirroring the inner surface of the hand 100.

Refinements to the measurement area for developing sizes for a handle or grip of the present invention are illustrated with reference to FIG. 7. FIG. 7 shows the thumb 801 extended from the hand 100 and the long fingers 604 aligned in the 'T position'. Three lines 311, 211 and 411 cross the proximal part of the palm 100b to define a middle section or median void 221 indicated by the area substantially within the dashed lines of FIG. 7. The horizontal radial line 311 is distal to the base 801a of the thumb 801 and corresponds to the proximal horizontal radial line 108 in FIG. 6. The horizontal radial line 311 travels toward the ulnar side 401 of the hand 100 to end radial to the longitudinal creases 201. The horizontal ulnar line 411 crosses the ulnar side 401 of the hand 100 distal to the area of the pisiform bone 404 to travel toward the radial side 301 of the hand 100 across approximately ⅔rds of the hypothenar muscle region 402. The horizontal middle line 211 crosses the palm 100b and extends from the thenar muscle area 302 to the hypothenar muscle area 402 at the horizontal creases 101. The longitudinal radial line 312 connects the innermost point of the horizontal radial line 311 to the radial side of the horizontal middle line 211. The longitudinal ulnar line 412 connects the innermost of the horizontal ulnar line 411 to the ulnar side of the horizontal middle line 211.

Thus, FIG. 7 shows the area of where measurements will be taken to determine hand sizes for a handle according to the design method of the present invention. The width of the area taken across the metacarpals 103 substantially indicated by the dotted line in FIG. 7 is from the radial side 301 to the ulnar side 401 of the hand 100. As can be seen in FIG. 7, the measured surface area of the hand 100 which is bounded by the area between the line 605a to the proximal boundary defined by the lines 311, 312, 211, 412 and 411 does not touch the median void 221 of an area of the palmar surface 100a over the TCL 202 while the area of the finger cup 601 and palmar arch 102, as illustrated in FIG. 4A, are preserved when the hand 100 is in the 'T Position'.

As shown in FIG. 7, the width across the MP joints 103 of the palm 100b determines the length of the body of a handle of a design according to the present invention. The length of the body may include a part flaring beyond the radial side 301 and the ulnar side 401 of the hand 100 that nestle the index finger 606 and small finger 609 to prevent the hand 100 from slipping or sliding from side to side when engaging a handle of a design of the present invention.

Referring now to FIGS. 5A, 5B and 5C, another determinate for hand size measurement according to the design method of the present invention is illustrated. Plane A as illustrated in FIG. 5, touches the thenar muscle area 302 at the base 801a of the thumb 801 at the proximal horizontal line radial side 108, as shown in FIG. 6, and passes through the inner (palmar) surface 604a of the long fingers 604. FIGS. 5A, 5B and 5C show the view of the radial side 301 of the hand 100 in three variations of the T Position. FIG. 5A, illustrates the radial side 301 of the hand 100, with the tip 610 of the thumb 802 touching the tips 610 of the index finger 606 and middle finger 607. FIG. 5C also shows the thumb 801 maximally spread away from the long fingers 604. FIG. 5B shows the middle position separation of the thumb 801 from the opposing long fingers 604. In all positions illustrated in FIGS. 5A, 5B and 5C, the thumb 801 is flexed and opposes the space 600 between the index finger 606 and middle finger 607 and the tips 610 of the long fingers 604 line up in substantially linear relation to preserve the finger cup 601 and palmar arch 102.

Figure 4B:
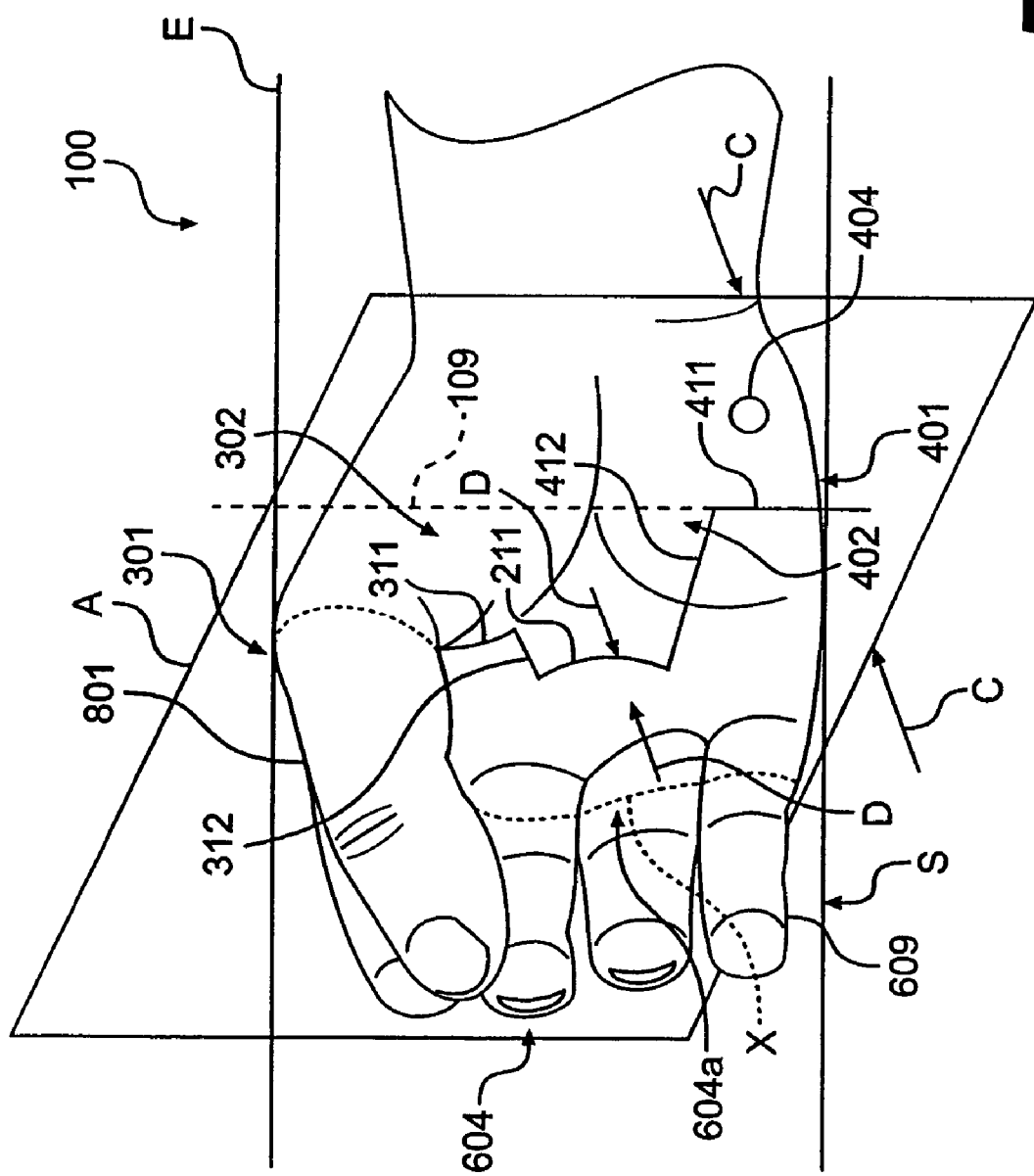

Referring to FIG. 4B with reference to FIGS. 5A, 5B and 5C, when the ulnar side 401 of the hand 100 rests on a flat surface S and the hand is in the 'T Position' Plane A falls perpendicular on a flat surface S of a table without touching the ulnar side 401 of the hand 100. Normally when a hand 100 lies flat on its dorsal surface (back) the thenar muscle area 302 is higher than the hypothenar muscle area 402 because the thenar muscle bulk is greater than the hypothenar muscle bulk. Plane A is substantially further away from the hypothenar muscle area 402 when the hand 100 rests on the ulnar side 401 of the small finger 609 while the hand 100 is in the 'T Position'. This is because the muscles of the thenar muscle area 302 push Plane A forward when the thumb 801 moves to oppose the long fingers 604 and the radial side 301 of the hand 100 tilts (pronates) towards the body.

Continuing with reference to FIG. 4B another plane indicated at a location between two arrows C can be passed perpendicular to surface S at a right angle to Plane A to meet the proximal horizontal ulnar line 109 of the ulnar side 401 of the hand 100 just distal the pisiform bone 404. The location where a handle or grip of the present invention last touches the hypothenar muscle area 402 is the another plane indicated at the location between the two arrows C meets the hypothenar muscle area 402 at the proximal horizontal ulnar line 109. The ulnar side of a handle, based on the above described design method of the present invention, may flare out to promote rotation of the radial side 301 of the hand 100 toward the body. This maintains the forearm in a neutral position, which is mildly rotated and places the radial side 301 of the hand 100 toward the body.

A third plane, indicated at a location between two arrows D, can be drawn from Plane A to the horizontal median line 211. This plane, indicated at the location between the two arrows D, demarcates the proximal position of the middle section of a handle of the present invention that touches the palm 100b of the hand 100.

Referring to FIG. 4B, the boundaries formed by the above described planes of FIG. 4B can be used to measure one half a handle of a design of the present invention when the hand is in the 'T Position' are determined by connecting four surfaces. Three surfaces are planar and one surface is curved. The first planar surface is formed by Plane A. The second planar surface is the plane formed by the surface S where the ulnar side 401 of the hand 100 rests. The third planar surface is formed by a plane indicated by E that touches the radial side 301 of the hand 100 in parallel relation to the surface S.

The fourth or curved surface is the inner surface of the hand 100 formed where Plane A intersects with inner surface 604a of the long fingers 604 indicated by the dotted line X, and with the radial horizontal line 311, and with the perpendicular plane extending from Plane A to the horizontal ulnar line 411 indicated by the arrows C, and with the third plane indicated by the arrows D perpendicular from Plane A to the middle horizontal line 211.

Since one hand 100 is the mirror image of the other hand 100, the surface or volume map for values for design data from the above described boundaries will reflect positive value data for one hand 100 and corresponding negative value data for the other hand 100 that is equal in absolute value to the corresponding positive value data. Adding the absolute values of the corresponding positive and negative data from the surface or volume map provides the dimensions for a handle of the design of the present invention that fits either hand 100 when either hand 100 is in the 'T Position'. Using the surface or volume map data provides information for designing a mold for a handle of the design or the present invention that fits either hand 100.

In addition, in the design method of the present invention, measurements of the palmar surface 100a as described above with respect to FIG. 4B desirably can be taken in three or more measurement positions using the three T positions as shown in FIGS. 5A, 5B and 5C, respectively. The first such measurements as discussed above with respect to FIG. 4B are taken with the tip 610 of the thumb 801 touching the space 600 between the index finger 606 and middle finger 607, such as for a small size handle (FIG. 5A). The second such measurements as discussed above with respect to FIG. 4B are taken with the tip 610 of the thumb 801 spread approximately half way from the tips 610 of the long fingers 604, such as for a medium size handle (FIG. 5B). The third such measurements as discussed above with respect to FIG. 4B are taken when the tip 610 of the thumb 801 is spread maximally from the tips 610 of the long fingers 604, such as for a large size handle (FIG. 5C). As can be seen in FIGS. 5A, 5B and 5C Plane A advances toward the tips 610 of the long fingers 604 when the thumb 801 and long fingers 604 spread apart. Therefore, since the shape of the curved surface 110 of the hand 100 formed from the inner surface 604a of the long fingers 604 and the palmar surface 100a is related to the spread of the thumb 801 from the long fingers 604 in the 'T Position', then the volumetric dimensions of the hand 100, as measured as discussed above with respect to FIG. 4B, in the 'T Position' also change. Thus, the shape of a particular embodiment of a handle of a design of the present invention is related to the spread of the thumb 801 from the long fingers 604.

Figure 17A:
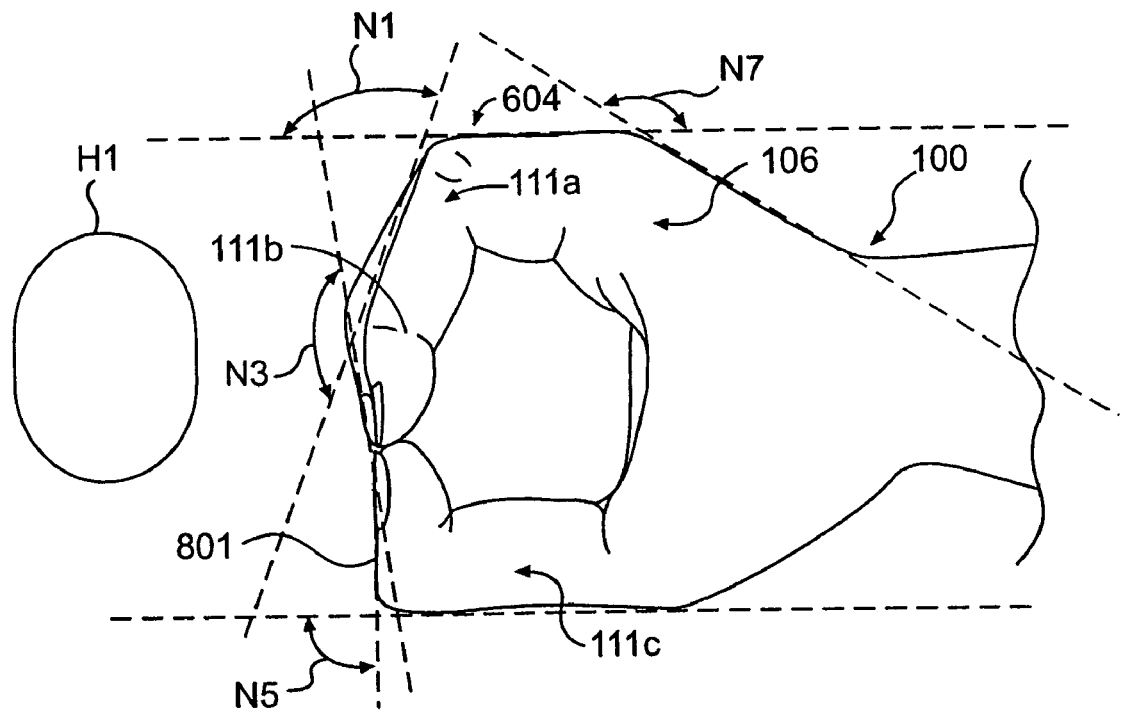
FIGS. 17A and 17B respectively illustrate radial profile views of handles produced from the handle design method based on the present invention, with FIG. 17A illustrating the fingers flexed and FIG. 17B illustrating the fingers extended.
Figure 17B:
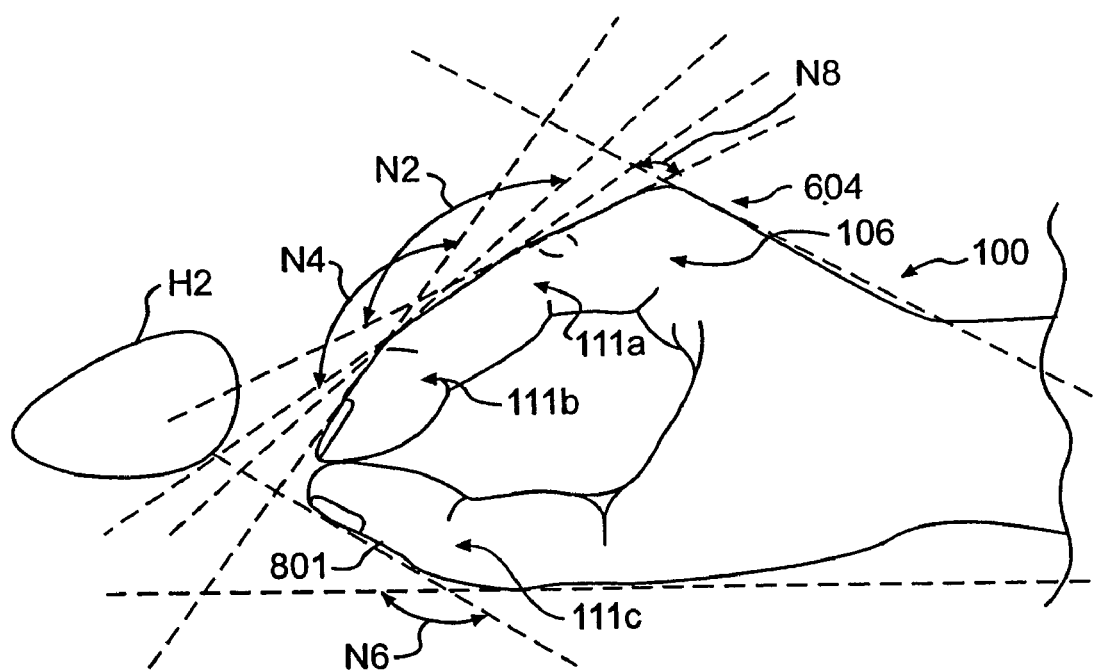

Continuing now with reference to FIGS. 17A and 17B, there is illustrated another determinant of the shape of various handles of the present invention utilizing the design method of the present invention based on the 'T Position'. This determinant is based upon the angular degree of flexion at the middle PIP joints 111a illustrated in FIG. 17A by the angle N1 and illustrated in FIG. 17B by the angle N2, and is based upon the angular degree of flexion at the distal PIP joints 111b of the long fingers 604 illustrated in FIG. 17A by the angle N3 and illustrated in FIG. 17B by the angle N4, and is based upon the angular degree of flexion at the distal PIP joint 111c of the thumb 801 illustrated in FIG. 17A by the angle N5 and illustrated in FIG. 17B by the angle N6, for the hand 100. Furthermore, this determinant is also based upon the angular degree of flexion at the MP joints 106 illustrated in FIG. 17A by the angle N7 and illustrated in FIG. 17B by the angle N8. Therefore, this other determinant provides for the shape of corresponding handles, such as handles H1 and H2, according to the design method of the present invention, based upon the angular degrees of flexion of the respective angles N1 through N8, which determine for the handles H1 and H2 the respective distances between the palmar part, the thumb part, the distal (front) part and proximal (rear) part of the handle.

In this regard, generally greater flexion at the middle PIP joints 111a produces a handle of the design method of the present invention that is shorter from the proximal (rear) part of a handle to the distal (frontal) part of a handle, such as handle H1 illustrated in FIG. 17A. As a corollary, generally less flexion at the middle MP joints 111a produces a handle of the design method of the present invention that is longer from the proximal (rear) part of a handle to the distal (frontal) part of a handle and longer from the palmar part to the thumb part of a handle, such as handle H2 illustrated in FIG. 17B. Also, handles designed by this method may be larger to compensate for skin and subcutaneous tissue compression.

Figure 18:
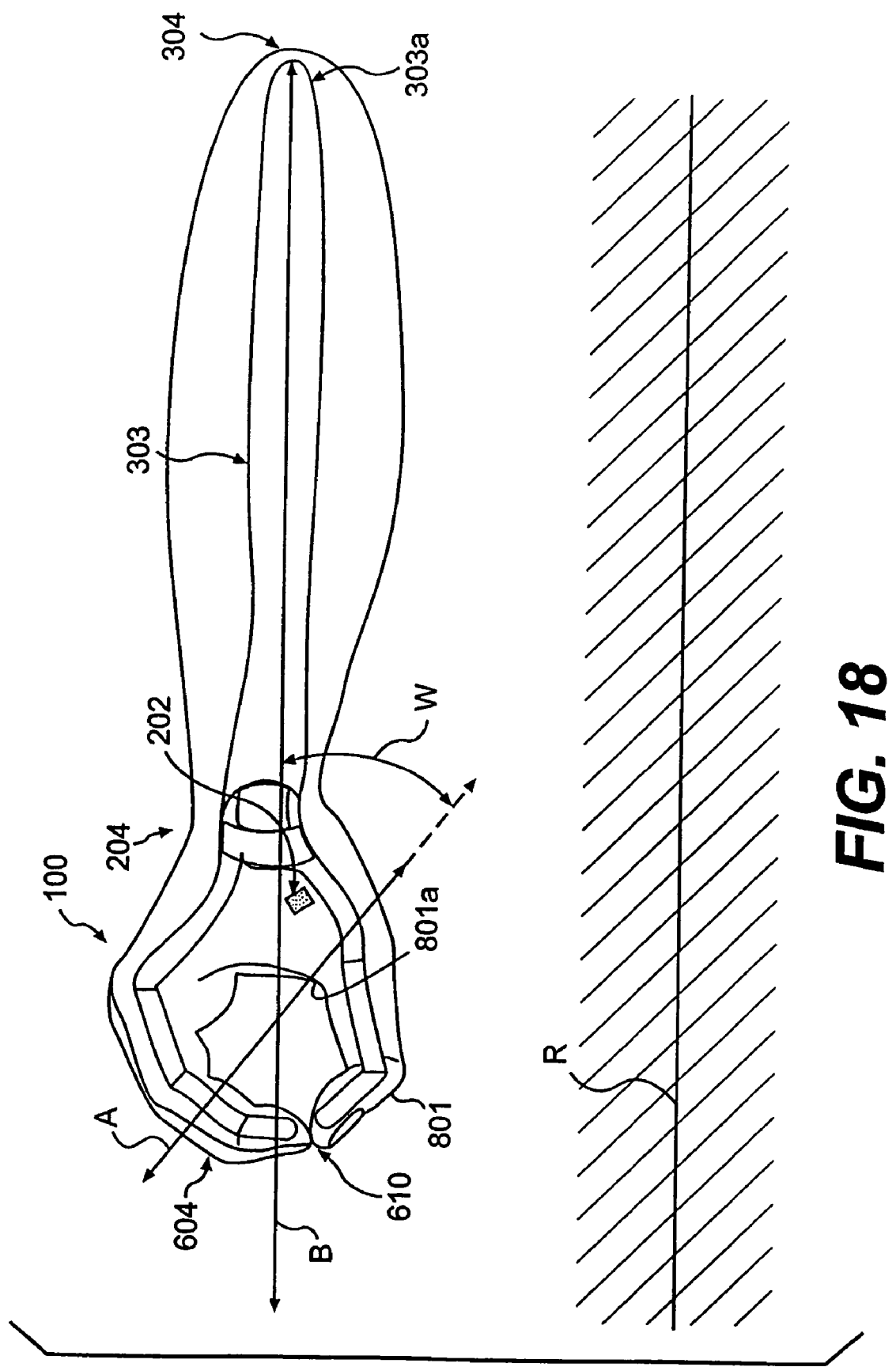
FIG. 18 shows the intersection of Plane A from the base of the thumb through the long fingers and Plane B which passes through the center of the radius bone in relation to the neutral wrist position for a hand using a handle of the present invention.

Referring now to FIG. 18, FIG. 18 illustrates a relation of the neutral wrist position for a hand using a handle of the present invention. FIG. 18 illustrates the intersection of Plane A, which passes from the base 801a of the thumb 801 through the long fingers 604 and Plane B, which passes through the center of the radius bone 303 from the elbow 304 to the wrist 204, which are used to determine the neutral wrist position.

Furthermore as illustrated in FIG. 18, Plane B travels through the center to the radius bone 303 from the olecranon 303a at the elbow 304 to extend through the wrist 204 deep to the distal part of the TCL 202 beyond the long fingers 604 when the wrist 204 is in a neutral position. The position where Plane B crosses the long fingers 604 when the wrist 204 is in a neutral position depends on the spread between the thumb 801 and long fingers 604, as illustrated in FIGS. 5A, 5B and 5C. Plane B meets the long fingers 604 closer to their fingertips 610 when the hand 100 is in the above described 'T Position' for a larger handle, based on the design method of the present invention.

Continuing with reference to FIG. 18, the angle W, between Plane A and Plane B, should desirably be between about 10 degrees and 40 degrees to maintain the wrist 204 in a neutral position when the hand 100 is in the 'T Position'. The angle W will be closer to 20 degrees when the thumb 801 and longer fingers 604 are spread and the angle W will be closer to 30 degrees when the thumb 801 is opposed to the long fingers 604.

The proper angular relationship between the two planes, Plane A and Plane B, should provide an optimal angle W promotes limiting wrist flexion and extension and promotes preventing kinks to the median nerve in the CT 203 while holding a handle of the present invention. This angular relationship generally can be ignored for small handles of the present invention because in this case the plane A and the plane B may coincide. However, the position of Plane A of a supportive type handle of the present invention, such as a bicycle type handle, will not necessarily be parallel to the ground or reference surface R.

Figure 19A:
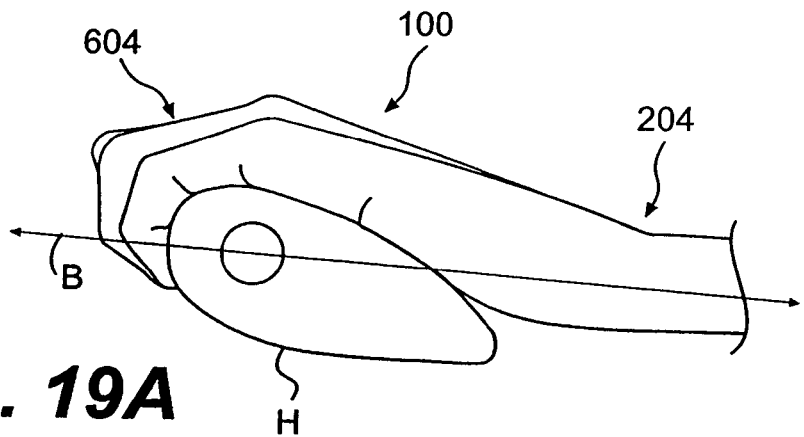
FIG. 19A shows the relationship of Plane A to Plane B from the ulnar side perspective of a hand holding a handle of one embodiment of the present invention.
Figure 19B:
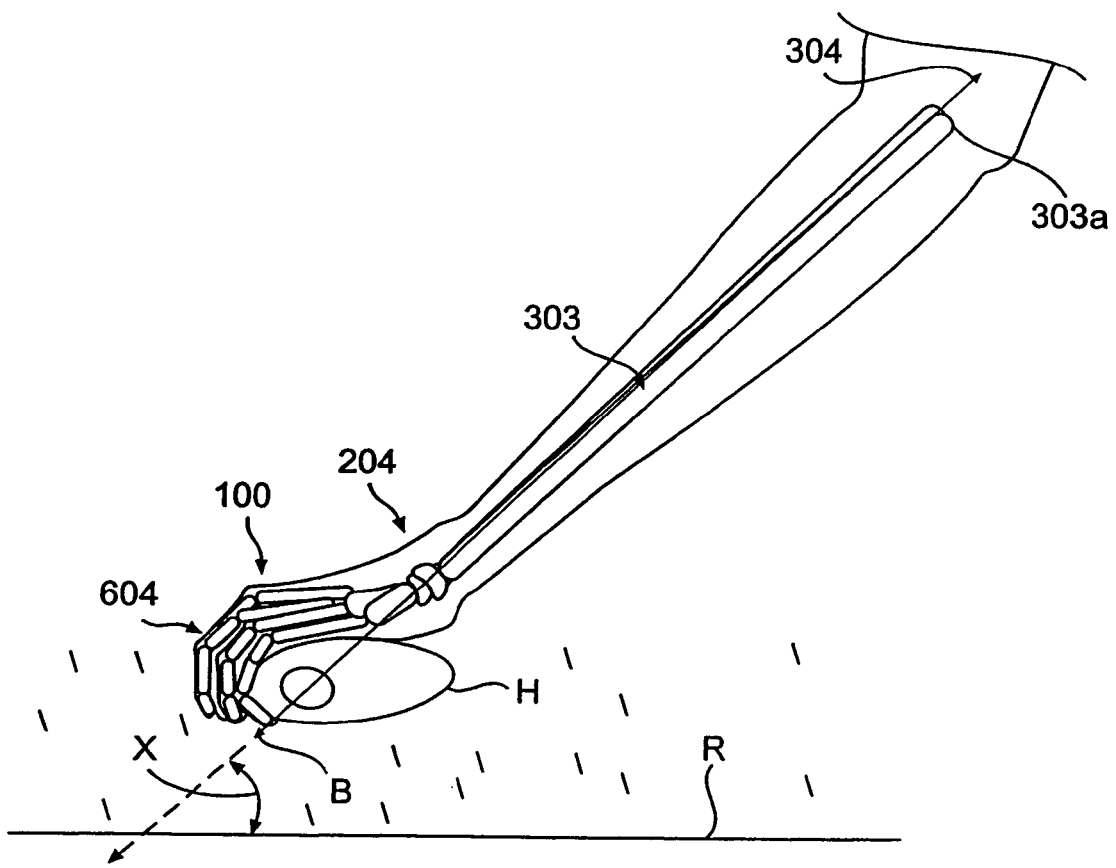
FIG. 19B shows the relationship of Plane A to Plane B from the ulnar side of the hand when the hand is resting on a handle of the present invention and the wrist is in the neutral position.

Referring now to FIGS. 19A and 19B, the position of such a handle, such as handle H, depends on the angle Plane B makes with the ground or reference surface R. As illustrated in FIGS. 19A and 19B the more vertical the angle X that Plane B makes with the ground or the reference surface R, the higher the proximal part of the handle H will be positioned with respect to the ground or the reference surface R. Therefore, a handle of the design method of the present invention when used as a supportive type handle, should be positioned so that the angle W between Plane A and Plane B, as described above with respect to FIG. 18, maintains the wrist 204 in the neutral position according to the angle Plane B, within the user's forearm 103, makes with the ground or reference surface R.

Figure 9A:
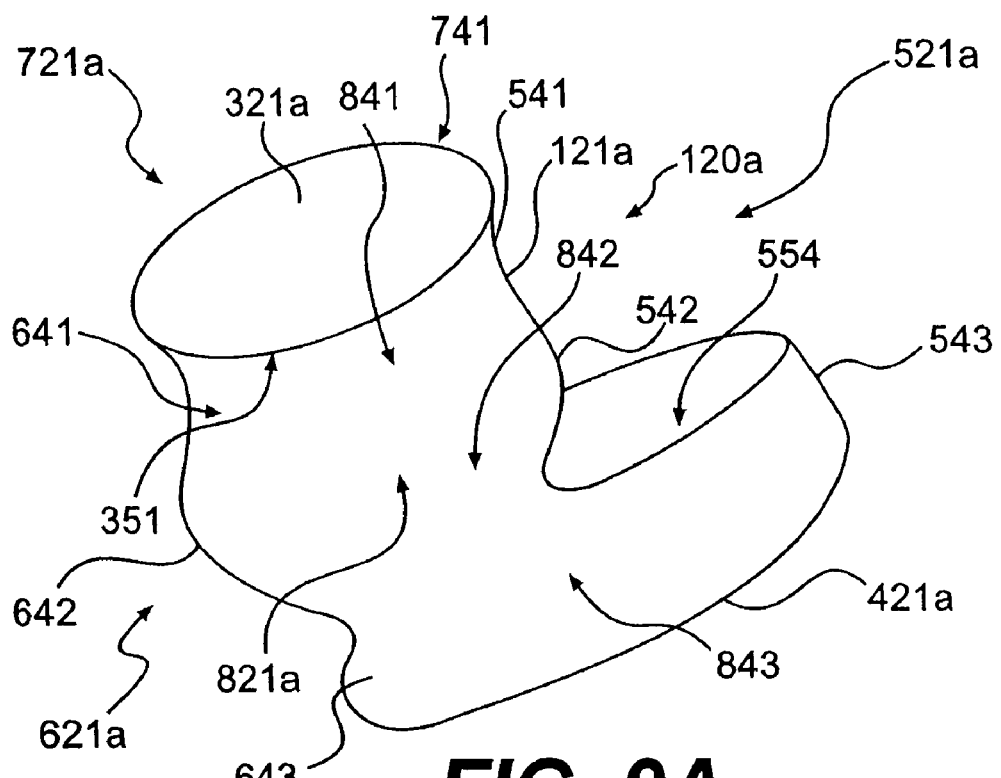
FIGS. 9A and 9B are perspective views of two exemplary embodiments of handles according to the present invention.
Figure 9B:
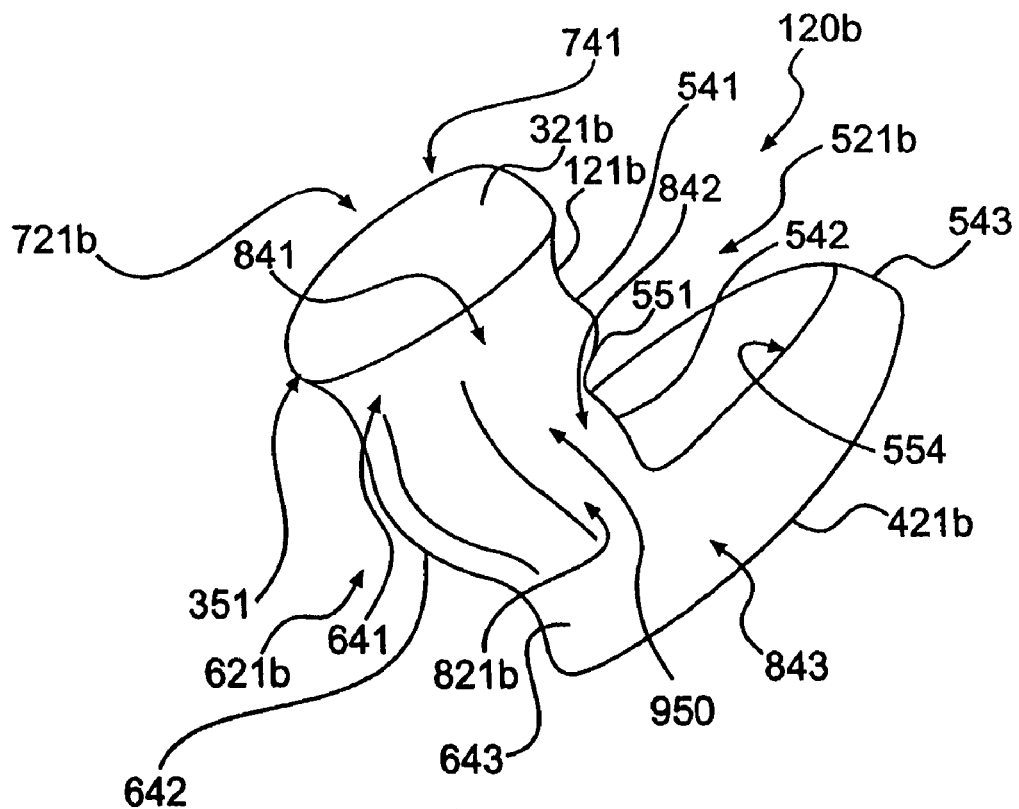

Various embodiments of handles according to the present invention will now be described first with reference the body structure shown in FIGS. 9A, 9B, 10A-10D and 11A-11C, with FIG. 9A illustrating an embodiment of a handle 120a and FIG. 9B illustrating an embodiment of a handle 120b. Handle 120a is illustrative of a handle formed when the thumb 801 and long fingers 604 are spread apart such as illustrated in FIGS. 5B and 5C, and handle 120b is illustrative of a handle formed when the thumb 801 and long fingers 604 are touching such as illustrated in FIG. 5A.

The body 121a, 121b of a handle 120a, 120b of this design is made of free-formed curves and shaped like a boot and is shown in FIGS. 9A, 9B, 10A-10D and 11A-11C.

The body 121a, 121b of a handle 120a, 120b of this design shown in FIGS. 9A, 9B, 10A-10D and 11A-11C, has an elongated body and has a radial side 321a, 321b and an ulnar side 421a, 421b of a handle of this design.

The body 121a, 121b of a handle 120a, 120b of this design has four parts as shown in FIGS. 9A, 9B, 10A-10D and 11A-11C. The proximal (rear) part 521a, 521b of body 121a, 121b, the palmar part 721a, 721b, the distal (front) part 621a, 621b and the thumb part 821a, 821b of body 121a, 121b of handle 120a, 120b. Each of these parts of the handle 120a, 120b is contiguous with a corresponding adjacent part of the handle 120a, 120b.

The proximal (rear) part 521a, 521b of body 121a, 121b is defined to correspond to the proximal horizontal radial line 108 at the base 801a of the thumb 801 to the horizontal creases 101 at the radial side 301 of the hand 100 as illustrated in FIGS. 1 and 6.

The palmar part 721a, 721b of body 121a, 121b is designed to extend from the horizontal creases 101 of the hand 100 distally to the proximal finger creases 603 of the long fingers 604 as illustrated in FIGS. 1 and 6.

The distal (frontal) part 621a, 621b of body 121a, 121b is designed to extend from the proximal finger creases 603 to the tips 610 of the long fingers 606, 607, 608 and 609.

The thumb part 821a, 821b of body 121a, 121b is designed to extend from the proximal horizontal radial line 108 at the base 801a of the thumb 801 to the tips 610 of the long fingers 604 when the hand 100 is in the 'T Position'.

Figure 12:
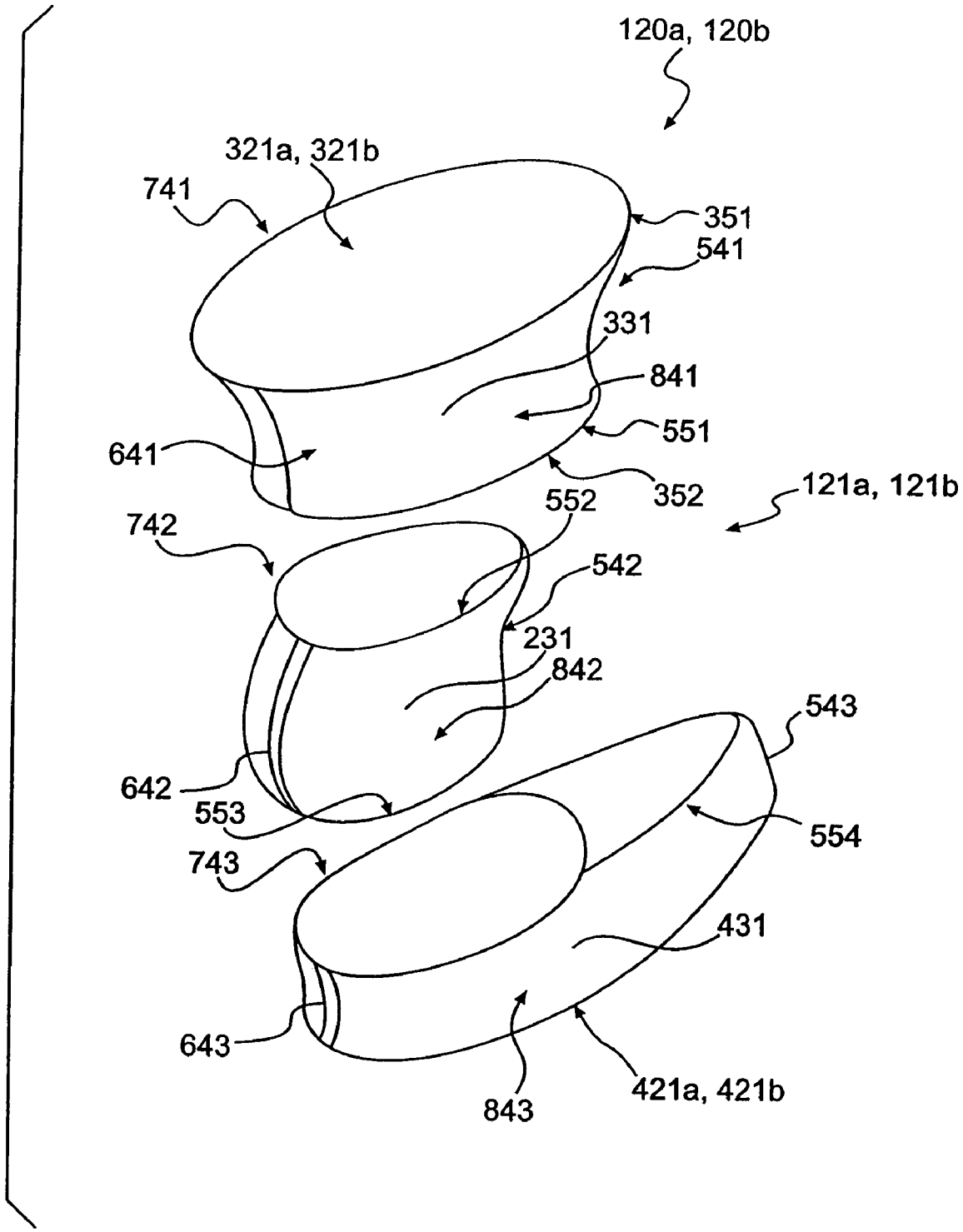
FIG. 12 illustrates the body of an embodiment of the handle of FIG. 2 of the present invention divided into a radial section, a middle section and an ulnar section.

The body 121a, 121b of a handle 120a, 120b of this design can be divided into three contiguous sections, which are the radial section 331, the middle section 231 and the ulnar section 431, arranged from the radial side 321a, 321b to ulnar side 421a, 421b as particularly shown in FIG. 12 as well as indicated in FIGS. 9A-10D. The radial section 331 is somewhat oval in shape and can have a wide hourglass or concave shape extending from its radial side edge 351 to its ulnar edge 352 of the radial section 331. The middle section 231 is somewhat oval with a curved outer surface conforming to the shape of the hand 100 in the 'T Position'. The proximal (rear) side 543 of the ulnar section 431 has a generally triangular curved shape similar to the shape of a pointed shoe and at its distal (frontal) side 643 is generally oval shaped similar to the shape of the back of a heel of a shoe. The distal (frontal) side 643 of the ulnar section 431 has a smaller radius from its center than the radius from the center of the distal (frontal) side 641 of the radial section 331.

The radial section 331 is in corresponding relation to the radial side 301 of the hand 100, which includes the index finger 606, thenar muscle area 302, the metacarpal joint 106 related to the index finger 606 and the thumb 801. The middle section 231 is in corresponding relation to the middle finger 607 and ring finger 608 and their corresponding metacarpal joints 106 at the palm 100b. The ulnar section 431 is in corresponding relation to the small finger 609 and the hypothenar muscle area 102 of the hand 100.

The sections 231, 331, 431 each have proximal, palmar, distal and thumb sides. The radial section 331 has a proximal (rear) side 541, a palmar radial side 741, a distal (frontal) radial side 641 and a thumb radial side 841. The middle section 231 has a proximal (rear) side 542, a palmar middle side 742, a distal (frontal) middle side 642 and a thumb middle side 842. The ulnar section 431 has a proximal side 543, a palmar ulnar side 743, a distal (frontal) ulnar side 643 and a thumb ulnar side 843.

The body 121a, 121b of a handle 120a, 120b can have edges along various surfaces, which are illustrated in FIGS. 9A-12.

The radial section 331 can have a radial side edge 351 at the radial end side 321a, 321b of the radial section 331 of the elongated body 121a, 121b. The radial section 331 can also have an ulnar edge 551 adjacent the proximal radial side 541.

The middle section 231 can have a radial side edge 552 adjacent its proximal middle side 542 where the middle section 231 meets the radial section 331. The middle section 231 can have an ulnar edge 553 where the middle section 231 meets the ulnar section 431.

The ulnar section 431 can have a radial edge 554 adjacent its proximal ulnar side 543 and another edge the along the ulnar end side 421a, 421b of the ulnar section 431 of the elongated body 121a, 121b.

Figure 10A:
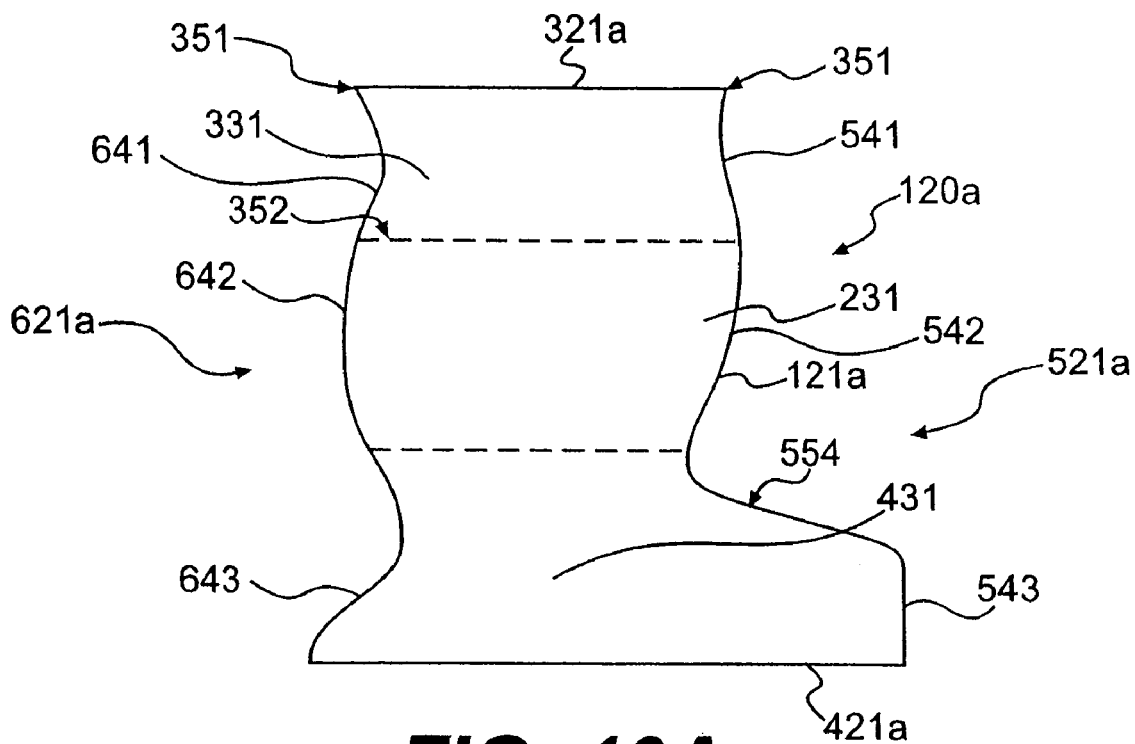
FIGS. 10A and 10B are respectively side views of two exemplary embodiments of FIGS. 9A and 9B, and FIGS. 10C and 10D are respectively a distal (front) view and a proximal (rear) view of the embodiment of the handle of FIG. 9A.
Figure 10B:
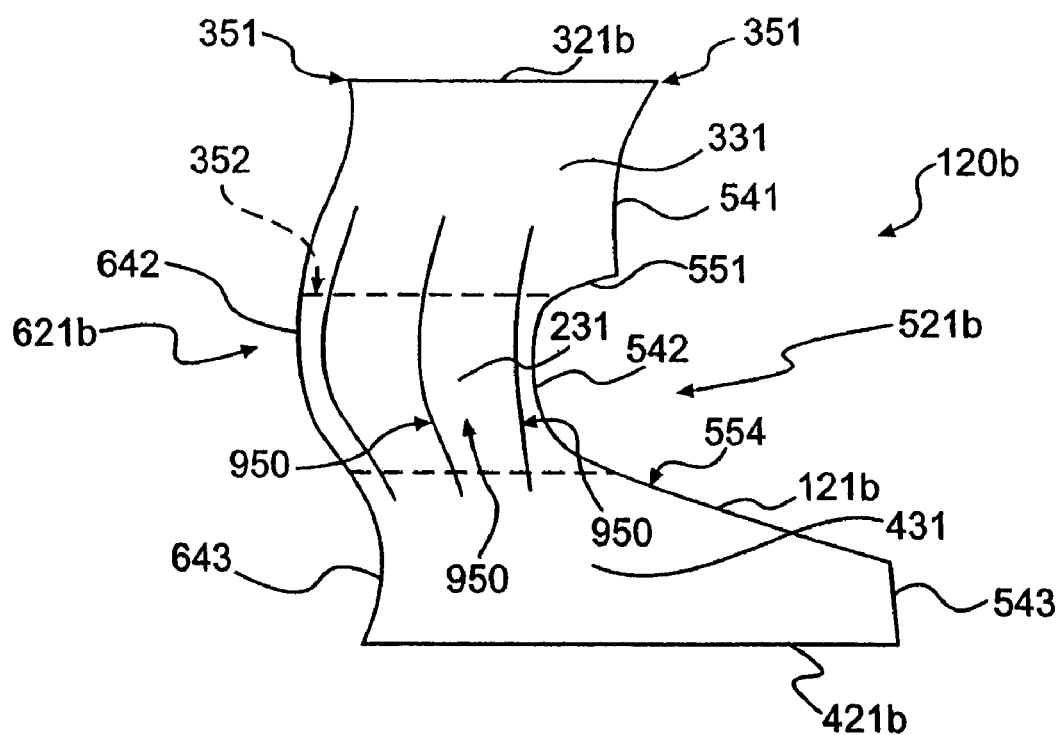
Figure 10C:
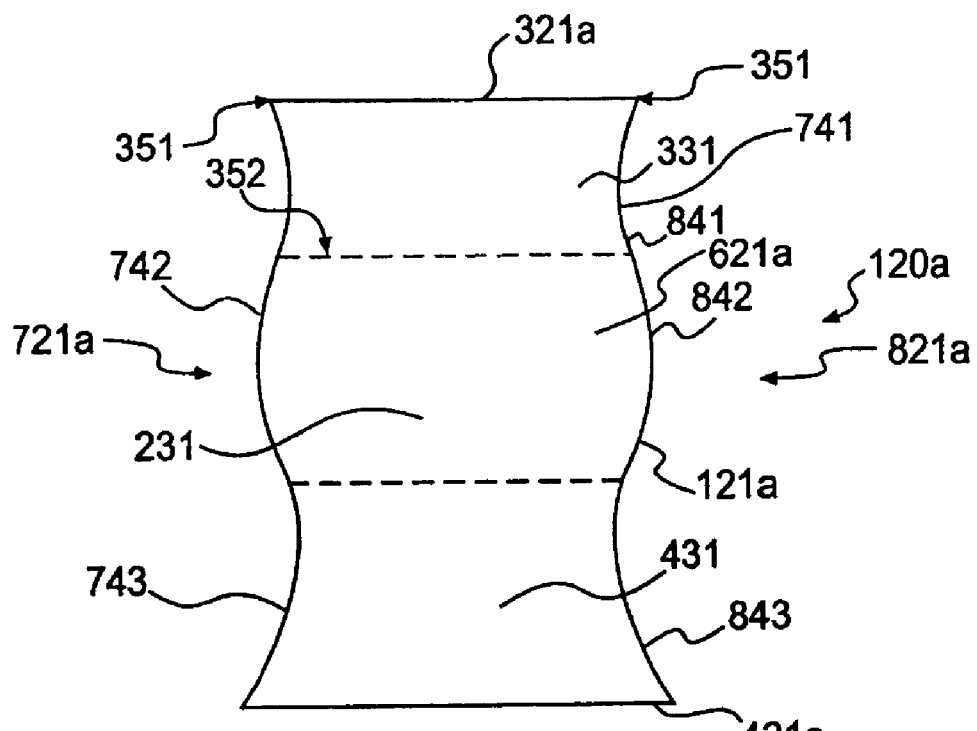
Figure 10D:
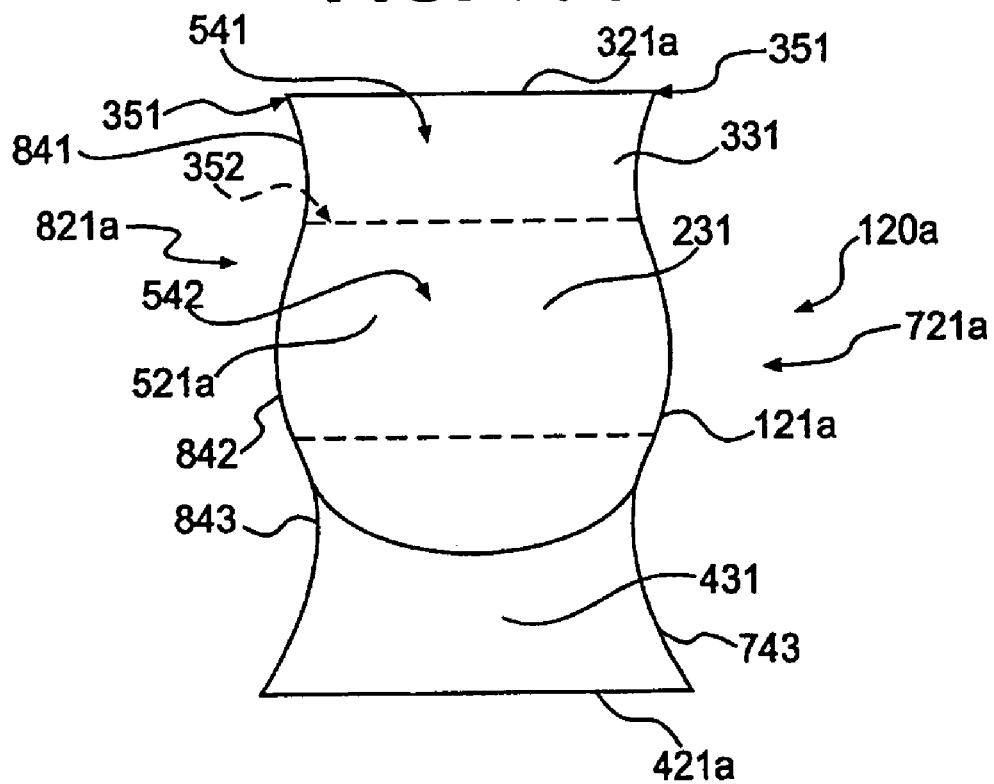
Figure 11A:
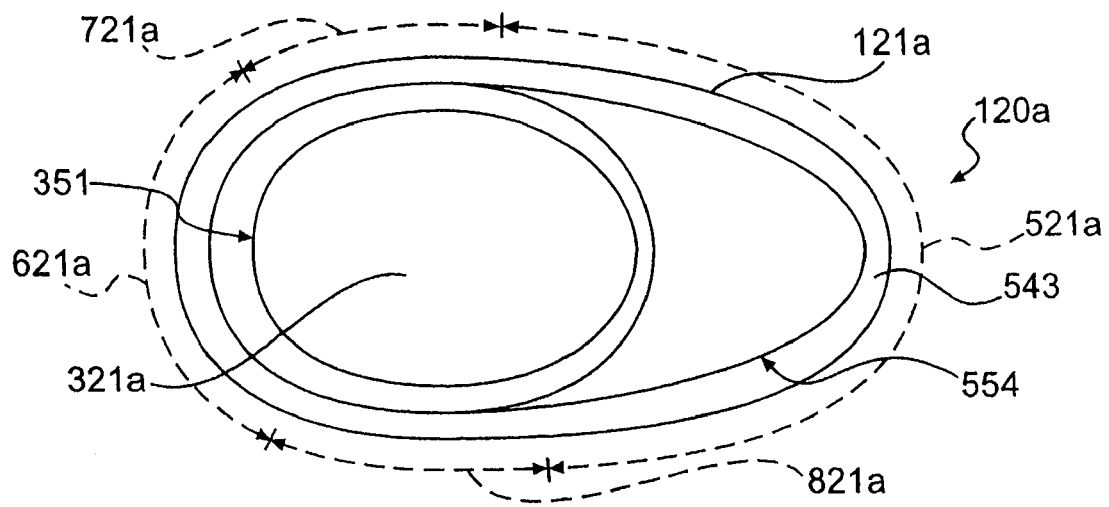
FIGS. 11A, 11B and 11C are profile views, with FIGS. 11A and 11B respectively illustrating radial (top) views of the two exemplary embodiments of FIGS. 9A and 9B, and with FIG. 11C illustrating an ulnar (bottom) view of the handles of FIGS. 9A and 9B of the present invention.
Figure 11B:
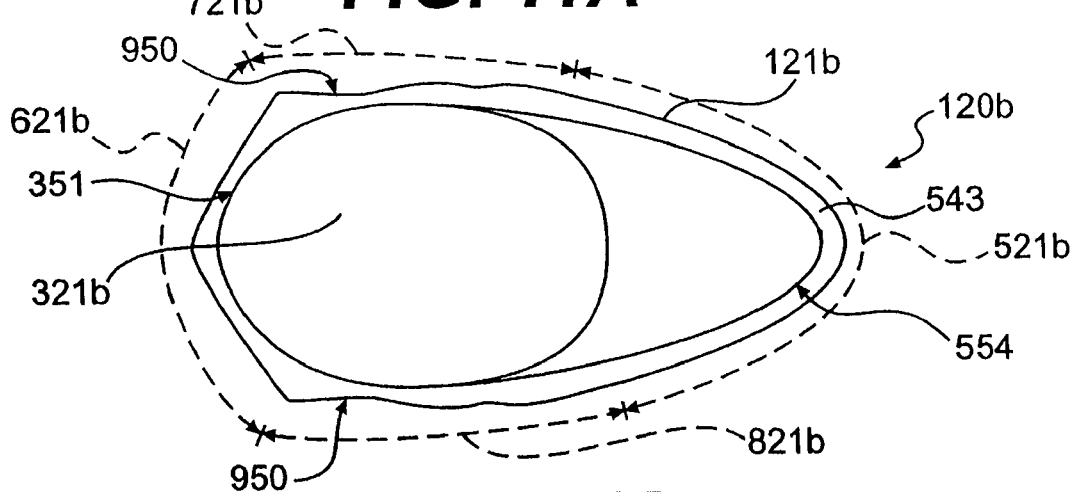
Figure 11C:
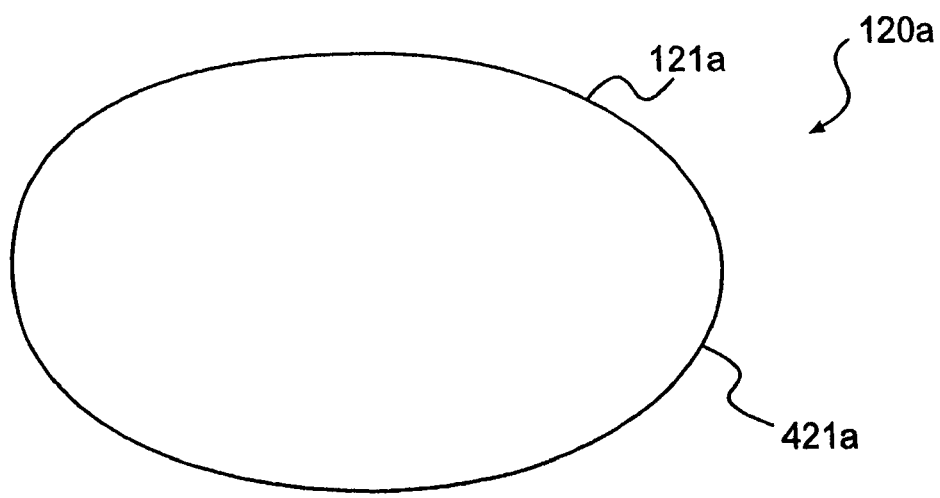

Referring to and as illustrated in FIGS. 9B, 10B and 11B, the body 121a, 121b of handle 120a, 120b, can include a grooved or flattened portion 950 extending on at least the palmar middle side 742 of the middle section 231 of the body 120a, 120b, and the grooved or flattened portion 950 can also extend on either or both of the palmar radial side 741 of the radial section 331 and the palmar ulnar side 743 of the ulnar section 431 of the body 121a, 121b. The grooved or flattened portion 950 forms a rest for receiving the MP joints 106 of the hand 100 when the hand 100 is engaged with the body 121a, 121b of the handle 120a, 120b.

Further, in the handle 120a, 120b of FIGS. 9A through 12, as discussed herein the shape of the ulnar contact area can be concave, flat or convex depending upon the application of the handle. Also, the radial edge of the ulnar section may form a lip or ridge that extends into the ulnar side of the palm. This may stabilize the ulnar side of the hand and prevent it from slipping, such variation can be useful for bicycle handgrips, for example. Additionally, while the radial edge of the ulnar section can appear horizontal, but where contact of the ulnar section is made with the hypothenar muscle area, such contact of the ulnar section will be in the shape of a wedge.

Also, in the handle 120a, 120b of FIGS. 9A through 12, variations can occur at various parts of the handle. For example, the surface where the long fingers 604 end on the thumb side can be round, flat or depressed or have multiple depressions. Further, the area where the thumb 801 contacts the thumb side of handle 120a, 120b, can be round, flat or depressed.

Additionally, in the handle 120a, 120b of FIGS. 9A through 12, there can be variations including a frontal elevation that act as a reference area for the middle finger creases, and a depression formed in the palmar side of the handle can act as a reference area for the width across the metacarpal bones.

Figure 13A:
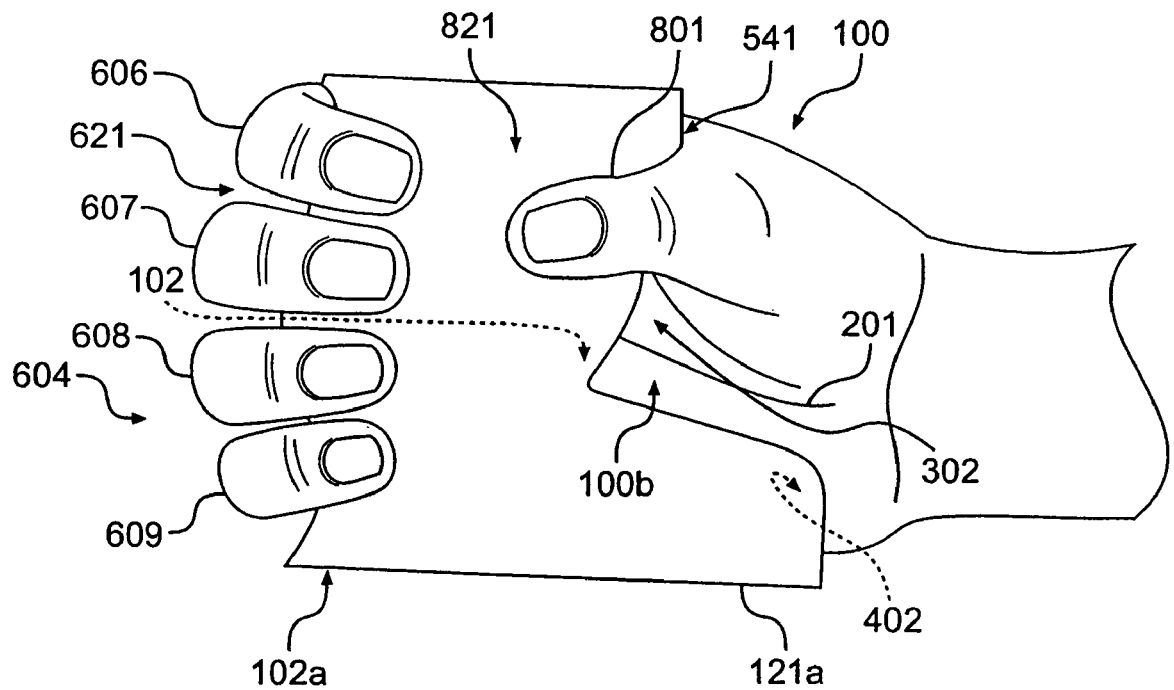
FIGS. 13A and 13B respectively illustrate a side view and a distal (front) view of the handle illustrated in FIG. 9A, with the hand engaging the handle according to the present invention.
Figure 13B:
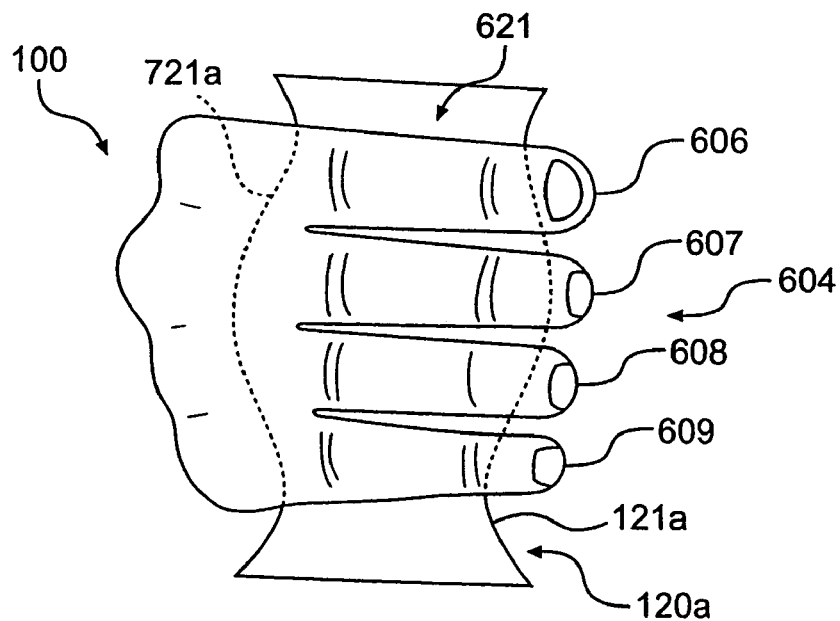

FIGS. 13A and 13B illustrate the right hand 100 wrapping around a handle 120a of FIG. 9A. The proximal (rear) side 541 of the body 121a of a handle 120a contacts the thenar muscle area 302 and hypothenar muscle area 402 but does not contact the longitudinal crease 201 of the palm 100b. The palm 100b and palmar arch 102 contact the palmar part 721a of the body 121a of the handle 120a. The long fingers 604 come around to contact the distal (front) part 621 of the body 121a of a handle 120a. The thumb 801 contacts the thumb part 821 of the body 121 of the handle 120a.

Figure 14A:
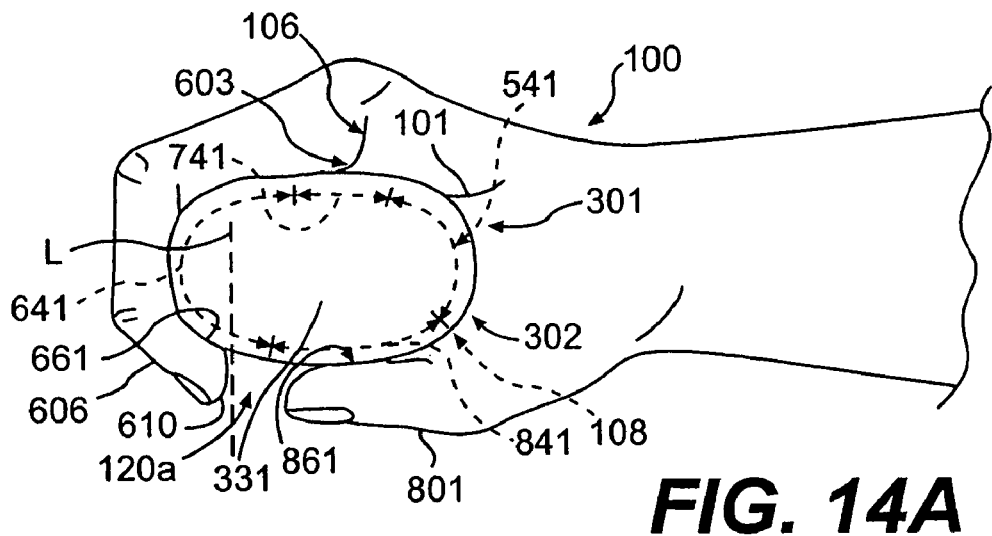
FIGS. 14A, 14B and 14C respectively illustrate the radial, middle and ulnar sections of a handle of the present invention engaging a corresponding region of the hand.
Figure 14B:
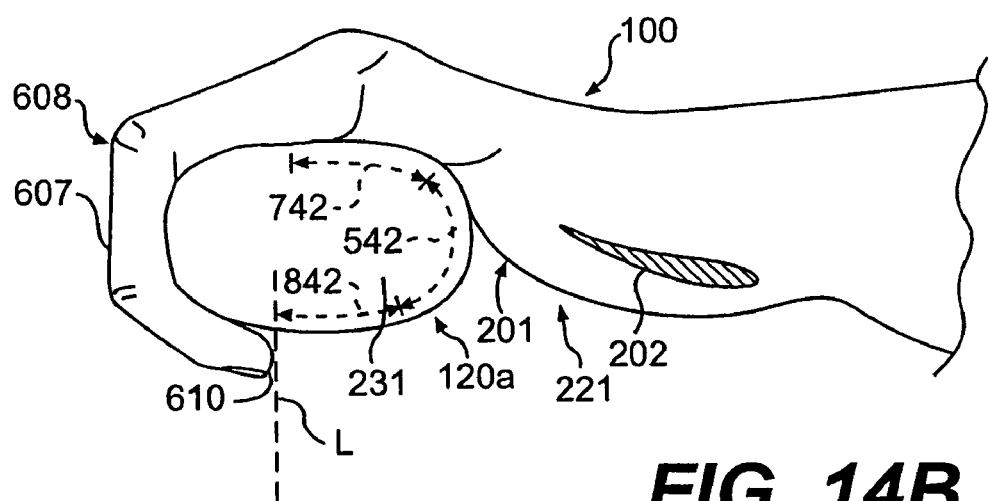
Figure 14C:
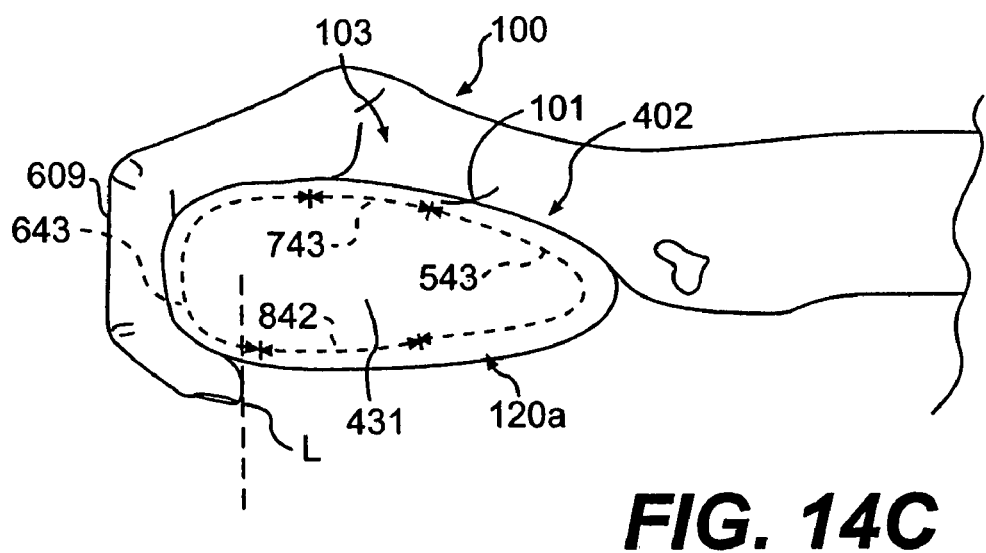

The relationship of the radial 331, middle 231 and ulnar 431 sections of a handle 120a to the parts or the hand 100 are shown in FIGS. 14A, 14B and 14C. FIG. 14A shows the radial side 301 of the hand 100 contacting the radial section 331 of a handle 120a. The thenar muscle area 302 contacts the proximal (rear) side 541 of the radial section 331 from the proximal or radial horizontal line 108 to the horizontal palmar crease 101 on the hand 100. The metacarpal joint 103 of the index finger 606 contacts the palmar radial side 741 of the radial section 331 from the horizontal palmar crease 101 to the proximal finger crease 603. The index finger 606 contacts the distal (frontal) side 641 of the radial section 331 from the proximal index finger crease 603 to the fingertip 610 to end at the index finger rest position 661 in the radial section 331. The thumb 801 contacts the thumb radial side 841 of the radial section 331 at the thumb contact position 861 so that the thumb 801 rests in the area near the ulnar side of the radial section 331.

FIG. 14B illustrates the relationship of the middle section 231 of the longitudinal crease 201 and the TCL 202 of the hand 100 do not contact the proximal middle side 542 of the middle section 231. This produces a median void 221 for a handle 120a. The metacarpal joints 103 of the middle finger 607 and ring finger 608 contact the middle palmar side 742 of the middle section 231 at the palmar arch 102. The middle finger 607 and ring finger 608 contact the bulge of the distal (frontal) middle side 742 of the middle section 231. The tips 610 of the middle finger 607 and ring finger 608 end at the same line L as the index finger 606 in the radial section 331. There is no contact of the hand 100 on the thumb side 842 of the middle section 231.

FIG. 14C illustrates the relationship of the ulnar section 431 of handle 120a to the hand 100.

The hypothenar muscle area 402 of the hand 100 contacts the proximal ulnar side 543 of the ulnar section 431 of a handle of this design up to the ulnar side of the horizontal creases 101.

The metacarpal joint 103 of the small finger 609 contacts the palmar ulnar side 743 of the ulnar section 431 of handle 120a. The distal (frontal) ulnar side 643 of the ulnar section 431 contacts the small finger 609. The small finger 609 contacts the concave section of the distal ulnar side 643 and ends at the same line L as the long fingers 606, 607, 608 that wrap around the radial section 331 and the middle section 231. There is no contact with the hand 100 on the thumb side 842 of the ulnar section 431.

The body 121a, 121b of a handle 120a, 120b can have edges along various surfaces that are related to various parts of the hand 100. The corresponding edges of the handle 120a, 120b have been discussed previously with respect to FIGS. 9A through 12, and respectively correlate with corresponding portions of hand 100 as illustrated FIGS. 7 and 8.

Referring to FIGS. 9A through FIG. 12 and to FIG. 7 and FIG. 8, The radial side edge 351 at the radial side 321 of a handle 121a is near the radial side 301 of the hand 100. The proximal ulnar edge 551 at the end of the radial section 331 contacts the hand 100 at the longitudinal radial line 312.

The proximal middle section radial edge 552 does not contact the hand 100 but is the radial boundary for the median void 221 of a handle 120a, 120b. The proximal middle section ulnar edge 553 does not contact the hand 100 but is the ulnar boundary for the median void 221 of handle 120a, 120b.

The ulnar section 431 can have an edge 554 along its proximal radial side that meets the longitudinal ulnar line 412. The ulnar section 431 has another edge 421a, 421b where it meets the ulnar side 401 of the hand 100.

Also, FIG. 8 shows the supported areas S indicated by the asterisks, "*", of handle 120a, 120b in relation to the palmar surface 100a of hand 100 in the 'T Position'.

Figure 15A:
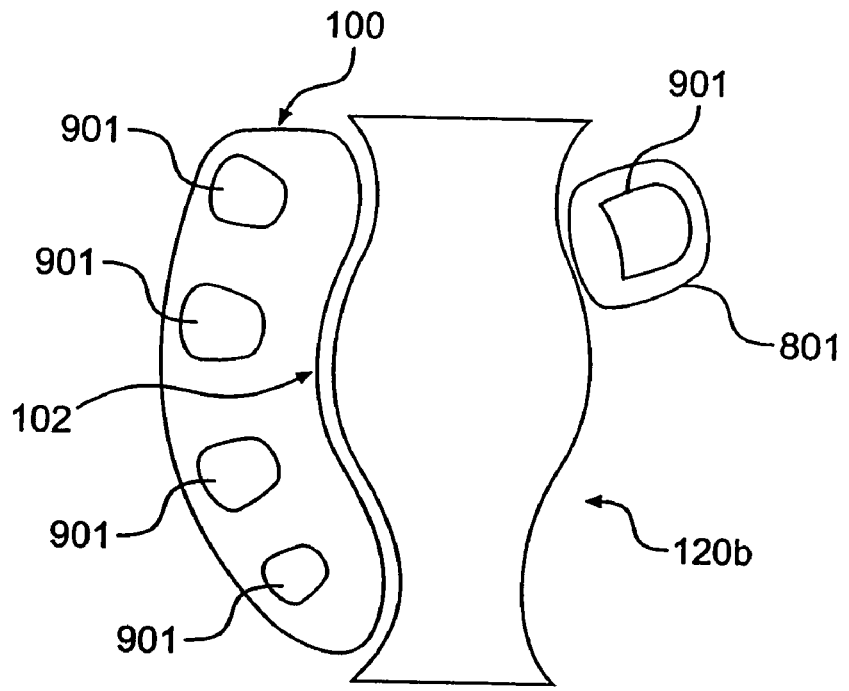
FIGS. 15A and 15B are cross-sectional views showing an embodiment of a handle of the present invention, with FIG. 15A illustrating a relationship of the metacarpal bones and palm to the distal phalange of the thumb and with FIG. 15B illustrating a relationship of the long fingers and proximal phalange of the thumb.
Figure 15B:
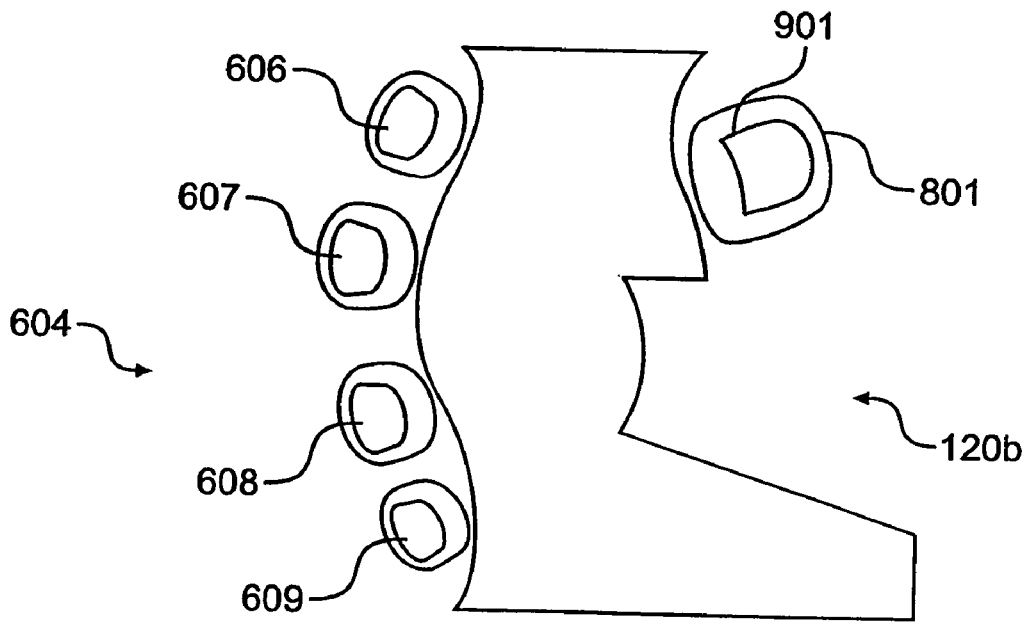

Moreover, FIGS. 15A and 15B are cross-sectional views showing handle 120b of FIG. 9B, with FIG. 15A illustrating a relationship of the metacarpal bones 901 and palm arch 102 to the metacarpal bone 901 of the thumb 801, and with FIG. 15B illustrating a relationship of the long fingers 606, 607, 608 and 609 and the metacarpal bone 901 the thumb 801.

As mentioned previously, the present invention provides a design method and apparatus for a handle or grip providing a shape and structure that fills various regions of the hand except a region in an area over the underlying carpal tunnel. Such design method and apparatus provides for various supports, handles, implements and tools for use by a hand.

Figure 16A:
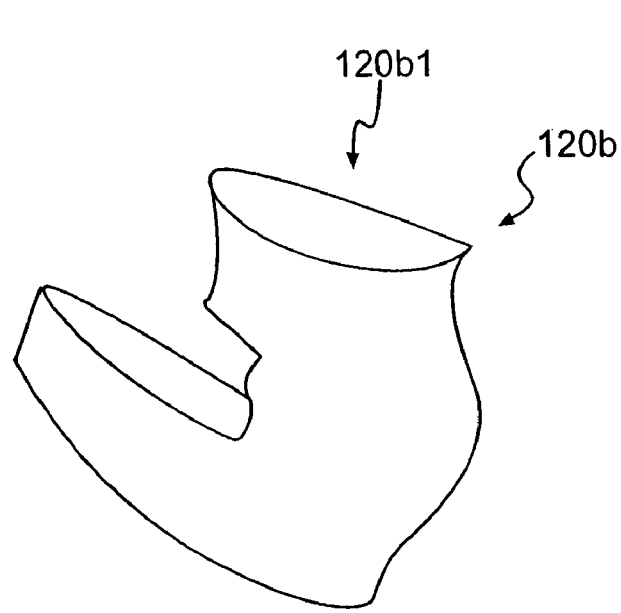
FIGS. 16A, 16B, 16C and 16D respectively illustrate four views of a handle in an embodiment of the present invention, bisected or split with FIG. 16A representing the right half of such a handle, with FIG. 16B representing the left half of such a handle, with FIG. 16C representing the distal (front) portion of such a handle, and with FIG. 16D representing the proximal (rear) portion as such a handle of the present invention.
Figure 16B:
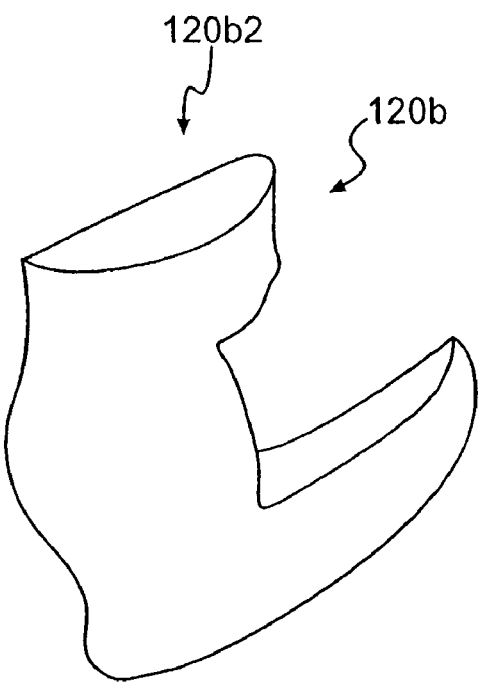
Figure 16C:
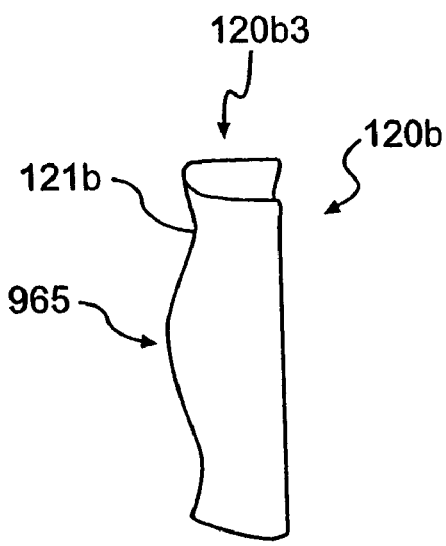
Figure 16D:
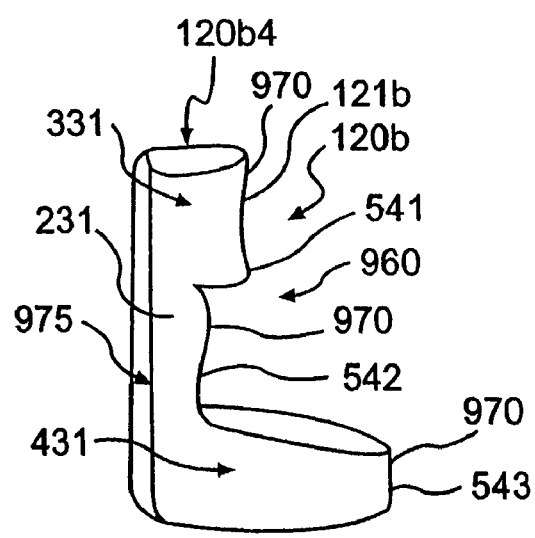

For example FIGS. 16A, 16B, 16C and 16D respectively illustrate four views of handle 120b of FIG. 9B that are bisected or split in two half sections, with FIG. 16A representing the right half section 120b1 of handle 120b, with FIG. 16B representing the left half section 120b2 of handle 120b, with FIG. 16C representing the distal (front) half section 120b3 of handle 120b, and with FIG. 16D representing the proximal (rear) section 120b4 of handle 120b. Such bisected half sections are useful in various implements and tools. Such bisected half sections, such as bisected half section 120b4, also can be used to extend from a door or to be used for pushing or sliding an object.

Figure 31:
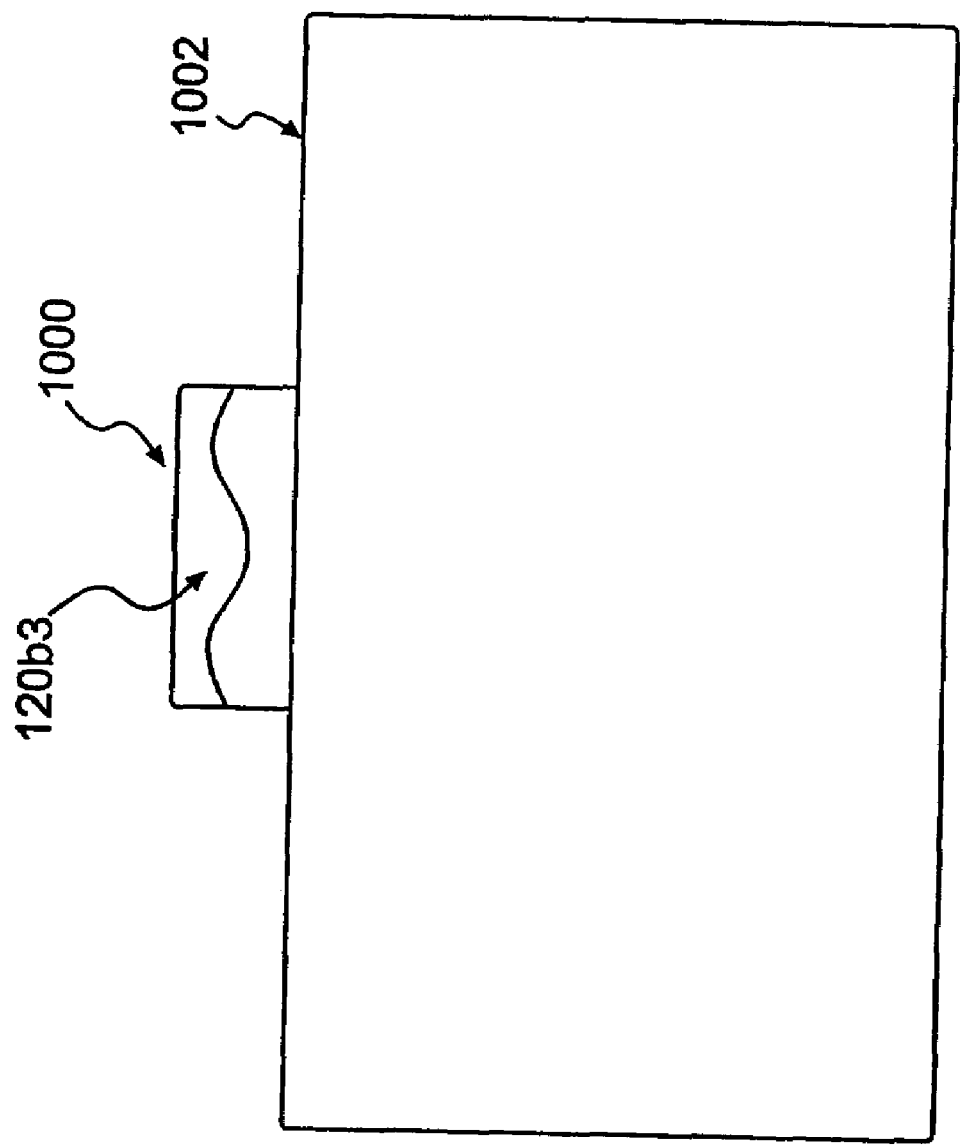
FIG. 31 illustrates another embodiment for a handle of the present invention for use as a luggage pull or handle for a case.

For example, FIG. 31 illustrates a luggage handle or pull 1000 for a case or luggage 1002 utilizing the distal half section 120b3 of FIG. 16C. Another example, illustrated in FIG. 22E illustrates a hinged tool, such as a stapler 1004, which combines section 120b3 and section 120b4 of FIG. 16C and FIG. 16D at a hinge 1006 at the radial end with the stapling mechanism 1008 for dispensing staples 1010 at the ulnar end.

Further, in addition to being useful in various implements and tools, the bisected handle 120b in FIGS. 16C and 16D can be used as an example to illustrate a feature of a handle or apparatus of the present invention. FIGS. 16C and 16D illustrate the handle 120b being longitudinally bisectionally defined and having a proximal side section 960 and a distal side section 965. The proximal side section 960 of the elongated body 121b of the handle 120b forms a proximal side surface 970 that includes the proximal radial side 541 of the radial section 331, the proximal middle side 542 of the middle section 231 and the proximal ulnar side 543 of the ulnar section 431. As illustrated in FIG. 16D, from a position 975 on the handle 120b where the handle is longitudinally bisectionally defined into the proximal side section 960 and the distal side section 965, the proximal ulnar side 543 of the ulnar section 431 extends beyond the proximal middle side 542 of the middle section 231. Such feature, as illustrated in FIGS. 16C and 16D, is useful in the various embodiments of handles or apparatus of the present invention when engaging a corresponding portion of the palmar surface of the hand to position the handle within the hand without engaging or placing substantial pressure on a surface of the hand located over the carpal tunnel or without creating substantial pressure within the carpal tunnel.

Figure 22C:
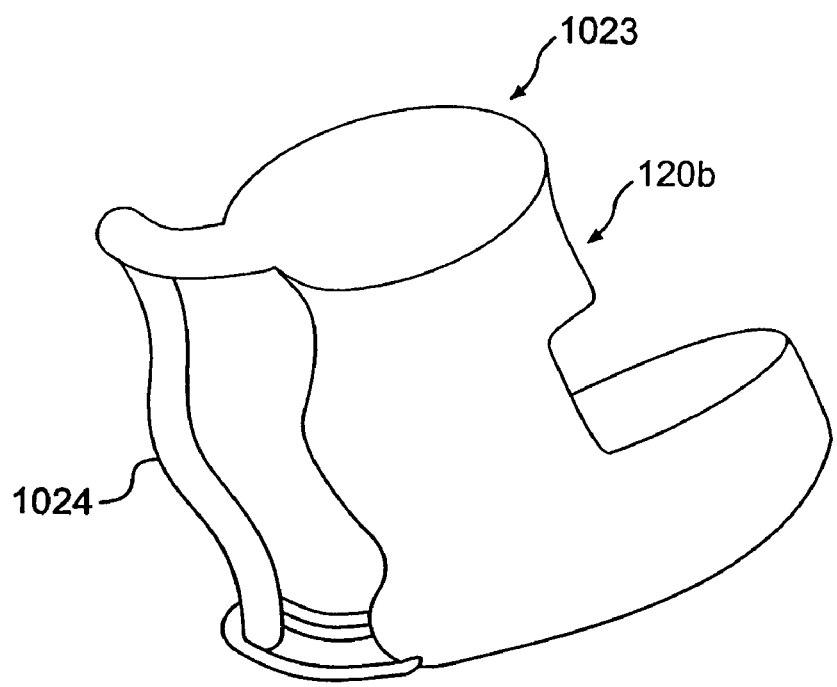
FIGS. 22A-22E illustrate various embodiments of handles of the present invention used as squeezing devices, with FIG. 22A illustrating a side view of a hand brake, with FIG. 22B illustrating the distal (front) view of the hand brake, with FIG. 22C illustrating a perspective view and FIG. 22D illustrating a perspective view of the hand engaging the hand brake of FIG. 22A, and with FIG. 22E illustrating an example of a handle of the present invention with a hinged end, such as for use as a stapler, and FIG. 22F illustrating an example of a handle of the present invention including tracks with springs, such as for use as a hand exercise machine.
Figure 22D:
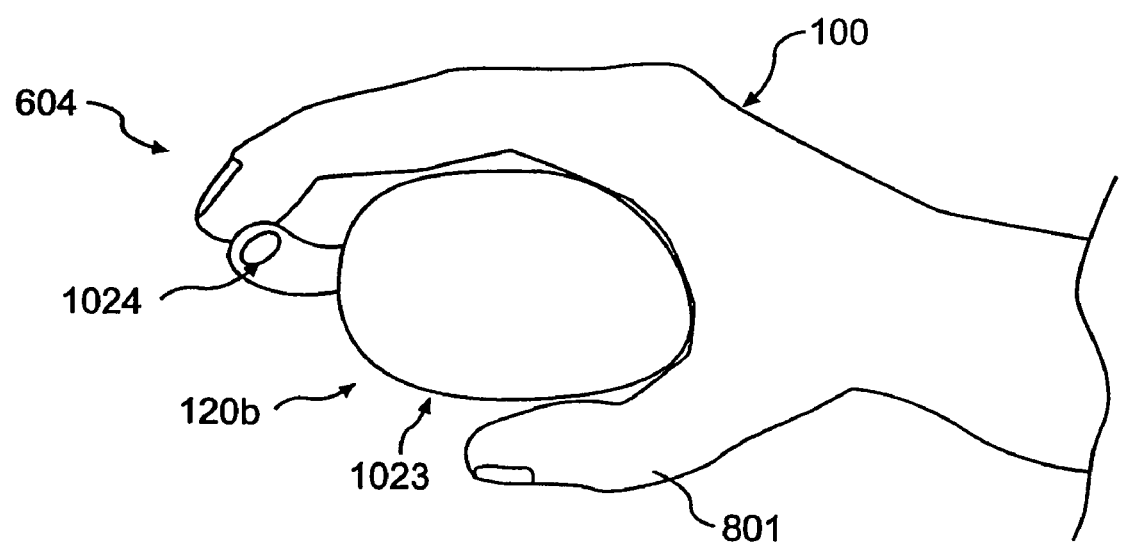
Figure 22E:
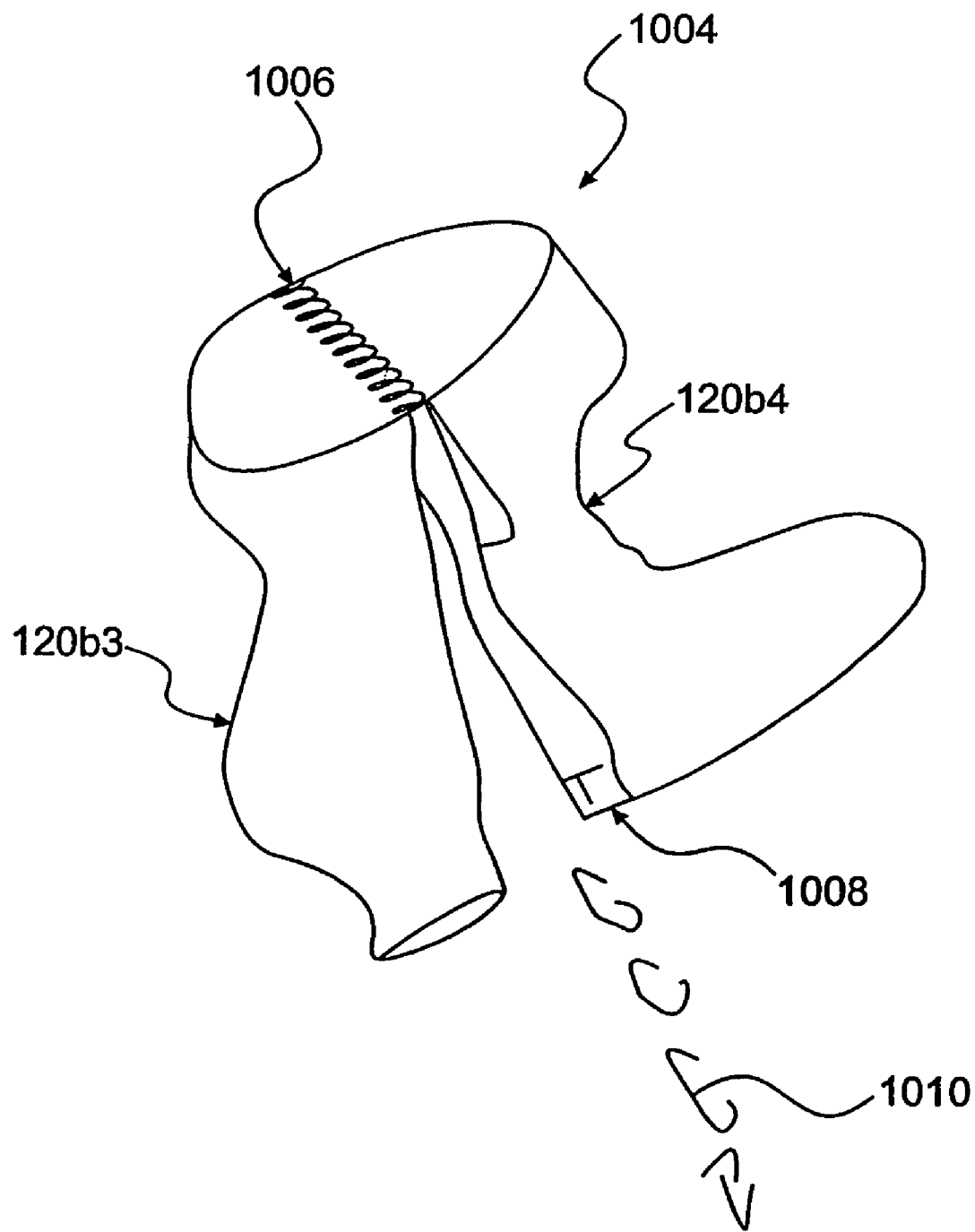
Figure 22F:
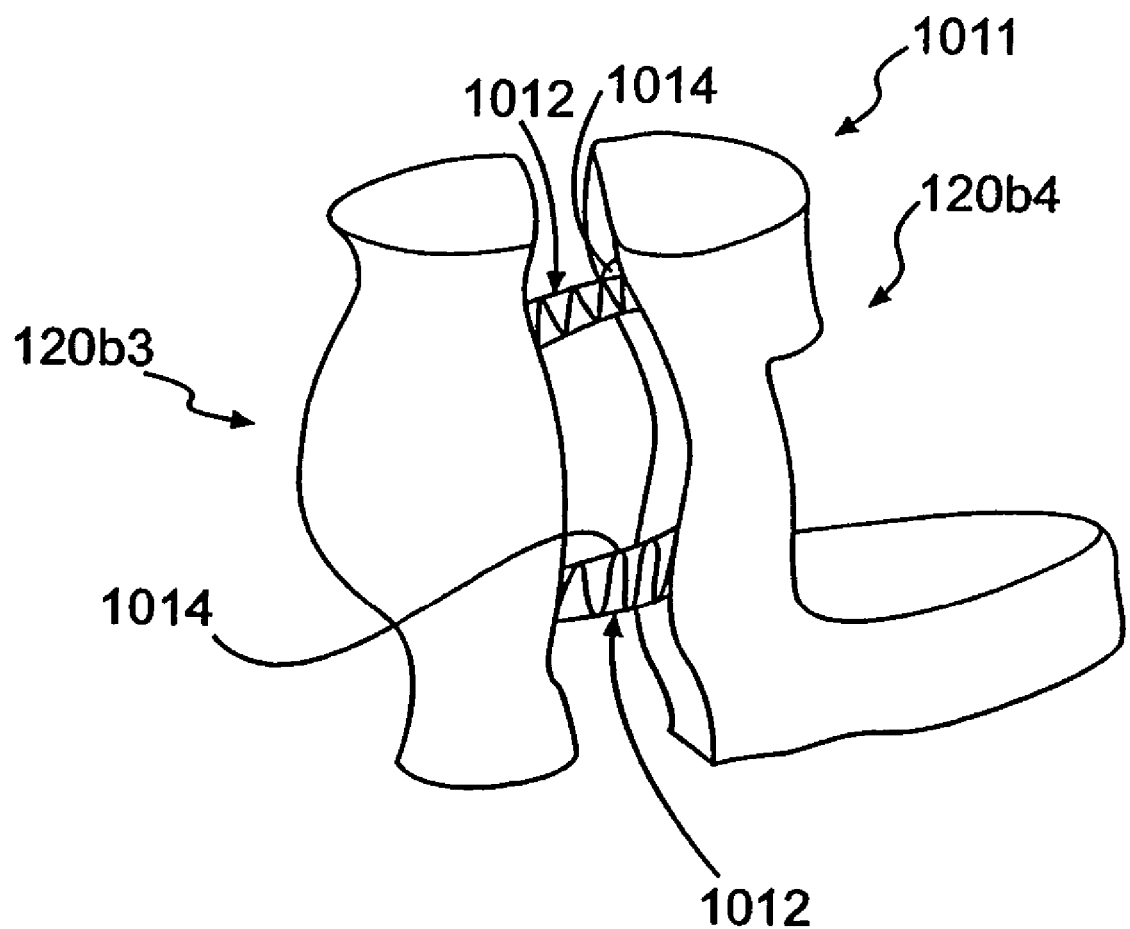

A further example of using bisected sections of a handle of the present invention is illustrated in FIG. 22F as a hand exercise machine 1011, which uses sections 120b3 and 120b4 of FIGS. 16C and 16D connected by tracks 1012 which are surrounded by springs 1014 so that the sections 120b3 and 120b4 can be pulled together by the hand and released by action of the springs 1014.

Figure 20:
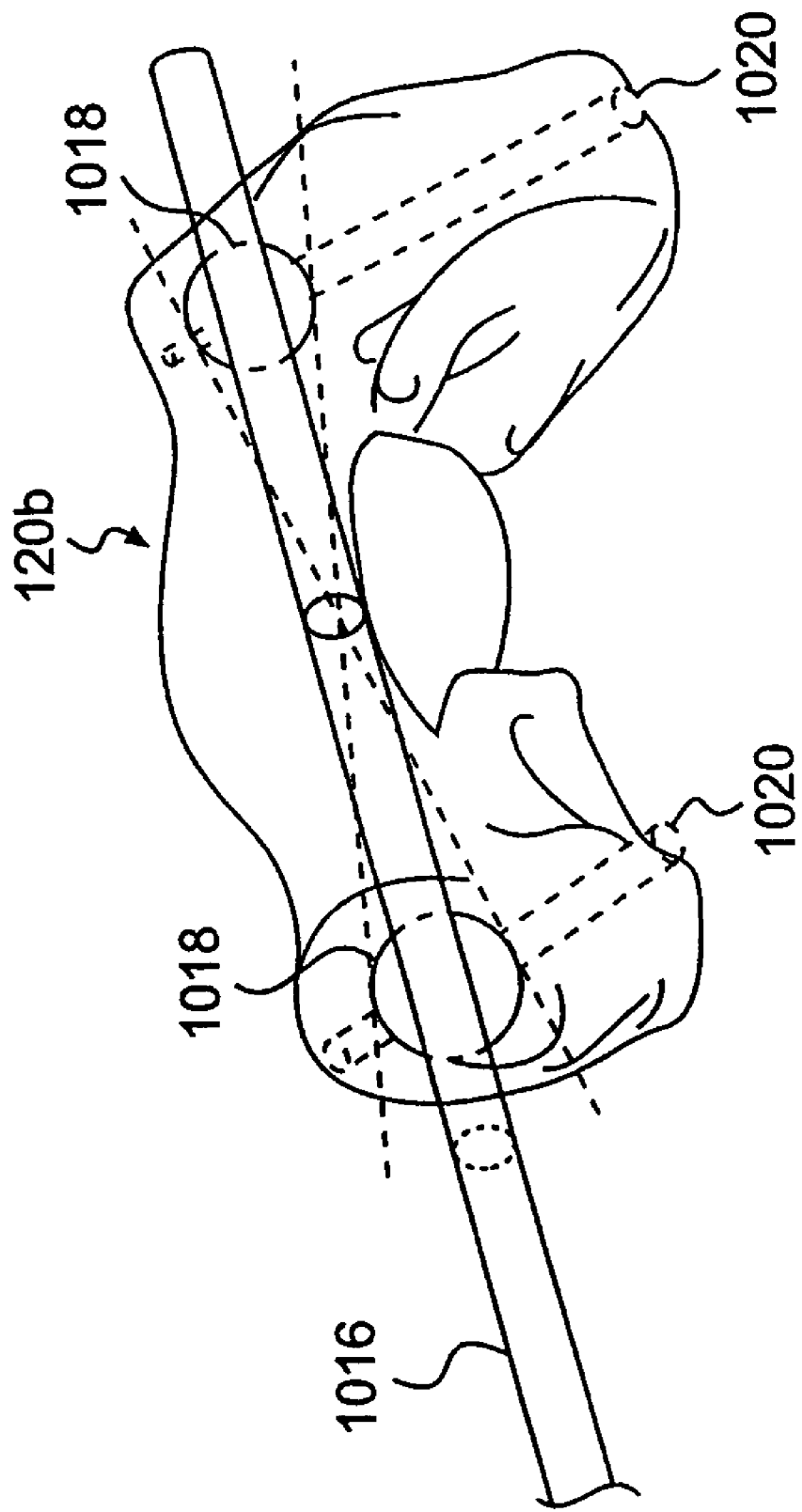
FIG. 20 illustrates another embodiment of a handle of the present invention of a design that can slide along a shaft and can be adjusted to make the position of the wrist and hand neutral to each other when the handle slides along the shaft.

FIG. 20 illustrates another embodiment of a handle 120b of FIG. 9B of the present invention of a design that can slide along a shaft 1016. Such a handle can be adjusted to make the position of the wrist and hand neutral to each other. This can be done by incorporating two opposing cones 1018 with the larger circles at the ends of the handle 120b and a smaller circle in the middle of the handle 120b. Adjustments to achieve a neutral wrist position can be made with screws 1020. The handle 120b of FIG. 20 can be used in conjunction with a handlebar for a bicycle or motorcycle, for example.

Figure 21A:
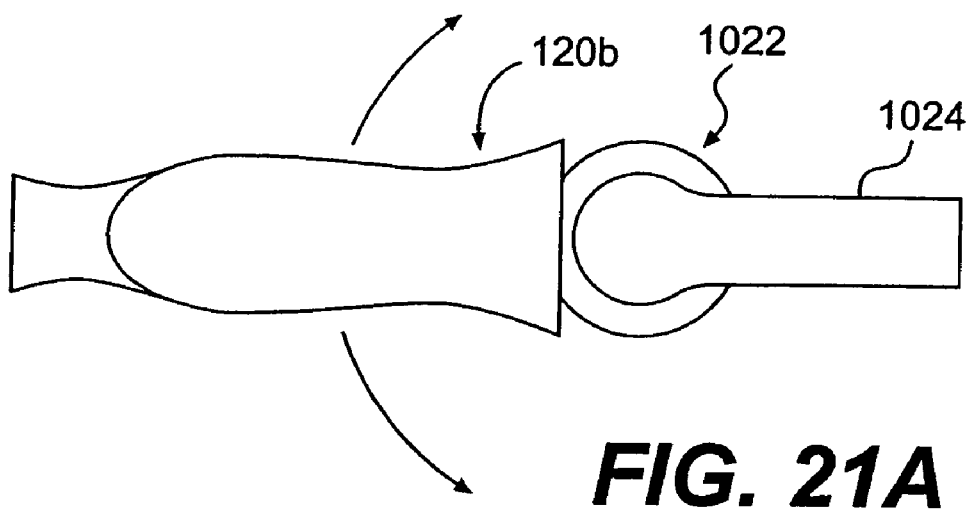
FIG. 21A illustrates a distal (front) view and FIG. 21B a side view of another embodiment of a handle of the present invention that can be rotated or the angularity adjusted in various directions.
Figure 21B:
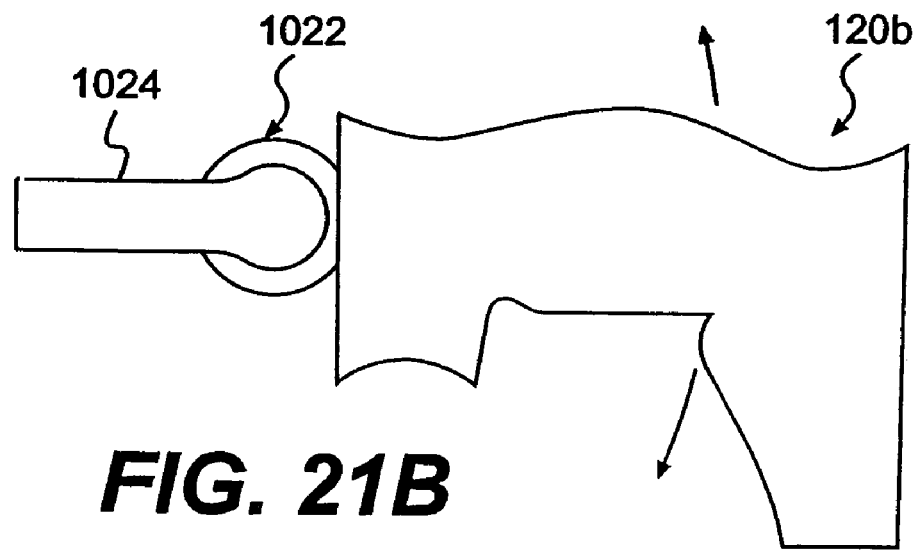

FIG. 21A illustrates a distal (front) view and FIG. 21B a side view of another embodiment of a handle 120b of FIG. 9B of the present invention that can attached at any angle and by various methods to a device and be rotated or adjusted in various directions. For example, the embodiment of the handle 120b is attached by a ball joint arrangement 1022 to a pole 1024 in FIG. 21A and FIG. 21B.

FIGS. 22A-22D illustrate various an embodiments of handle 120b of the present invention used as squeezing devices, with FIG. 22A through FIG. 22D illustrating a side view of a hand brake, with FIG. 22B illustrating the distal (front) view of the hand brake, with FIG. 22C illustrating a perspective view and FIG. 22D illustrating a perspective view of the hand engaging the hand brake of FIG. 22A.

Hand controls for bicycle brakes are based on lever systems. The lever is attached to wire and the fixed part is attached the handlebar. Squeezing or pulling the lever decreases the width between its non-fixed end of the lever and the handlebar. In reference to the hand 100, the thumb 801, thenar muscle area 302 and hypothenar muscle area 402 are fixed to the handlebar while the long fingers 604 pull the lever. The ring finger 608 and small finger 609 can be used to initiate the pull of the lever. These fingers are typically smaller and associated with smaller flexor forearm muscles. These fingers 608 and 609 have to reach further and work harder than the index finger 606 and the middle finger 607. It is not efficient to use the weakest fingers to initiate and perform the greatest pull. Furthermore, the muscle systems for the long fingers 604 for gripping a lever are not synchronized.

The weaker superficial flexor muscle pulls the middle phalanges 606b and 607b of the lesser involved index finger 606 and middle finger 607 while the stronger but smaller deep flexor muscle subunits pull the distal phalanges 608a and 609a of the ring finger 608 and small finger 609. Thus, asymmetrical muscles are used to pull the lever that pulls the wire.

Continuing with reference to FIGS. 22A through 22D, a more efficient handbrake 1023 and method of its use would be to have a moving member 1024 with the same shape as the front of handle 120b placed parallel to the handle 120b such that as it is squeezed the whole member 1024 moves the same distance. Such member 1024 is squeezed toward the fixed handle 120b to pull a wire that pulls on the brake system 1024 can also be designed to push hydraulic fluid to actuate a braking mechanism.

Similarly, many surgical instruments that bight into tissue are based on the same the principle of using the long fingers to pull a lever. Likewise many tools that fit the hand also are based on a lever system to effect the jaws of the tool to grip. This is similar to a scissors but in a scissors both members pivot on a fixed shaft. Thus, a system similar to the handbrake 1023 illustrated in FIGS. 22A through 22D can be used for surgical instruments and other tools that are held by the hand and based on a lever principle.

Figure 23A:
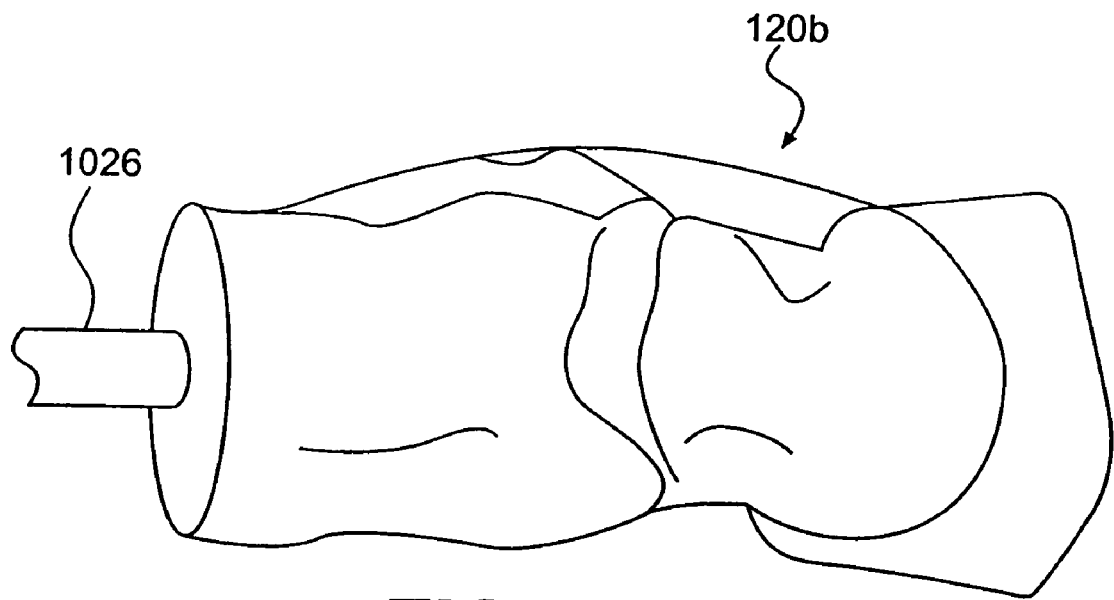
FIGS. 23A-23I illustrate various embodiments of handles of the present invention for use with various implements, as can be integrated with a shaft as in FIGS. 23A and 23B, attached to a shovel as in FIGS. 23C, 23D, 23E, as used with barbells in FIG. 23F, as used with a chin-up pole as illustrated in FIG. 23G, as attached to a ski pole as illustrated in FIG. 23H, and as attached to a broom handle as illustrated in FIG. 23I.
Figure 23B:
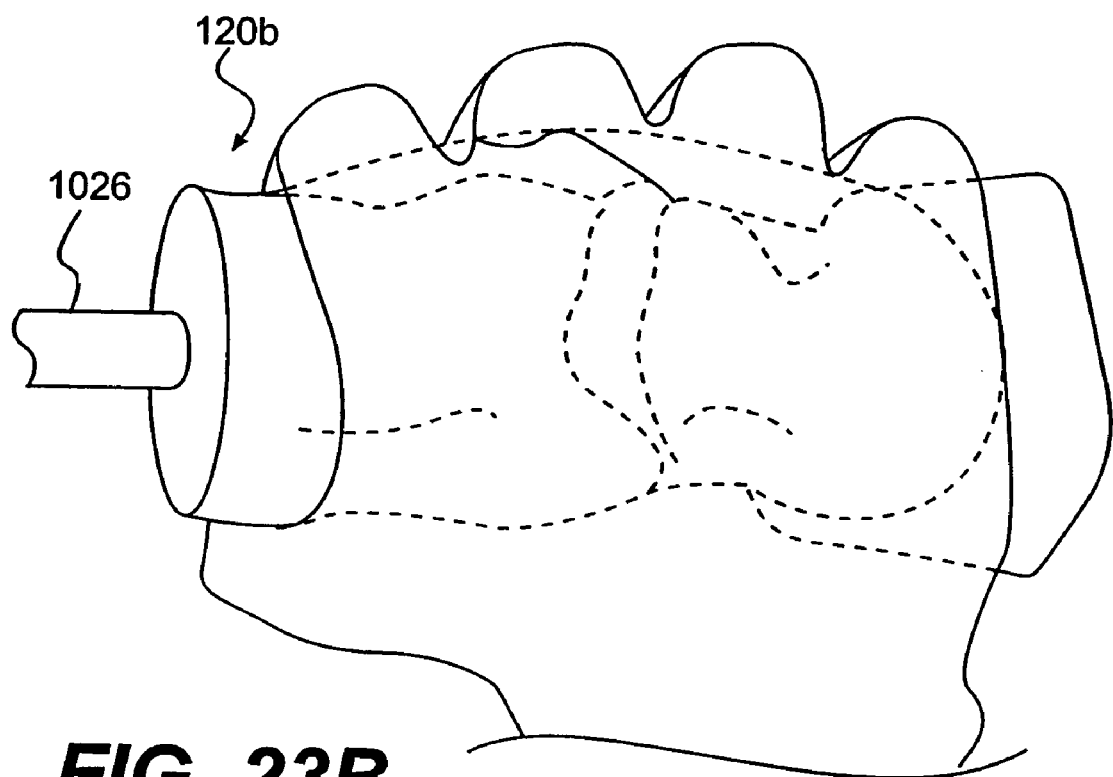

FIGS. 23A-23I illustrate various embodiments of handles 120b of FIG. 9B of the present invention for use with various implements, as can be integrated with a shaft 1026 as in FIGS. 23A and 23B such as a fishing pole. Also, handles 120b illustrated in FIGS. 23A and 23B of the present invention when used as a support, such as on a bicycle or motorcycle can rotate and have a spring mechanism.

Figure 23C:
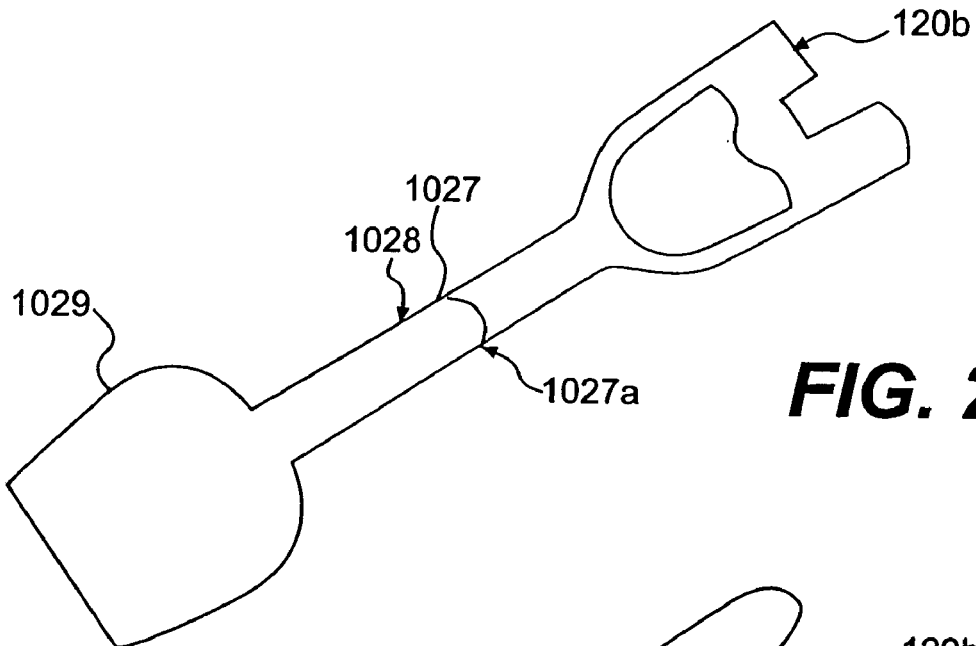
Figure 23D:
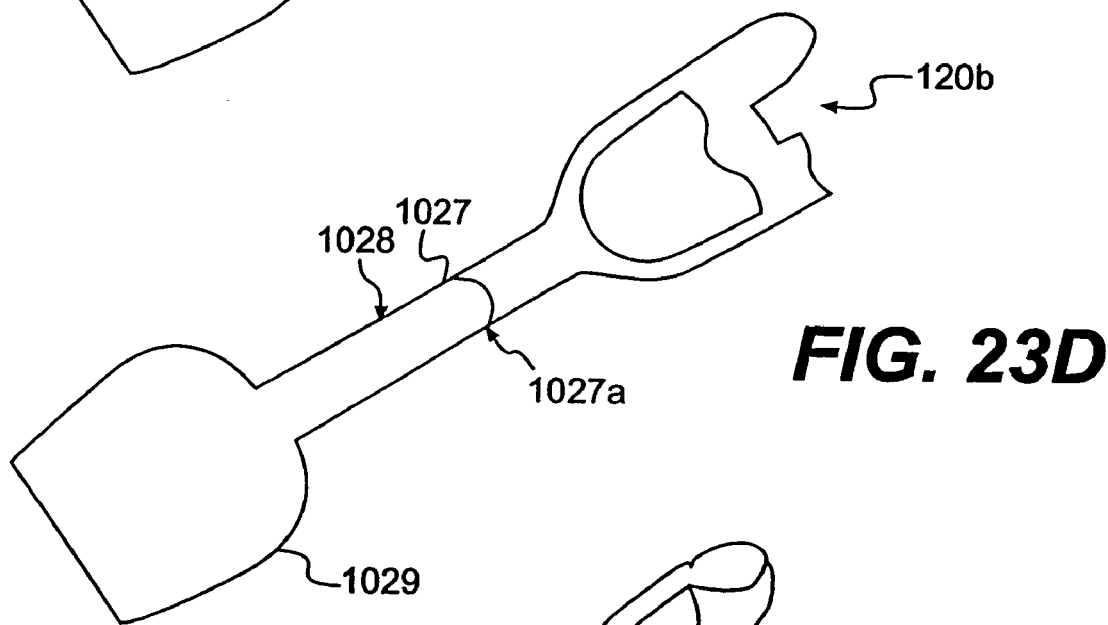
Figure 23E:
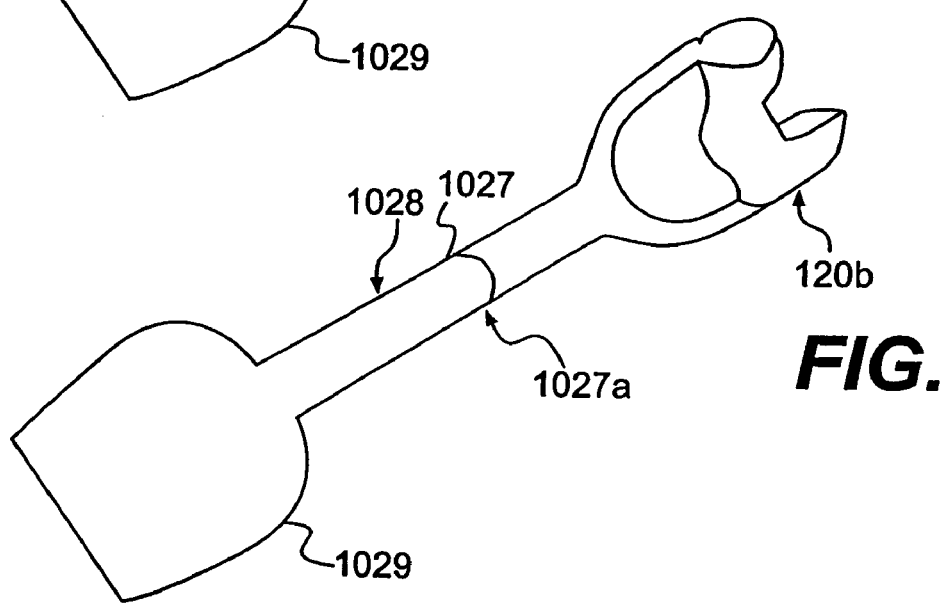

FIGS. 23C, 23D and 23E illustrate embodiments of handle 120b attached to a shaft 1027 of a shovel 1028. The handle 120b of the shovel 1028 can be positioned to rotate with respect to the shaft 1027 through a suitable rotating connecting means 1027a. The handle 120b of shovel 1028 in FIG. 23C is illustrated for use with a right hand 100 and the handle 120b is aligned substantially parallel with the shovel blade 1029. The handle 120b of shovel 1028 in FIG. 23D is illustrated for use with a left hand 100 and the handle 120b is aligned substantially parallel with the shovel blade 1029 but rotated approximately one hundred eighty degrees from the position of the handle 120b in FIG. 23C. The handle 120b of shovel 1028 in FIG. 23E is illustrated for use with a right hand 100 with the handle 120b being rotated substantially ninety degrees from the position of the handle 120b in FIG. 23C so as to be aligned substantially perpendicular with the shovel blade 1029.

Figure 23F:
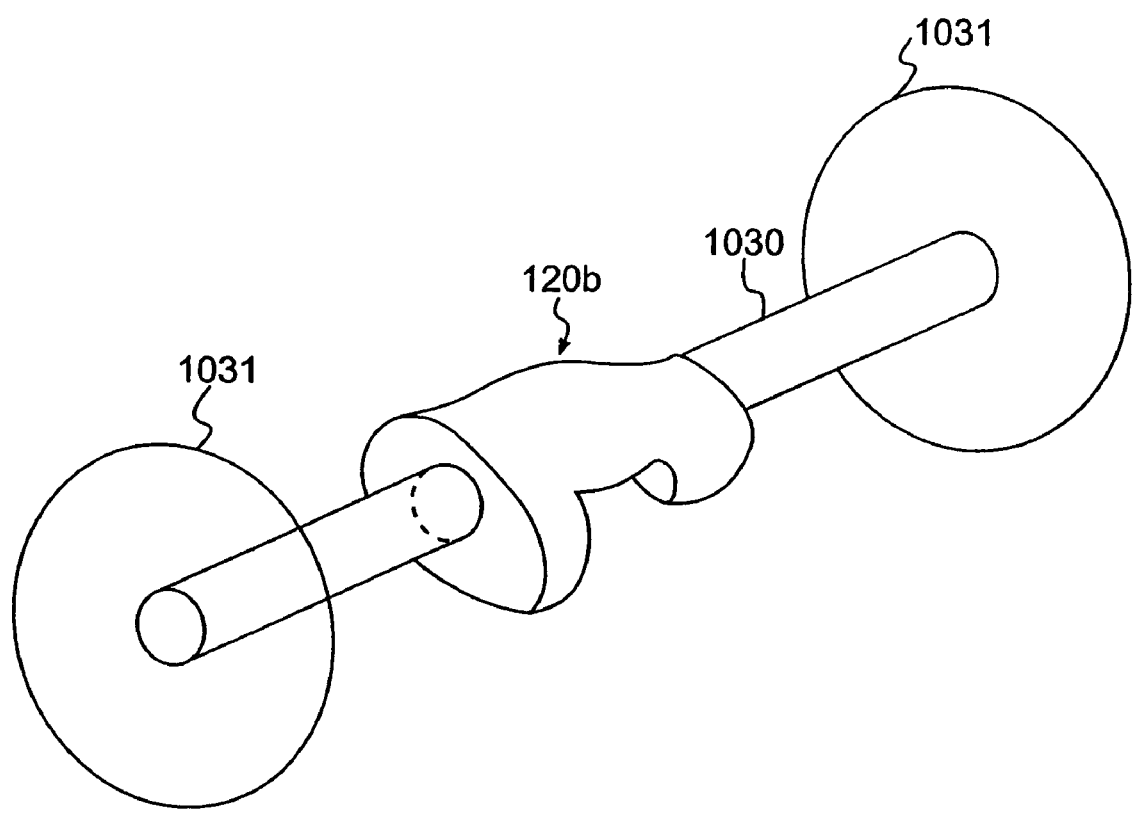
Figure 23G:
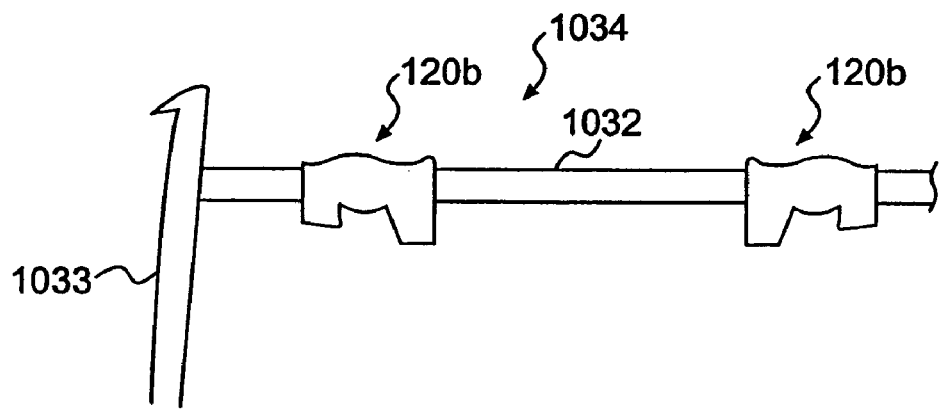

FIG. 23F illustrates an embodiment of a handle 120b attached to a shaft 1030 as in as used with barbells 1031. FIG. 23G illustrates an embodiment of a right handle 120b and left handle 120b attached to a shaft 1032 fixed in a member 1033 as in as used with a chin-up pole 1034.

Figure 23H:
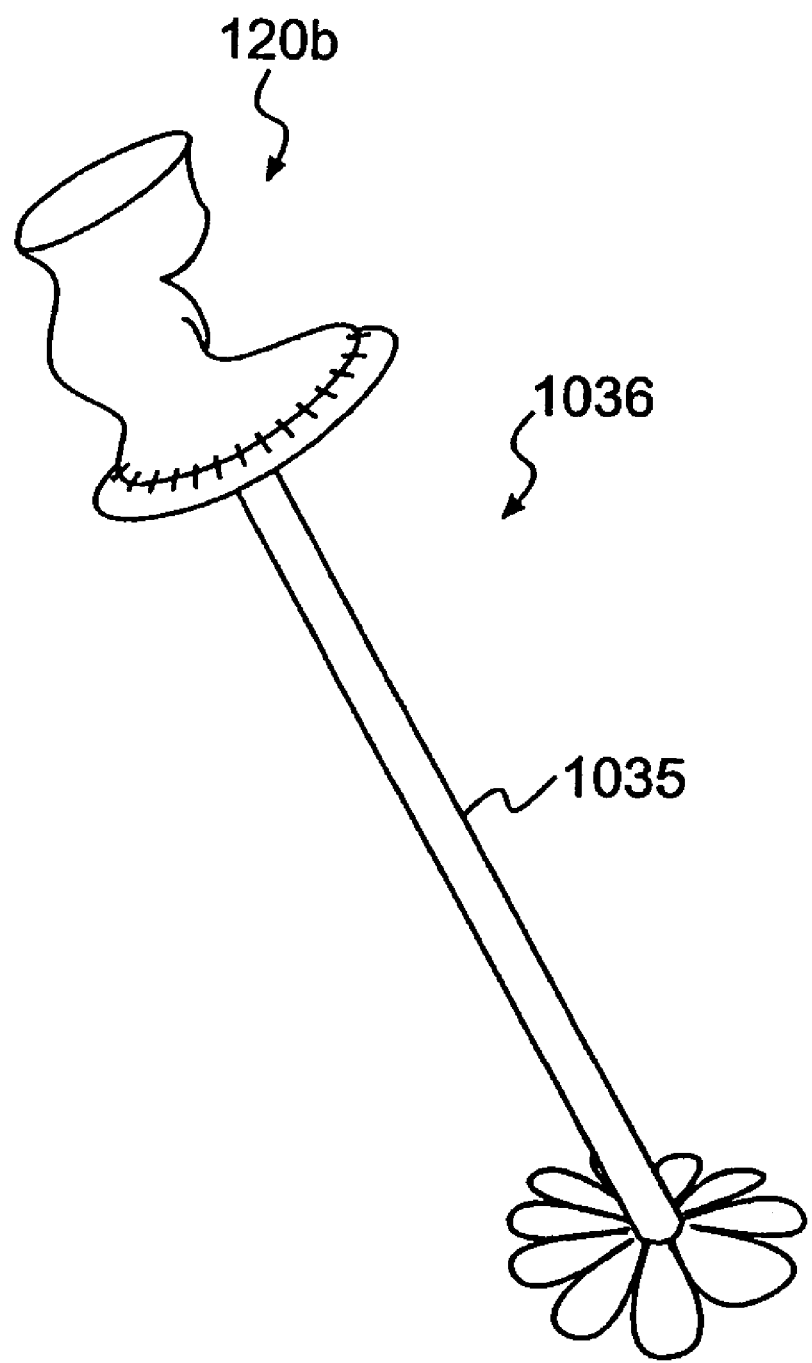

FIG. 23H illustrates an embodiment of a handle 120b attached to a shaft 1035 for use with a ski pole 1036.

Figure 23I:
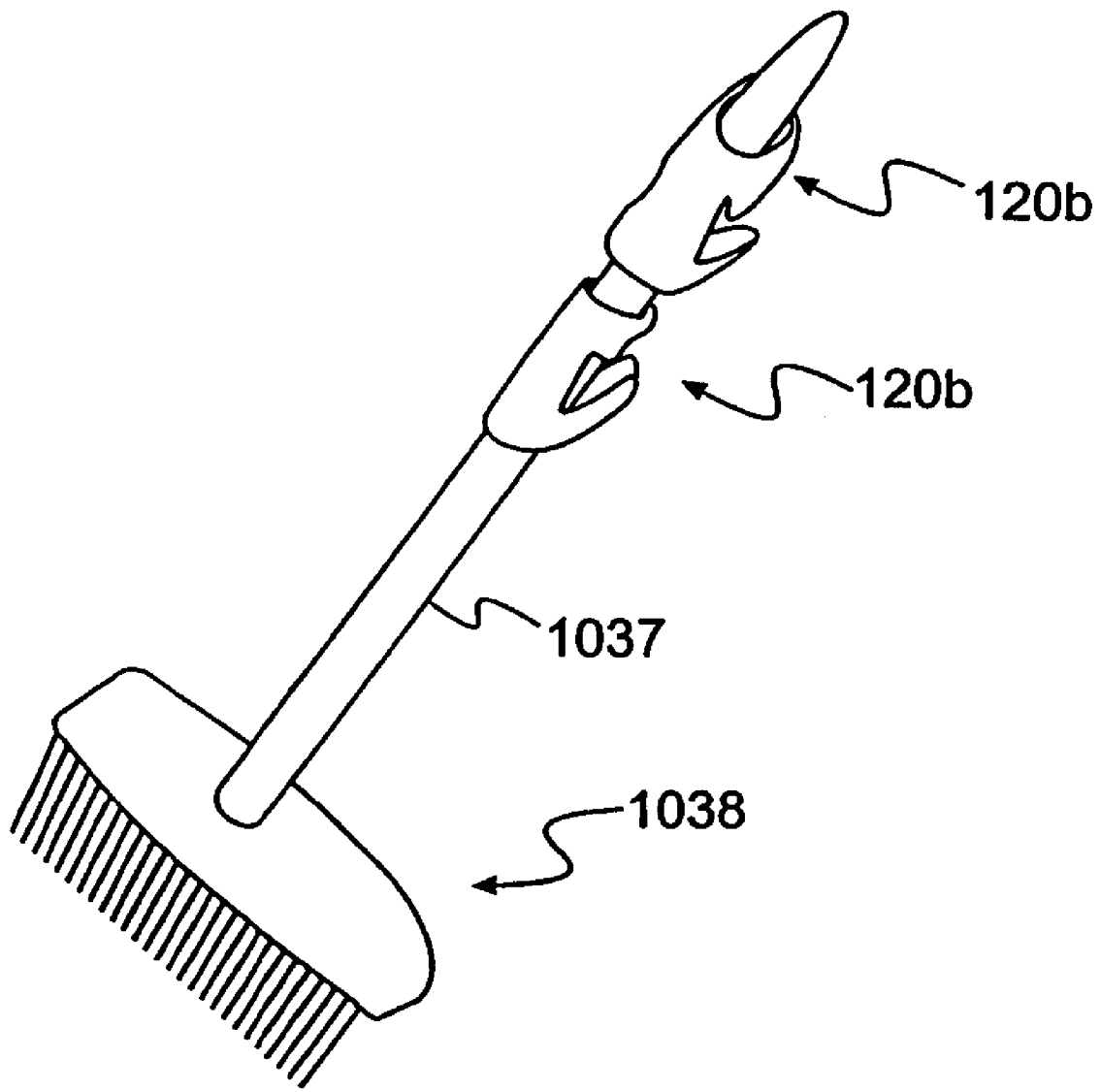

FIG. 23I illustrates an embodiment of a handle 120b attached to a shaft 1037 as used with a broom 1038.

FIGS. 24A-24D illustrate other embodiments using a handle of the present invention.

Referring first to FIG. 24A and FIG. 24B an embodiment of a handle 120c similar to the handle 120b of FIG. 9B is illustrated, but with a shorter ulnar extension, as to be used for rotation such as with a screwdriver 1039 as illustrated in FIG. 24A and as to be used for rotation when held in a hand 100 for use as a rotating handle 120c with a shaft 1040 as illustrated in FIG. 24B.

As illustrated in FIG. 24A and FIG. 24B, the rotating tool shaft handle 120c is designed for both hands. The handle 120c is used as an adjunct to the function of forearm rotation. The handle 120c is designed with shorter proximal ulnar side 553 and fit the ulnar side 401 of the hand 100 closer to the ulnar side of the horizontal crease 101 of the hand 100 so that the hand 100 can encircle the rotating handle 120c more than handle 120a, 120b of the design illustrated in FIG. 9A and FIG. 9B. The shorter ulnar end 553 does not support the hand in the same way as the bicycle type grip 120b illustrated in FIG. 9B. The handle 120c is also designed to have a depression 1041 at the radial end side 321c of the radial section 331 of the elongated body 121c to accommodate the thumb 801 at the radial end of handle 120c. In handle 120c placement of the thumb 801 is similar to the thumb position in the previously discussed 'P Position'.

The middle section 231 of the rotating shaft handle 120c has substantially the same shape as the corresponding section of the handle 120b illustrated in FIG. 9B. The palmar, thumb and distal (front) of the handle 120c with the shorter ulnar end are rounded to fit the palmar arch 102 and the finger cup 601. The long fingers 604 end along the same line L in a substantially linear arrangement similar to the 'T Position' as illustrated in FIG. 14A-14C. The rotating shaft handle 120c provides for no contact or pressure on the ulnar nerve or artery or the CT of the hand 100.

The rotating shaft handle 120c while being used places the thumb 801 parallel and close to the Plane B as defined in FIG. 18 and FIGS. 19A and 19B that extends through the radius bone 303 as previously discussed. Alternately, as illustrated in FIG. 24A1, at the radial end side 321c of the radial section 331 of the elongated body 121c, a central ridge 1041a can be located, which positions the thumb 801 more toward the thumb side 841a of the radial section 331 of the handle 120c and further away in a radial direction from Plane B is desirable because the thumb 801 rests not only in a more comfortable position for holding such a handle 120c, but this alternative position enhances the motor function used for the forearm to rotate back and forth.

Moreover, the rotating tool shaft handle 120c can be adapted to accommodate a shaft 1039, 1040 between the middle finger 607 and the ring finger 608. For screwdrivers the middle finger 607 and the ring finger 608 finger must spread to allow the shaft 1039, 1040 to be position between these fingers 608 and 607. The aperture 1042 for the screwdriver shaft, which is usually between the middle finger 607 and the ring finger 608, can be shifted and placed between the index finger 606 and middle finger 607.

Figure 24D:
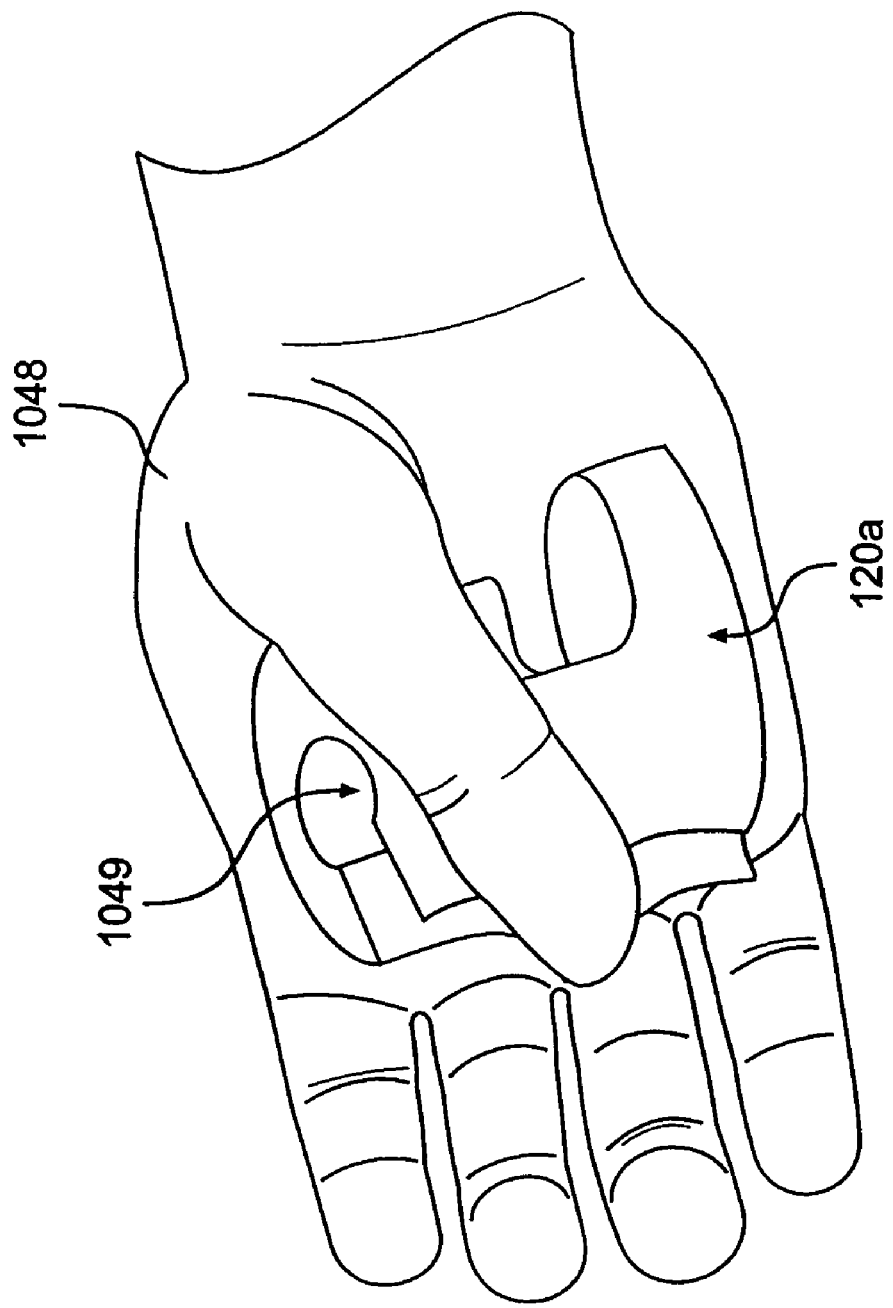
Figure 25:
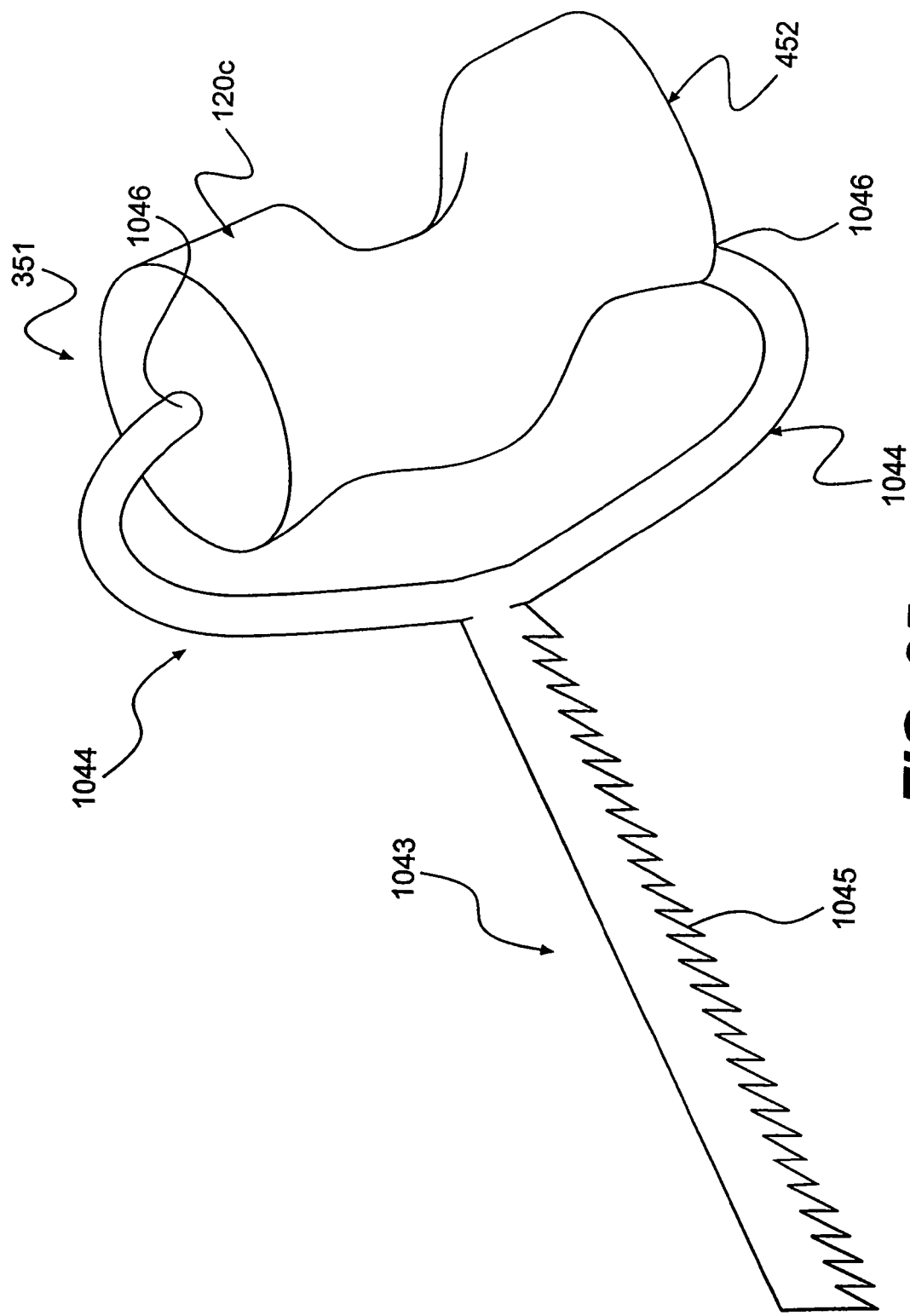
FIG. 25 illustrates another embodiment for a handle of the present invention to be used as a saw.

Referring now to FIG. 25, FIG. 25 illustrates and embodiment of a tool shaft handle 120c of FIGS. 24A and 24B designed for use with a saw 1043. When the handle 120c is used as a handle for a saw 1043 each arm 1044 connecting or integrated with the saw blade 1045 typically extends from the radial side edge 351 and from the ulnar section edge 452 of a handle 120c meeting the saw blade 1045. Apertures 1046 are respectively positioned in the handle 120c to receive the arms 1044.

Referring now to FIG. 24C, FIG. 24C illustrates and embodiment of handle 120a of FIG. 9A incorporating one or a plurality of buttons or switches 1047, such as for various functional controls in at least one or a plurality of locations as illustrated in FIG. 24C.

Referring now to FIG. 24D, FIG. 24D illustrates and embodiment of handle 120a of FIG. 9A and as integrated in a glove 1048, having an open slot 1049 for receiving a tool or implement. Furthermore, the palmar side of the middle section of a handle of this design can attach to the inside or outside of a glove so as to maintain the palmar arch when the hand grips such items as a golf club or tennis racquet.

Figure 26A:
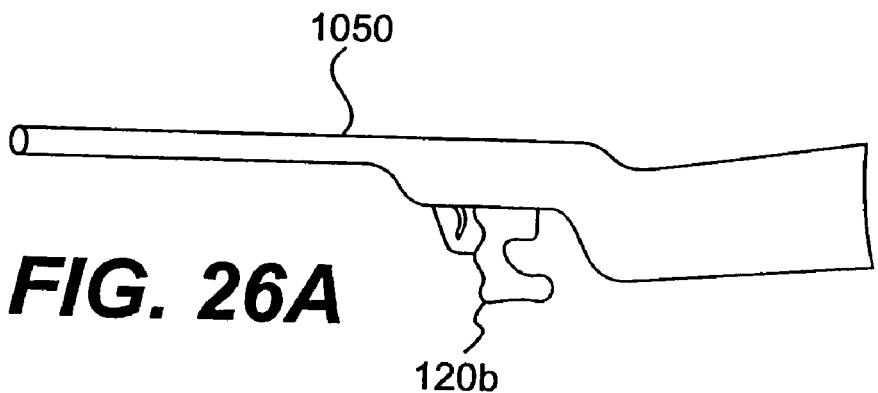
FIGS. 26A-26D illustrates other embodiments for handles of the present invention, as for use with a rifle handle as illustrated in FIG. 26A, as for use as a device for front to back pivotal movement as illustrated in FIG. 26B, for side to side pivotal movement as illustrated in FIG. 26C, and for rotation in combination as illustrated in FIG. 26D.
Figure 26B:
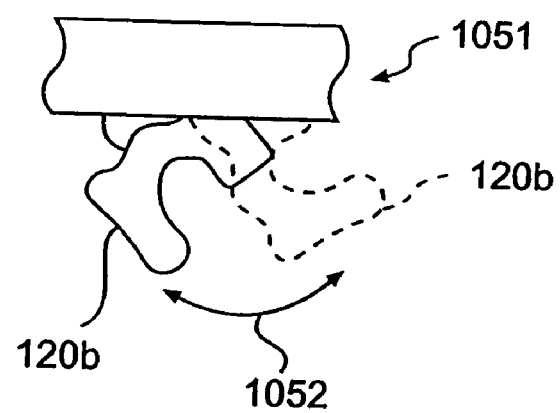
Figure 26C:
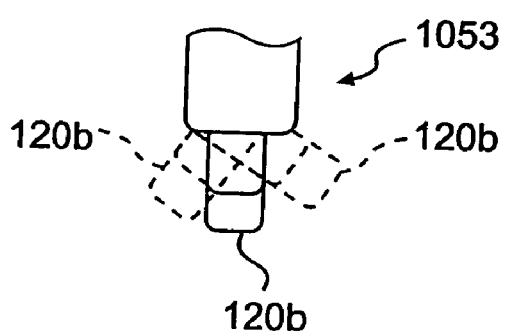
Figure 26D:
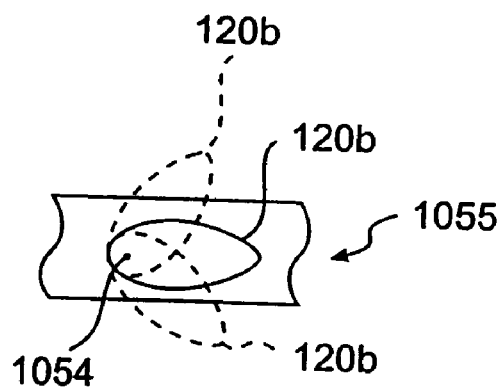

FIGS. 26A-26D illustrates other embodiments for handles of the present invention, as a handle 120b of FIG. 9B for use with a rifle 1050 as illustrated in FIG. 26A, as a handle 120b of FIG. 9B for use with a device 1051 for front to back pivotal movement indicated by the arrow 1052 as illustrated in FIG. 26B, as a handle 120b of FIG. 9B for use with a device 1053 for side to side pivotal movement as illustrated in FIG. 26C, and a handle 120b of FIG. 9B for use for rotation around a shaft 1054 in combination with a device 1055 as illustrated in FIG. 26D.

Figure 27A:
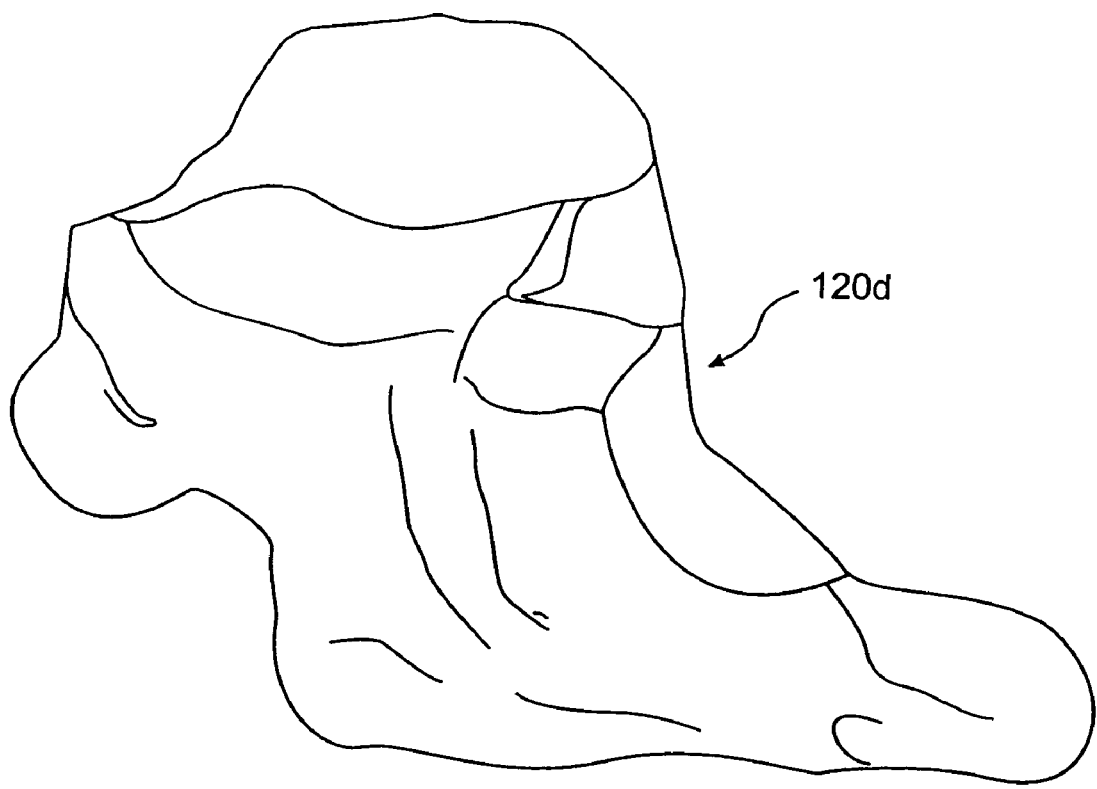
FIG. 27A-27F illustrate another embodiment for a handle of the present invention for use as a computer mouse or an interactive device, with a thumb side profile illustrated in FIG. 27A, a top or radial profile view illustrated in FIG. 27B, a thumb side profile view engaged by a hand as illustrated if FIG. 27C, a top or radial profile view engaged by a hand as illustrated in FIG. 27D, a long finger side view as illustrated in FIG. 27E, and long finger side view engaged by a hand as illustrated in FIG. 27F.
Figure 27B:
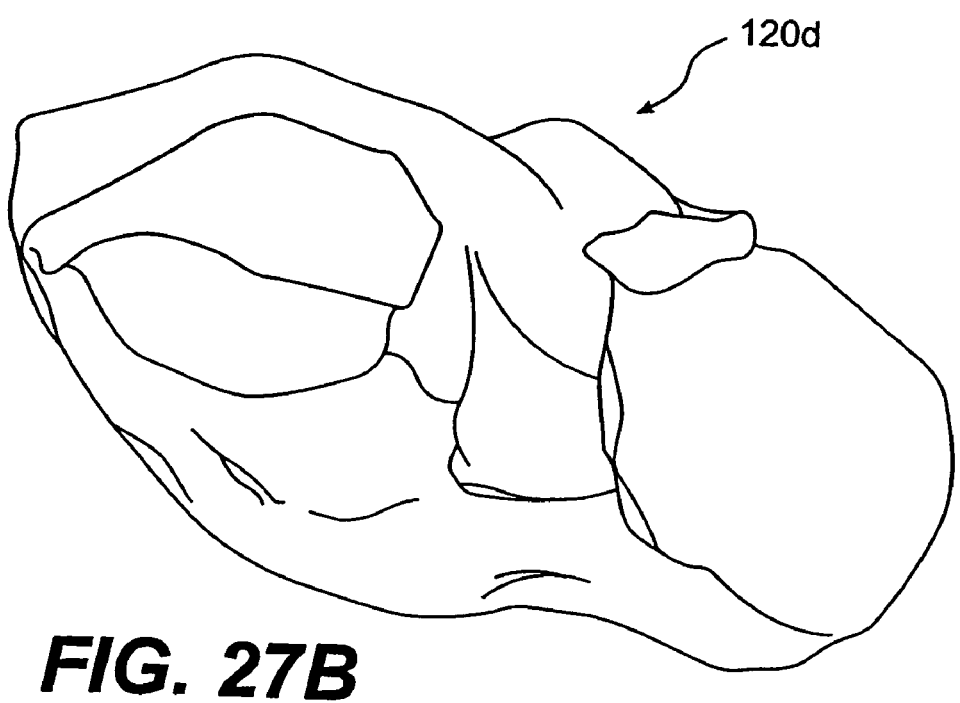
Figure 27C:
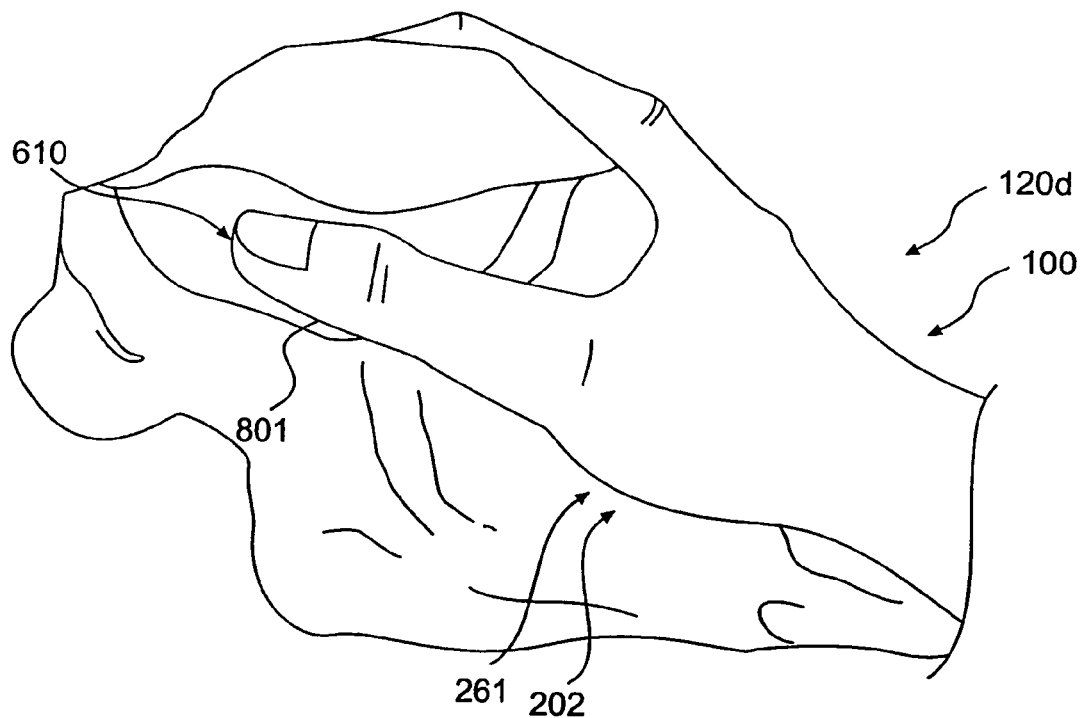
Figure 27D:
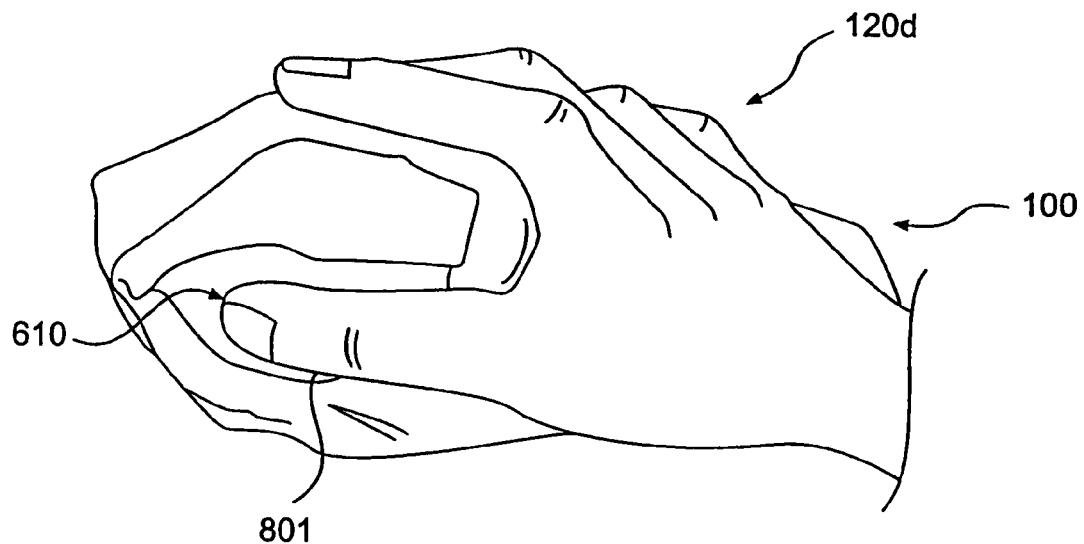
Figure 27E:
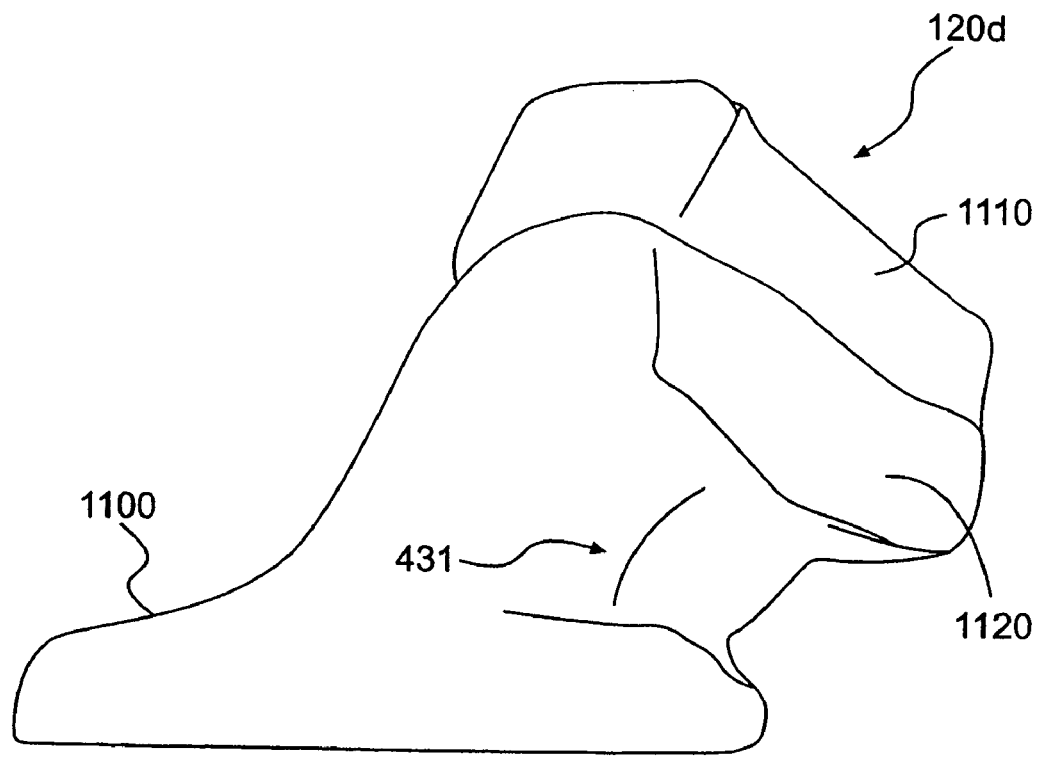
Figure 27F:
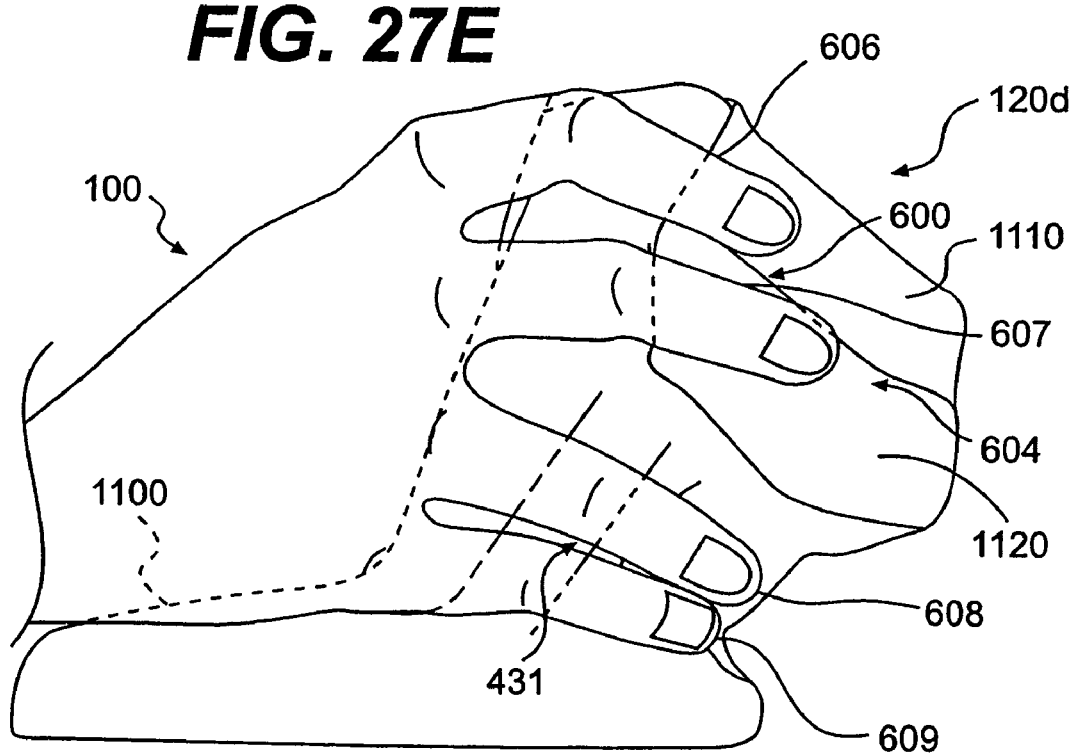

FIG. 27A-27F illustrates another embodiment for a handle 120d of the present invention for use as a computer mouse or an interactive device based on handle 120a of FIG. 9A, with a thumb side profile illustrated in FIG. 27A, a top or radial profile view illustrated in FIG. 27B, a thumb side profile view engaged by a hand as illustrated if FIG. 27C, a top or radial profile view engaged by a hand as illustrated in FIG. 27D, a long finger side view as illustrated in FIG. 27E, and long finger side view engaged by a hand as illustrated in FIG. 27F.

Continuing with reference to FIGS. 27A-27F, existing computer mice and similar implements used with buttons or switches force the hand 100 and forearm to pronate so that the wrist 204 is at the end of its range motion. Wrist joints are strained from this position and can become injured. This embodiment of handle 120d in FIGS. 27A-27F resolves the problem of excessive wrist pronation while using a computer mouse by maintaining neutral radial rotation of the forearm, wrist and hand. The mouse handle 120d based on handle 120a illustrated in FIGS. 27A-27F is based upon the neutral position defined as the 'N Position' and shows an embodiment made for a right hand 100. Similar to the embodiment of the handle 120a of FIG. 9A, the tip 610 of the thumb 801 when engaging the handle 120d opposes the space 600 between the index finger 606 and the middle finger 607, and the ring finger 608 and small finger 609 wrap around the ulnar section 431 of a handle 120d of this design. The ring and small fingers 608 and 609 are flexed more than the index finger 606 and middle finger 607. When the handle 120d is used with the hand 100, a void 261 is present under the TCL 202, and an ulnar support 1100 and supports 1110 and 1120 respectively for index finger 606 and middle finger 607 are also present in the handle 120d. This handle 120d also maintains the neutral wrist position at approximately 30 degrees as defined and illustrated with respect to FIGS. 18 and 19.

Alternatively, the handle 120d of FIGS. 27A-27F can be used as a joystick or a controller for helicopters or the like.

Figure 28:
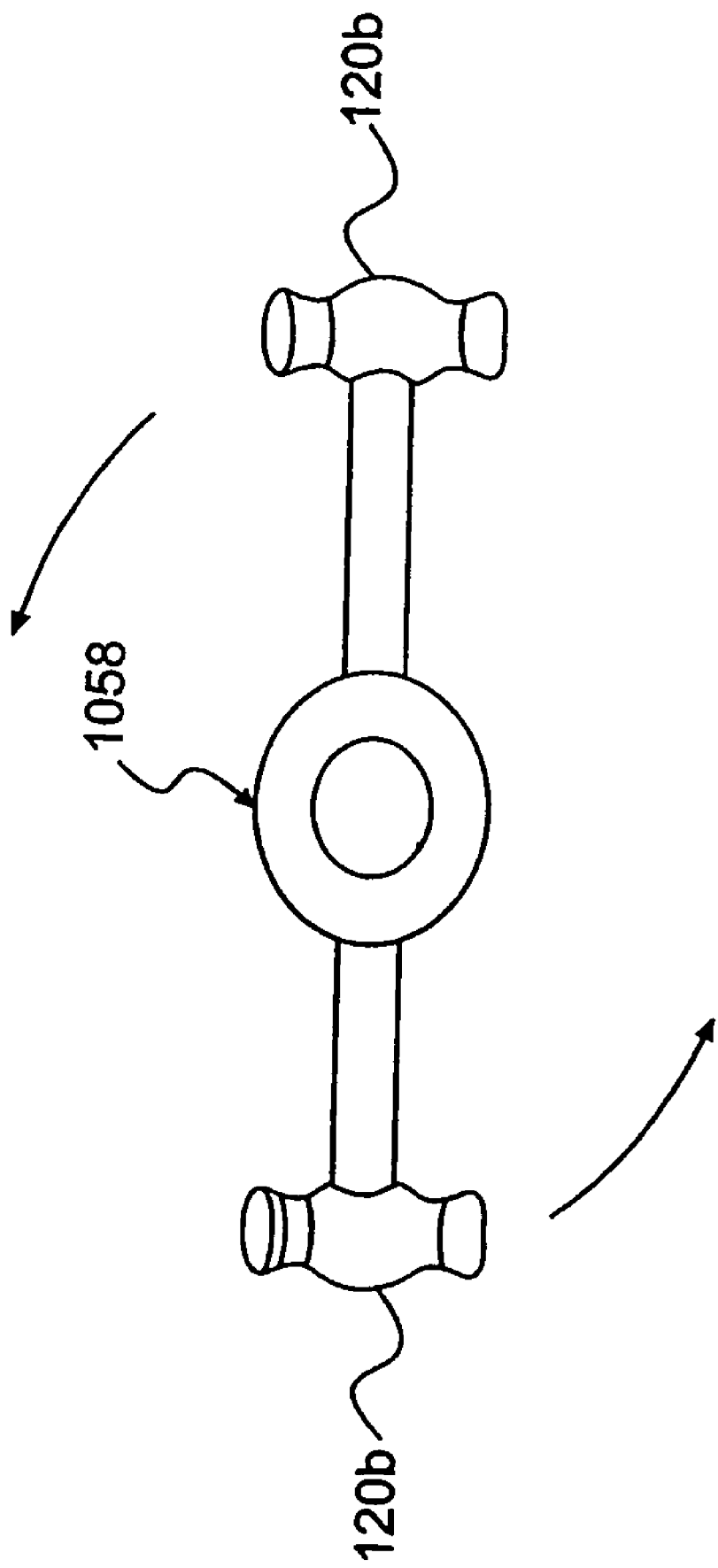
FIG. 28 illustrates another embodiment for a handle of the present invention for use with a steering wheel or steering mechanism.

FIG. 28 illustrates another embodiment for a handle of the present invention based on handle 120b or FIG. 9B for use with a steering wheel or steering mechanism 1058.

Figure 29A:
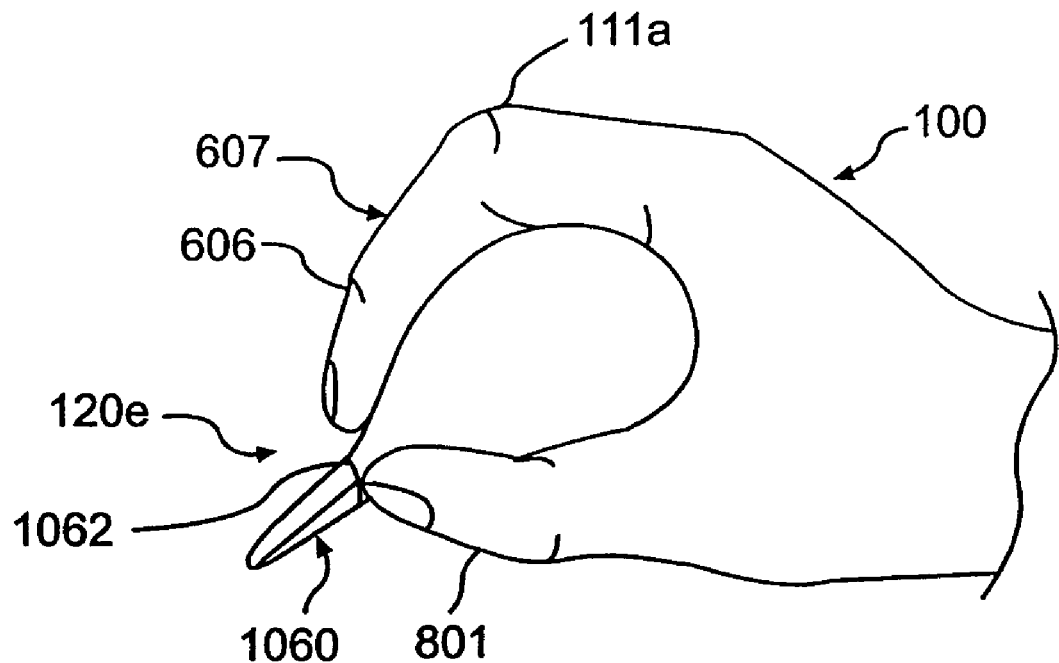
FIGS. 29A and 29B illustrate another embodiment for a handle of the present invention for use as a pen, stylus or hand held instrument, with a radial view engaged by a hand as illustrated in FIG. 29A, and with a thumb side view as illustrated in FIG. 29B.
Figure 29B:
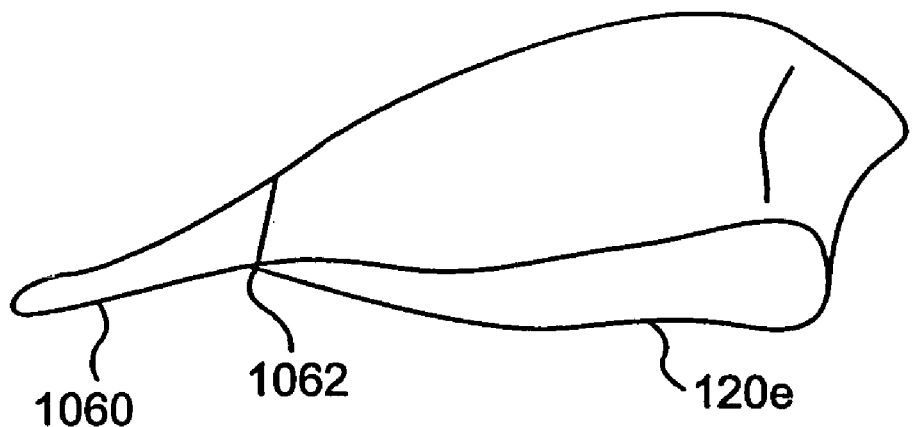

FIGS. 29A and 29B illustrate another embodiment for a handle of the present invention for use as a pen, stylus or hand held instrument. FIG. 29A illustrates a radial view as engaged by a hand and FIG. 29B illustrates a thumb side view.

The handle 120e illustrated in FIGS. 29A and 29B is based on the radial section 331 of handle 120b of FIG. 9B in which the thumb 801, index and middle finger joints 111a are extended as in FIG. 17B. Such a handle 120e can hold a variety of stylus type instruments 1060 including a pen and dental instruments. A swivel mechanism 1062 can be incorporated to rotate the tip of the instrument. A right-hand instrument is shown in FIGS. 29A and 29B that can be modified for the left hand.

FIGS. 30A-30E illustrate other embodiments for a handle of the present invention for use with devices so that the handle fits in the palmar arch of the hand.

Figure 30A:
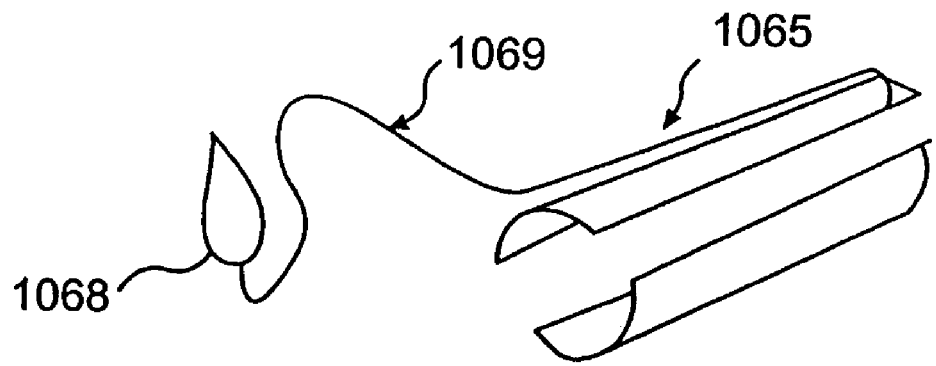
Figure 30B:
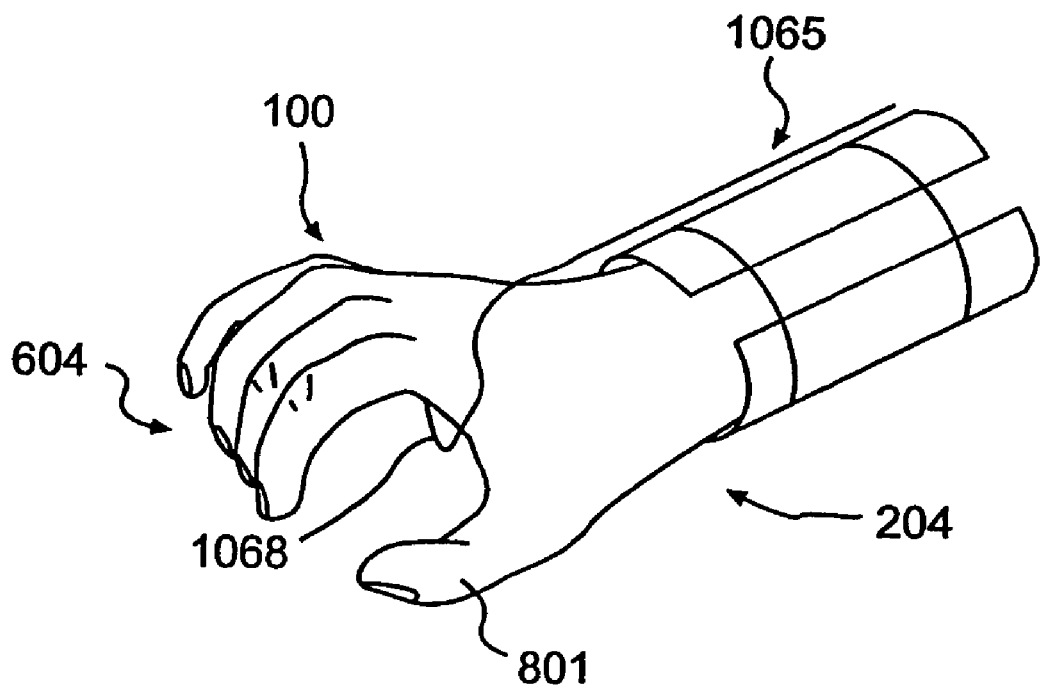

FIG. 30A illustrates a brace 1065 for stabilizing the wrist 204 for CTS, with FIG. 30B illustrating the brace 1065 of FIG. 30A engaged with a hand 100. The wrist brace 1065 for carpal tunnel syndrome is also based on the palmar side of the middle section 231 of the handle 120a of FIG. 9A by including in the brace a support member 1068 for the palmar arch 102 with an extension 1069 that clamps the brace 1065 to the forearm.

Figure 30E:
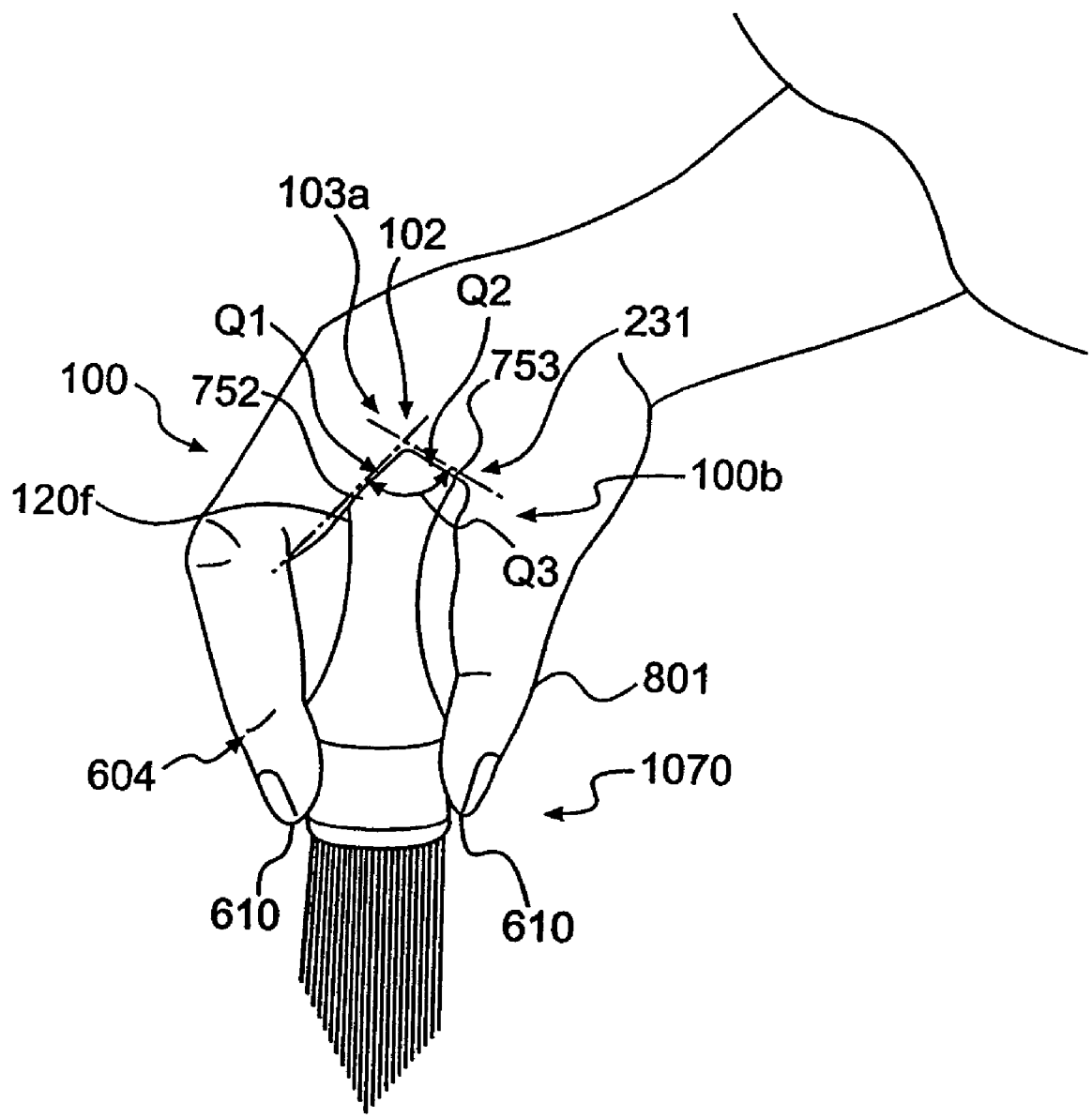

FIG. 30C illustrates a front view and FIG. 30D illustrates a side view of a paintbrush 1070 with a handle 120f based on the palmar side 742 of the middle section 231 of the handle 120a of FIG. 9A of the present invention. FIG. 30E illustrating the handle 120f of the paint brush 1070 of FIGS. 30C and 30D fitting in the palmar arch 102 of the hand 100.

The handle for a paintbrush typically is a large stylus with a heavy brush-type working end 1072. FIGS. 30C, 30D and 30E illustrate a paint brush handle 120f according to the present invention that fits in the palmar arch 102 of the palm 100b of the hand 100. In such a handle 120f for a paint brush 1070 having brush-type working end 1072, the distal side 752 of the handle 120f has a slope Q1 that is more acute than the slope Q2 of the proximal side 753 of the handle 120f to fit the MP joint 103a of the palm 100b when the long fingers 604 are extended similar to the position of the long fingers 604 illustrated in FIG. 17B. This angle Q3 formed by the surfaces of the sides 752 and 753 having the respective slopes Q1 and Q2 of the handle 102f improves the ability of the hand 100 to grasp and pinch a larger object because the thumb 801 opposes the tips 610 of the middle finger 607 and the ring finger 608, which increases the force that can be generated by the long fingers 604 pinching against the thumb 801.

Figure 32A:
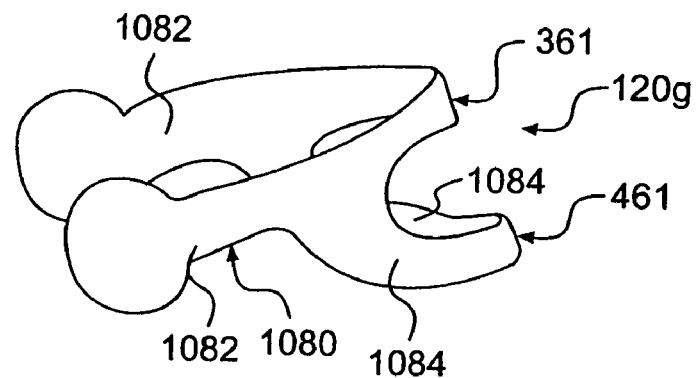
FIGS. 32A, 32B and 32C illustrates other embodiments of a handle of the present invention for use to grasp, pinch or cut, with FIG. 32A illustrating such handle for use with a forceps type implement, and with FIG. 32B illustrating the hand engaging the handle of FIG. 32A, and with FIG. 32C illustrating an implement for use with the handle of FIG. 32A.
Figure 32B:
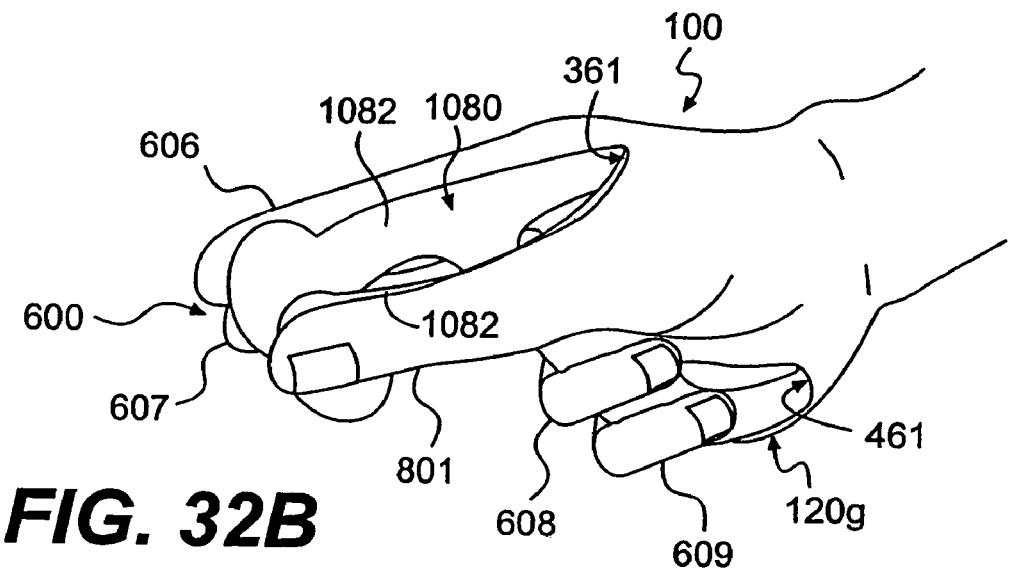
Figure 32C:
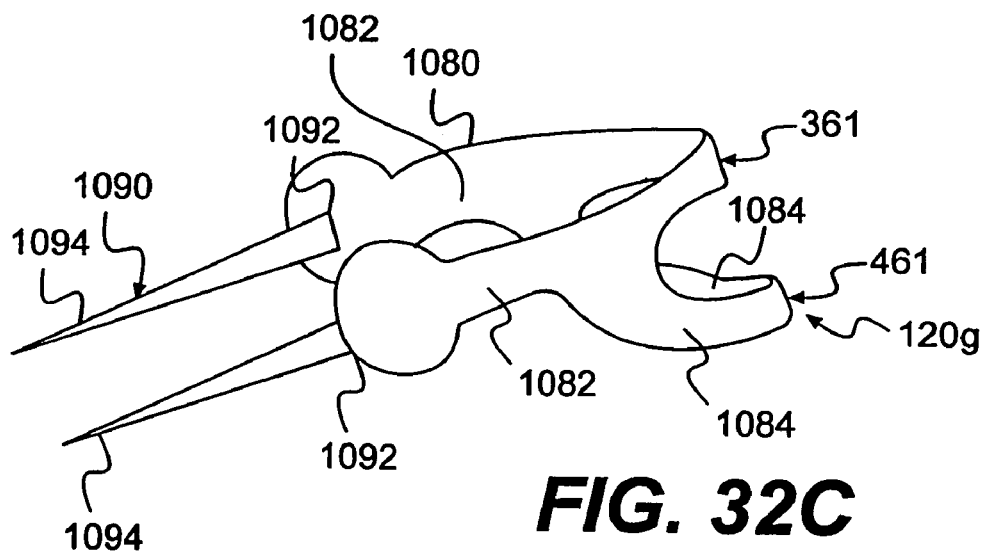

FIGS. 32A, 32B and 32C illustrates other embodiments of a handle 120g of the present invention for use to grasp, pinch or cut, with FIG. 32A illustrating such handle 120g for use with a forceps type implement 1080, and with FIG. 32B illustrating the hand 100 engaging the handle 120g of FIG. 32A, and with FIG. 32C illustrating a handle 102g attached to an implement 1090.

FIG. 32A through 32C illustrates the handle 120g based on the 'T Position' for a forceps or tweezers type implement 1080. The radial end 361 of the handle 120g of the forceps or tweezers implement 1080 meets the hand 100 at the radial side of the horizontal creases 101 of the palm 100b. The ulnar end 461 of the forceps or tweezers implement 1080 meets the ulnar side 401 of the hand 100 distal to the pisiform bone 403 and proximal to the ulnar end of the horizontal crease 101 of the palm 100b. The thumb 801, index finger 606 and middle finger 607 are in a similar position to the thumb 801 and the long fingers 604 illustrated in FIG. 17B. As illustrated in FIG. 32B, the thumb 801 opposes the space 600 between the index finger 606 and the middle finger 607. The material used for the blades 1082 of the forceps or tweezers type implement 1080 can have an inherent spring-like nature that allows the opposing thumb 801 and index finger 606 and middle finger 607 to push against each other. While the design of the handle 120g incorporated in the forceps or tweezers type implement 1080 is based upon the 'T Position', the hand 100 engages the handle 120g using the principles of the 'N Position' in that the ring finger 608 and small finger 609 wrap around the ulnar extension 1084 of the forceps or tweezers type implement 1080 of this design. Such a forceps or tweezers type implement 1080 can serve as the mechanism to selectively open and close a variety of tools or implements. For example, such a forceps or tweezers type implement 1080 can also be selectively attached or detached to an implement 1090 by a suitable connection means 1092 of various types, and, the implement 1090 connected to or integrated with a forceps or tweezers type implement 1080 include, but are not limited to, forceps tips, scissors and many other types of tools or implements that grasp, hold, push, pull and lift. Further, in the forceps or tweezers type implement 1080, implement 1090 can have a tip or an end portion 1094.

In summary, handles of a design according to the present invention can be molded into and contiguous with any of many types of equipment commonly held by a hand. Furthermore, handles based on the design method of the present invention can be attached to or integrated into objects that can be lifted, rotated, moved, carried, etc. Such a handle/grip of the present invention can advantageously be attached or integrated into an object on its radial side, ulnar side, palmar side or thumb side. Additionally, such handle/grip of the present invention can be designed to swivel and/or rotate on various axes at a location of attachment. For example, the handle can be attached to a shaft by an extension and used for turning or steering.

Also, in the handles/grips of the present invention, various materials can be used for fabrication of the handle/grip as, for example, various woods, metals, plastics, composites, rubber compounds, latex's and organic or inorganic materials, suitable for the particular application of a handle or grip of the present invention. Further, various materials can be added to augment and personalize the fit of a handle/grip of the present invention.

The principles, preferred embodiments and modes of operation of the present invention have been described in the foregoing specification. However, the invention which is intended to be protected is not limited to the particular embodiments disclosed. The embodiments described herein are illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A method for designing a handle that corresponds to the sizes of a human hand, comprising the steps of:
    setting the hand in a T position so that the tips of the of the long fingers of the hand are substantially in alignment;
    measuring the distance across the metacarpal bones of the long fingers of the hand from the radial side to the ulnar side across the horizontal creases of the hand thereby defining a length of the handle;
    mapping a first line distal from the base of the thumb of the hand traveling in the ulnar direction to end before the longitudinal crease of the hand;
    mapping a second line distal to the pisiform bone on the ulnar side of the hand from the ulnar side of the hand and traveling toward the radial side of the hand across approximately ⅔ of the hypothenar muscle area of the hand;
    mapping a third line extending from the thenar muscle area of the hand to the hypothenar muscle area at the horizontal creases of the hand; and
    linking the first line, the second line and the third line with a first longitudinal line and a second longitudinal line that cross the palm of the hand thereby defining a proximal side for a handle of a corresponding size for a hand having a portion away from the carpal tunnel of the hand.

2. The method for designing a handle according to claim 1, wherein the distance measured across the metacarpal bones at the horizontal creases of the hand between the ulnar side and the radial side of the hand is in a range of from 7 to 12 cm.

3. The method for designing a handle according to claim 1, further comprising the step of providing the length of the handle to include a portion extending beyond the long fingers and the palmar surface of the hand at the radial side and the ulnar side of the hand to position the index finger and the small finger of the hand to prevent slippage of the hand.

4. A method for designing a handle for a human hand, comprising the steps of:
    setting the hand in a position so that the tips of the long fingers of the hand are substantially in alignment, the thumb of the hand opposes the index finger and the middle finger of the hand, and the ulnar side of the hand is resting on a planar surface; and
    combining the edges of a first surface, a second surface and a third surface to form a fourth surface to determine a shape measurement for a handle for the hand, and
    wherein the first surface is the horizontal plane of the planar surface on which the ulnar side of the hand rests,
    wherein the second surface is a horizontal plane that touches the radial side of the hand and is parallel to the horizontal plane of the planar surface on which the hand rests,
    wherein the third surface is vertical to the horizontal plane of the planar surface on which the hand rests, and the third surface starts at the surface of the thenar eminence at the base of the thumb of the hand and ends at the palmar surface of the long fingers of the hand, and the position at which the third surface meets the long fingers of the hand is dependent upon the distance of the space between the thumb of the hand and the index finger of the hand when the hand is set in the position so that the tips of the long fingers of the hand are substantially in alignment, and the thumb of the hand opposes the index finger and the middle finger of the hand, and the ulnar side of the hand is resting on the planar surface, and
    wherein the fourth surface is a contoured inner surface of the hand formed by the intersections of the first surface, the second surface and the third surface with the hand that form the boundaries of the fourth surface with the hand to provide the shape measurement for the handle for the hand.

5. The method for designing a handle for a hand according to claim 4, wherein the position in which the hand is set is the T position.

6. The method for designing a handle for a hand according to claim 4, further comprising the steps of:
    mapping a first line distal from the base of the thumb of the hand traveling in the ulnar direction to end before the longitudinal crease of the hand;
    mapping a second line distal to the pisiform bone on the ulnar side of the hand from the ulnar side of the hand and traveling toward the radial side of the hand across approximately ⅔ of the hypothenar muscle area of the hand;
    mapping a third line extending from the thenar muscle area of the hand to the hypothenar muscle area at the horizontal creases of the hand; and
    linking the first line, the second line and the third line with a first longitudinal line and a second longitudinal line that cross the palm of the hand thereby defining a proximal side for a handle to provide a proximal boundary measurement for the proximal side of the handle for the hand.

7. The method for designing a handle for a hand according to claim 6, further comprising the step of:
    combining the shape measurement for the handle with the proximal boundary measurement for the handle to provide a volumetric measurement for the handle for the hand.

8. The method for designing a handle according to claim 7, further comprising the steps of:
    measuring a first angular degree of flexion at the proximal interphalangeal joint (PIP) of the long fingers of the hand with the hand set in a position for measurement for the handle;
    measuring a second angular degree of flexion at the distal interphalangeal joint (DIP) of the long fingers of the hand with the hand set in the position for measurement for the handle;
    measuring a third angular degree of flexion at the metacarpalphalangeal joint (MP) of the long fingers of the hand with the hand set in the position for measurement for the handle;
    measuring a fourth angular degree of flexion at the distal interphalangeal joint (DIP) of the thumb of the hand with the hand set in the position for measurement for the handle; and
    combining the measurements of the first angular degree of flexion, the second angular degree of flexion, the third angular degree of flexion and the fourth angular degree of flexion to provide a range of distance for the handle from the proximal side to the distal side of the handle and to provide a range of distance for the handle from the palmar side to the thumb side of the handle.

9. The method for designing a handle according to claim 6, further comprising the steps of:
    measuring a first angular degree of flexion at the proximal interphalangeal joint (PIP) of the long fingers of the hand with the hand set in a position for measurement for the handle;
    measuring a second angular degree of flexion at the distal interphalangeal joint (DIP) of the long fingers of the hand with the hand set in the position for measurement for the handle;

measuring a third angular degree of flexion at the metacarpalphalangeal joint (MP) of the long fingers of the hand with the hand set in the position for measurement for the handle;

measuring a fourth angular degree of flexion at the distal interphalangeal joint (DIP) of the thumb of the hand with the hand set in the position for measurement for the handle; and combining the measurements of the first angular degree of flexion, the second angular degree of flexion, the third angular degree of flexion and the fourth angular degree of flexion to provide a range of distance for the handle from the proximal side to the distal side of the handle and to provide a range of distance for the handle from the palmar side to the thumb side of the handle.

10. A method for designing a handle for a human hand, comprising the steps of:

measuring a first angular degree of flexion at the proximal interphalangeal joint (PIP) of the long fingers of the hand with the hand set in a position for measurement for the handle;

measuring a second angular degree of flexion at the distal interphalangeal joint (DIP) of the long fingers of the hand with the hand set in the position for measurement for the handle;

measuring a third angular degree of flexion at the metacarpalphalangeal joint (MP) of the long fingers of the hand with the hand set in the position for measurement for the handle;

measuring a fourth angular degree of flexion at the distal interphalangeal joint (DIP) of the thumb of the hand with the hand set in the position for measurement for the handle; and combining the measurements of the first angular degree of flexion, the second angular degree of flexion, the third angular degree of flexion and the fourth angular degree of flexion to provide a range of distance for the handle from the proximal side to the distal side of the handle and to provide a range of distance for the handle from the palmar side to the thumb side of the handle.

11. A method for designing a handle for a human hand, comprising the steps of:

mapping a first line distal from the base of the thumb of the hand traveling in the ulnar direction to end before the longitudinal crease of the hand;

mapping a second line distal to the pisiform bone on the ulnar side of the hand from the ulnar side of the hand and traveling toward the radial side of the hand across approximately ⅔ of the hypothenar muscle area of the hand;

mapping a third line extending from the thenar muscle area of the hand to the hypothenar muscle area at the horizontal creases of the hand; and linking the first line, the second line and the third line with a first longitudinal line and a second longitudinal line that cross the palm of the hand thereby defining a proximal side for a handle without placing substantial pressure on the carpal tunnel of the hand to provide a proximal boundary measurement for the proximal side of the handle for the hand.

12. The method for designing a handle for a hand according to claim 11, further comprising the step of:

setting the hand in the T position.

13. A method for designing an apparatus for engaging a human hand that corresponds to sizes of hands, comprising the steps of:

setting the hand in a T position so that the tips of the of the long fingers of the hand are substantially in alignment;

measuring the distance across the metacarpal bones of the long fingers of the hand from the radial side to the ulnar side across the horizontal creases of the hand thereby defining a length of the apparatus;

mapping a first line distal from the base of the thumb of the hand traveling in the ulnar direction to end before the longitudinal crease of the hand;

mapping a second line distal to the pisiform bone on the ulnar side of the hand from the ulnar side of the hand and traveling toward the radial side of the hand across approximately ⅔ of the hypothenar muscle area of the hand;

mapping a third line extending from the thenar muscle area of the hand to the hypothenar muscle area at the horizontal creases of the hand; and linking the first line, the second line and the third line with a first longitudinal line and a second longitudinal line that cross the palm of the hand thereby defining a proximal side for the apparatus of a corresponding size for a hand.

14. The method for designing an apparatus according to claim 13, further comprising the steps of:

measuring a first angular degree of flexion at the proximal interphalangeal joint (PIP) of the long fingers of the hand with the hand set in a position for measurement for the apparatus;

measuring a second angular degree of flexion at the distal interphalangeal joint (DIP) of the long fingers of the hand with the hand set in the position for measurement for the apparatus;

measuring a third angular degree of flexion at the metacarpalphalangeal joint (MP) of the long fingers of the hand with the hand set in the position for measurement for the apparatus;

measuring a fourth angular degree of flexion at the distal interphalangeal joint (DIP) of the thumb of the hand with the hand set in the position for measurement for the apparatus; and combining the measurements of the first angular degree of flexion, the second angular degree of flexion, the third angular degree of flexion and the fourth angular degree of flexion to provide a range of distance for the apparatus from the proximal side to the distal side of the apparatus and to provide a range of distance for the apparatus from the palmar side to the thumb side of the apparatus, wherein the apparatus for the hand avoids placing substantial pressure on the middle section of the palm of the hand over the region of the carpal tunnel.

15. A method for designing an apparatus for a human hand, comprising the steps of:

setting the hand in a position so that the tips of the long fingers of the hand are substantially in alignment, the thumb of the hand opposes the index finger and the middle finger of the hand, and the ulnar side of the hand is resting on a planar surface; and combining the edges of a first surface, a second surface and a third surface to form a fourth surface to determine a shape measurement for an apparatus for the hand, and wherein the first surface is the horizontal plane of the planar surface on which the ulnar side of the hand rests, wherein the second surface is a horizontal plane that touches the radial side of the hand and is parallel to the horizontal plane of the planar surface on which the hand rests, wherein the third surface is vertical to the horizontal plane of the planar surface on which the hand rests, and the third surface starts at the surface of the thenar eminence at the base of the thumb of the hand and ends at the palmar surface of the long fingers of the hand, and the position at which the third surface meets the long fingers of the hand is dependent upon the distance of the space between the thumb of the hand and the index finger of the hand when the hand is set in the position so that the tips of the long fingers of the hand are substantially in alignment, and the thumb of the hand opposes the index finger and the middle finger of the hand, and the ulnar side of the hand is resting on the planar surface, and wherein the fourth surface is a contoured inner surface of the hand formed by the intersections of the first surface, the second surface and the third surface with the hand that form the boundaries of the fourth surface with the hand to provide the shape measurement for the apparatus for the hand.

16. The method for designing an apparatus for a hand according to claim 15, wherein the position in which the hand is set is the T position.

17. The method for designing an apparatus for a hand according to claim 15, further comprising the steps of:

measuring a first angular degree of flexion at the proximal interphalangeal joint (PIP) of the long fingers of the hand with the hand set in a position for measurement for the apparatus;

measuring a second angular degree of flexion at the distal interphalangeal joint (DIP) of the long fingers of the hand with the hand set in the position for measurement for the apparatus;

measuring a third angular degree of flexion at the metacarpalphalangeal joint (MP) of the long fingers of the hand with the hand set in the position for measurement for the apparatus;

measuring a fourth angular degree of flexion at the distal interphalangeal joint (DIP) of the thumb of the hand with the hand set in the position for measurement for the apparatus; and combining the measurements of the first angular degree of flexion, the second angular degree of flexion, the third angular degree of flexion and the fourth angular degree of flexion to provide a range of distance for the apparatus from the proximal side to the distal side of the apparatus and to provide a range of distance for the apparatus from the palmar side to the thumb side of the apparatus.

18. The method for designing an apparatus for a hand according to claim 17, further comprising the step of:

providing a range of shapes for the apparatus dependent upon the angles made by the fingers of the hand at the joints of the fingers of the hand.

19. The method for designing an apparatus for a hand according to claim 18, further comprising the step of:

setting the hand in the T position as the position for measurement for the apparatus.

20. The method for designing an apparatus for a hand according to claim 17, wherein the position in which the hand is set is the T position.

21. The method for designing an apparatus for a hand according to claim 15, further comprising the steps of:

mapping a first line distal from the base of the thumb of the hand traveling in the ulnar direction to end before the longitudinal crease of the hand;

mapping a second line distal to the pisiform bone on the ulnar side of the hand from the ulnar side of the hand and traveling toward the radial side of the hand across approximately ⅔ of the hypothenar muscle area of the hand;

mapping a third line extending from the thenar muscle area of the hand to the hypothenar muscle area at the horizontal creases of the hand; and linking the first line, the second line and the third line with a first longitudinal line and a second longitudinal line that cross the palm of the hand thereby defining a proximal side for an apparatus having a portion away from the carpal tunnel of the hand to provide a proximal boundary measurement for the proximal side of the apparatus for the hand.

22. The method for designing an apparatus for a hand according to claim 21, further comprising the steps of:

measuring a first angular degree of flexion at the proximal interphalangeal joint (PIP) of the long fingers of the hand with the hand set in a position for measurement for the apparatus;

measuring a second angular degree of flexion at the distal interphalangeal joint (DIP) of the long fingers of the hand with the hand set in the position for measurement for the apparatus;

measuring a third angular degree of flexion at the metacarpalphalangeal joint (MP) of the long fingers of the hand with the hand set in the position for measurement for the apparatus;

measuring a fourth angular degree of flexion at the distal interphalangeal joint (DIP) of the thumb of the hand with the hand set in the position for measurement for the apparatus; and combining the measurements of the first angular degree of flexion, the second angular degree of flexion, the third angular degree of flexion and the fourth angular degree of flexion to provide a range of distance for the apparatus from the proximal side to the distal side of the apparatus and to provide a range of distance for the apparatus from the palmar side to the thumb side of the apparatus.

23. The method for designing an apparatus for a hand according to claim 22, further comprising the step of:

providing a range of shapes for the apparatus dependent upon the angles made by the fingers of the hand at the joints of the fingers of the hand.

24. The method for designing an apparatus for a hand according to claim 23, further comprising the step of:

setting the hand in the T position as the position for measurement for the apparatus.

25. The method for designing an apparatus for a hand according to claim 22, further comprising the step of:

combining the shape measurement for the apparatus with the proximal boundary measurement for the apparatus to provide a volumetric measurement for the apparatus for the hand.

26. The method for designing an apparatus for a hand according to claim 22, wherein the position in which the hand is set is the T position.

* * * * *